US011832961B2

(12) United States Patent
Shin et al.

(10) Patent No.: US 11,832,961 B2
(45) Date of Patent: *Dec. 5, 2023

(54) CONTACTLESS SLEEP DETECTION AND DISTURBANCE ATTRIBUTION

(71) Applicant: Google LLC, Mountain View, CA (US)

(72) Inventors: Dongeek Shin, Mountain View, CA (US); Michael Dixon, Sunnyvale, CA (US); Andrew William Goldenson, Belmont, CA (US)

(73) Assignee: Google LLC, Mountain View, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/990,705

(22) Filed: Aug. 11, 2020

(65) Prior Publication Data

US 2022/0047208 A1    Feb. 17, 2022

(51) Int. Cl.
*A61B 5/00* (2006.01)
*A61B 5/11* (2006.01)
(Continued)

(52) U.S. Cl.
CPC .......... *A61B 5/4809* (2013.01); *A61B 5/0004* (2013.01); *A61B 5/11* (2013.01); *A61B 5/742* (2013.01); *A61B 5/749* (2013.01); *G01S 13/282* (2013.01); *G01S 13/62* (2013.01); *A61B 2562/0271* (2013.01)

(58) Field of Classification Search
None
See application file for complete search history.

(56) References Cited

U.S. PATENT DOCUMENTS 8,520,784 B1   8/2013 Lackey
8,742,935 B2   6/2014 Cuddihy et al.
(Continued)

FOREIGN PATENT DOCUMENTS

AU    2012-308234 A1    5/2014
EP       3511732 A2     7/2019
(Continued)

OTHER PUBLICATIONS

International Search Report and Written Opinion dated Jun. 18, 2021 in International Patent Application No. PCT/US2020/051776, 13 pages.

(Continued)

*Primary Examiner* — Catherine M Voorhees
*Assistant Examiner* — Elizabeth K So
(74) *Attorney, Agent, or Firm* — Kilpatrick Townsend & Stockton LLP

(57) ABSTRACT

Various systems, devices, and methods for contactless sleep tracking are presented. Based on data received from a contactless sensor, such as a radar sensor, determine that a user has entered a sleep state. A transition time may be determined at which the user transitions from the sleep state to an awake state. An environmental event, based on data received from an environmental sensor, may be identified as occurring within a time period of the transition time. The user waking may be attributed to the environmental event based on the environmental event occurring within the time period of the transition time. An indication of the attributed environmental event as a cause of the user waking may be output.

19 Claims, 30 Drawing Sheets

(51) Int. Cl.
  *G01S 13/62*  (2006.01)
  *G01S 13/28*  (2006.01)

(56) References Cited

U.S. PATENT DOCUMENTS

| | | | |
|---|---|---|---|
| 9,754,471 | B2 | 9/2017 | Berezhnyy et al. |
| 10,058,290 | B1 | 8/2018 | Proud |
| 10,206,610 | B2 | 2/2019 | Al-Alusi |
| 10,417,923 | B2 | 9/2019 | Walter et al. |
| 10,690,763 | B2 | 6/2020 | Shouldice et al. |
| 11,250,942 | B1 | 2/2022 | Ahmad et al. |
| 2003/0011516 | A1 | 1/2003 | Moch |
| 2008/0081657 | A1 | 4/2008 | Suzuki et al. |
| 2008/0300572 | A1 | 12/2008 | Rankers et al. |
| 2010/0152600 | A1 | 6/2010 | Droitcour et al. |
| 2010/0153045 | A1* | 6/2010 | Teshirogi ............ H04B 17/102 343/703 |
| 2010/0283845 | A1 | 11/2010 | Yokochi et al. |
| 2011/0060215 | A1 | 3/2011 | Tupin, Jr. et al. |
| 2011/0190594 | A1 | 8/2011 | Heit et al. |
| 2013/0244644 | A1 | 9/2013 | Amirijoo et al. |
| 2016/0015315 | A1* | 1/2016 | Auphan ............... A61B 5/7435 600/587 |
| 2016/0321428 | A1 | 11/2016 | Rogers |
| 2018/0239014 | A1 | 8/2018 | McMahon |
| 2018/0322351 | A1 | 11/2018 | Shaker |
| 2018/0329049 | A1 | 11/2018 | Amihood et al. |
| 2018/0330589 | A1* | 11/2018 | Horling ............... G08B 25/008 |
| 2018/0330593 | A1 | 11/2018 | Zack et al. |
| 2019/0108913 | A1 | 4/2019 | Coke et al. |
| 2019/0187268 | A1 | 6/2019 | Lien et al. |
| 2019/0391249 | A1 | 12/2019 | Takeuchi et al. |
| 2020/0033470 | A1 | 1/2020 | Brankovic et al. |
| 2020/0178892 | A1 | 6/2020 | Maslik et al. |
| 2020/0195327 | A1 | 6/2020 | Thiagarajan et al. |
| 2020/0253508 | A1 | 8/2020 | Campbell |
| 2020/0367810 | A1 | 11/2020 | Shouldice et al. |
| 2020/0408876 | A1 | 12/2020 | Weber et al. |
| 2020/0410072 | A1* | 12/2020 | Giusti ................... G01S 13/56 |
| 2021/0030276 | A1 | 2/2021 | Li et al. |
| 2021/0037315 | A1 | 2/2021 | Eckert et al. |
| 2021/0088643 | A1 | 3/2021 | Hayashi et al. |
| 2021/0150873 | A1 | 5/2021 | Shouldice et al. |
| 2021/0244352 | A1 | 8/2021 | Campbell et al. |

FOREIGN PATENT DOCUMENTS

| | | | |
|---|---|---|---|
| WO | 2009105418 | A1 | 8/2009 |
| WO | 2018-050913 | A1 | 3/2018 |
| WO | WO-2018220087 | A1 * | 12/2018 ........... A61B 5/0022 |
| WO | 2019-122413 | A1 | 6/2019 |
| WO | 2019-202385 | A1 | 10/2019 |
| WO | 2020-104465 | A2 | 5/2020 |
| WO | 2020-176100 | A1 | 9/2020 |
| WO | 2020-176105 | A1 | 9/2020 |
| WO | 2020226638 | A1 | 11/2020 |
| WO | 2021-021220 | A1 | 2/2021 |
| WO | 2021-107958 | A1 | 3/2021 |
| WO | 2021-126209 | A1 | 6/2021 |
| WO | 2021137120 | A1 | 7/2021 |
| WO | 2021/177956 | A1 | 9/2021 |

OTHER PUBLICATIONS

International Search Report and Written Opinion for PCT/US2021/040643 dated Dec. 12, 2021, all pages.
International Search Report and Written Opinion dated Aug. 21, 2020 in International Patent Application No. PCT/US2019/065958, 15 pages.
International Search Report and Written Opinion dated Sep. 10, 2020 in International Patent Application No. PCT/US2019/066305, 11 pages.
"S+ by ResMed" [Web page], (n.d.). Retrieved on Jul. 10, 2020 from https://splus.resmed.com/ , 9 pages.
"X4" (n.d.). Retrieved on Jul. 10, 2020 from Novelda website https://novelda.com/x4-soc.html, 3 pages.
"Novelda Presence Sensor" (n.d.). Retrieved on Jul. 10, 2020 from Novelda website https://novelda.com/novelda-presence-sensor.html, 2 pages.
"A World Leader Within Ultra Wideband (UWB) Sensing", (n.d.). Retrieved on Jul. 10, 2020 from Novelda website https://novelda.com/, 3 pages.
Tran, V.P., et al., "Doppler Radar-Based Non-Contact Health Monitoring for Obstructive Sleep Apnea Diagnosis: A Comprehensive Review", Big Data and Cognitive Computing, vol. 3, Issue 1, Jan. 1, 2019, DOI: 10.3390/bdcc3010003, 21 pages.
International Search Report and Written Opinion for PCT/US2019/031290 dated Dec. 19, 2019, all pages.
International Preliminary Report on Patentability for PCT/US2019/031290 dated Nov. 2, 2021, all pages.
International Search Report and Written Opinion dated Apr. 30, 2021 in International Patent Application No. PCT/US2020/048388, 20 pages.
Yang. F., et al., "EM techniques for the detection of breast cancer," 2010 IEEE Antennas and Propagation Society International Symposium, (Year 2010), pp. 1-4, doi: 10.1109/APS.2010.5562289.
"Novelda Presence Sensor" (n.d.). Retrieved on Aug. 13, 2020 from Novelda website https://novelda.com/novelda-presence-sensor.html, 1 page.

* cited by examiner

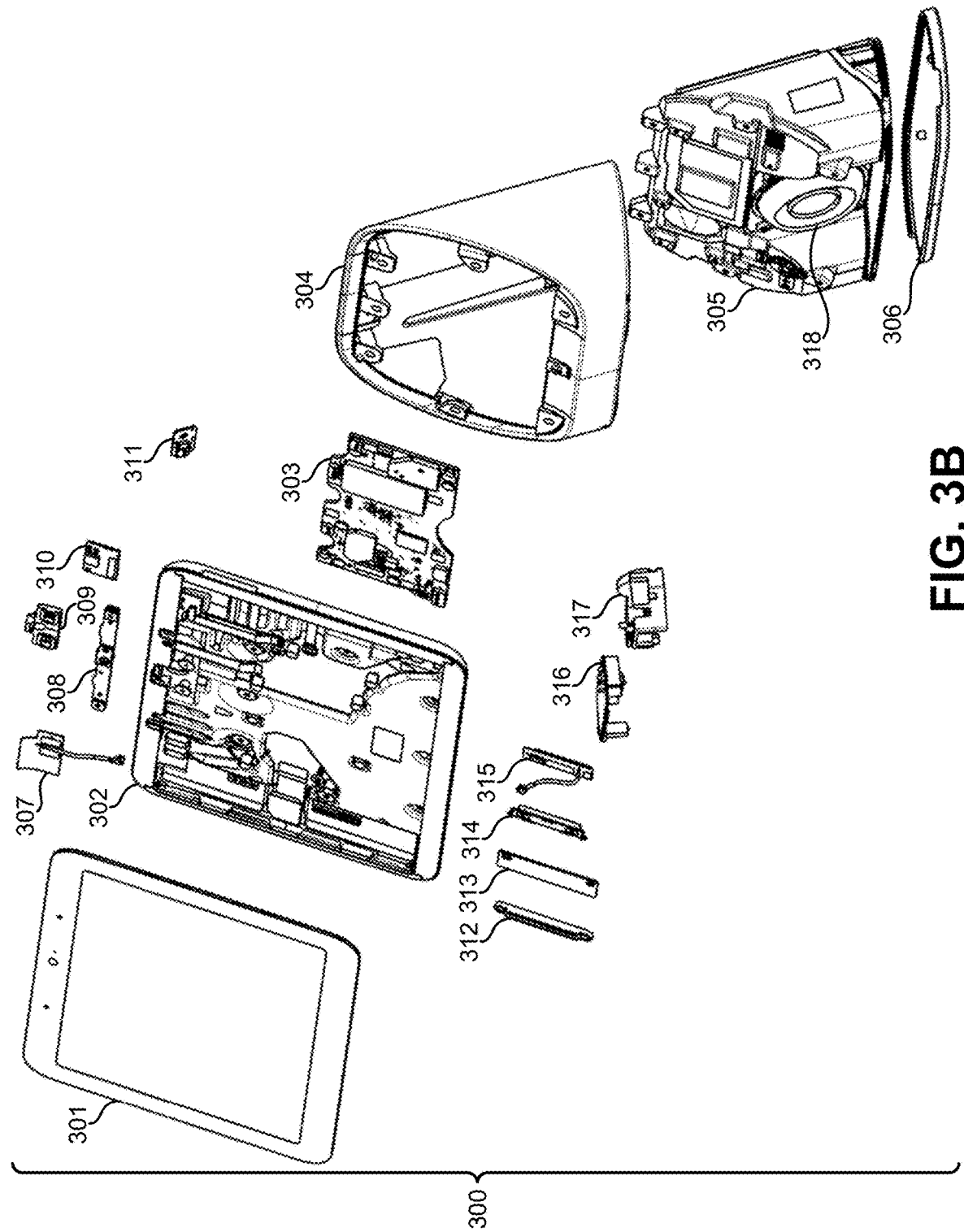

CONTACTLESS SLEEP DETECTION AND DISTURBANCE ATTRIBUTION

CROSS REFERENCE TO RELATED APPLICATION

This application is related to PCT Application US2019/031,290, filed May 8, 2019, entitled "Sleep Tracking and Vital Sign Monitoring Using Low Power Radio Waves." This application is also related to Non-Provisional application Ser. No. 16/990,746, filed Aug. 11, 2020, entitled "Initializing Sleep Tracking on a Contactless Health Tracking Device." This application is also related to Non-Provisional application Ser. No. 16/990,714, filed Aug. 11, 2020, entitled "Contactless Sleep Detection and Disturbance Attribution for Multiple Users." This application is also related to Non-Provisional application Ser. No. 16/990,720, filed Aug. 11, 2020, entitled "Contactless Cough Detection and Attribution," now U.S. Pat. No. 11,406,281, granted Aug. 9, 2022. This application is also related to Non-Provisional application Ser. No. 16/990,726, filed Aug. 11, 2020, entitled "Precision Sleep Tracking Using a Contactless Sleep Tracking Device." The entire disclosures of which are hereby incorporated by reference for all purposes.

BACKGROUND

A person may wake some number of times during the night. The person may have difficultly determining the reason as to why he woke up, especially if the source of the disturbance of waking up is short lived. In order to improve the person's sleep quality, by the person learning what is disturbing his sleep, the person may take preventative measures to address the source and decrease the presence or effect of future disturbances.

SUMMARY

Various embodiments are described related to a contactless sleep tracking device. In some embodiments, a contactless sleep tracking device is described. The device may include a housing. The device may include a first environmental sensor housed by the housing. The device may include a contactless sensor, housed by the housing, that may remotely monitor movement of a user. The device may include a processing system, comprising one or more processors, housed by the housing that may receive data from the first environmental sensor and the contactless sensor. The processing system may be configured to determine, based on data received from the contactless sensor, that the user has entered a sleep state. The processing system may be configured to determine a transition time at which the user transitions from the sleep state to an awake state. The processing system may be configured to identify an environmental event, based on data received from the first environmental sensor, occurring within a time period of the transition time. The processing system may be configured to attribute the user waking to the environmental event based on the environmental event occurring within the time period of the transition time. The processing system may be configured to output an indication of the attributed environmental event as a cause of the user waking.

Embodiments of such a device may include one or more of the following features: the contactless sensor may use low-power continuous wave (CW) radar. The first environmental sensor may be an ambient light sensor. The processing system being configured to identify the environmental event may comprise the processing system being configured to determine that an ambient light level has increased by at least a threshold amount (or by an amount significant enough to wake the user). The first environmental sensor may be a microphone. The processing system being configured to identify the environmental event may comprise the processing system being configured to determine that a sound louder than a sound event threshold has been detected, or a sound event significant enough to wake the user. The device may further include a second environmental sensor. The device may further include the processing system being configured to identify the environmental event may include the processing system being configured to compare data received from the first environmental sensor to a first threshold (or some other form of criterion). The device may further include the processing system being configured to compare data received from the second environmental sensor to a second threshold (or some other form of criterion). The processing system identifying the environmental event may be further based on: data received from the second environmental sensor, comparing data received from the first environmental sensor to the first threshold (or some other form of criterion), and comparing data received from the second environmental sensor to the second threshold (or some other form of criterion). The first environmental sensor may be a temperature sensor and the environmental event may be a temperature change of greater than a temperature threshold (or some other form of temperature-based criterion). The device may further include a wireless network interface housed by the housing. The device may further include an electronic display screen housed by the housing. The device may further include a microphone housed by the housing. The device may further include a speaker housed by the housing. The device may further include a stand incorporated as part of the housing. The processing system may be in communication with the wireless network interface, the display screen, the microphone, and the speaker. The processing system may be further configured to receive a voice-based query via the microphone. The processing system may be further configured to output information based on the voice-based query via the wireless network interface. The processing system may be further configured to receive data from a cloud-based server system via the wireless network interface. The processing system may be further configured to output a response to the voice-based query via the speaker. The response may indicate the attributed environmental event as the cause of the user waking. The processing system may be further configured to output the indication of the attributed environmental event via the electronic display screen, the speaker using synthesized speech, or both. The processing system may be further configured to output the indication of the attributed environmental event mapped to the transition time at which the user transitioned from the sleep state to the awake state.

In some embodiments, a method for performing contactless sleep monitoring is described. The method may include determining, based on data received from a contactless sensor, that a user may have entered a sleep state. The method may include determining a transition time at which the user transitions from the sleep state to an awake state. The method may include identifying an environmental event, based on data received from a first environmental sensor, occurring within a time period of the transition time. The method may include attributing the user waking to the environmental event based on the environmental event occurring within the time period of the transition time. The method may include outputting an indication of the attributed environmental event as a cause of the user waking.

Embodiments of such a method may include one or more of the following features: the data received from the contactless sensor may be based on low-power frequency-modulated continuous wave (FMCW) radar. The first environmental sensor may be an ambient light sensor. Identifying the environmental event may comprise determining that an ambient light level has increased by at least a threshold amount (or some other form of light-based criterion). The first environmental sensor may be an ambient light sensor. Identifying the environmental event may comprise determining that an ambient light level has increased to more than a threshold ambient light level (or some other form of light-based criterion). The first environmental sensor may be a microphone. Identifying the environmental event may comprise determining that a sound louder than a sound event threshold (or some other form of sound-based criterion) has been detected. The first environmental sensor may be a temperature sensor. Identifying the environmental event may comprise determining that a temperature change greater than a threshold amount (or some other form of temperature-based criterion) has been detected. The method may include receiving a voice-based query via a microphone. The method may include outputting a response to the voice-based query via a speaker. The response may indicate the attributed environmental event as the cause of the user waking. The method may further comprise output information based on the voice-based query via a wireless network interface. The method may further comprise receiving data from a cloud-based server system via the wireless network interface. Outputting the indication of the attributed event as the cause of the user waking may comprise outputting the indication of the attributed environmental event via an electronic display, a speaker using synthesized speech, or both. Determining the transition time, identifying the environmental event, attributing the user waking to the environmental event, and outputting the indication of the attributed environmental event as the cause of the user waking may be performed by a processing system of a contactless sleep tracking device. The first environmental sensor may be part of the contactless sleep tracking device.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 3B illustrates an exploded view of an embodiment of a contactless sleep tracking device.

DETAILED DESCRIPTION

Figure 1:
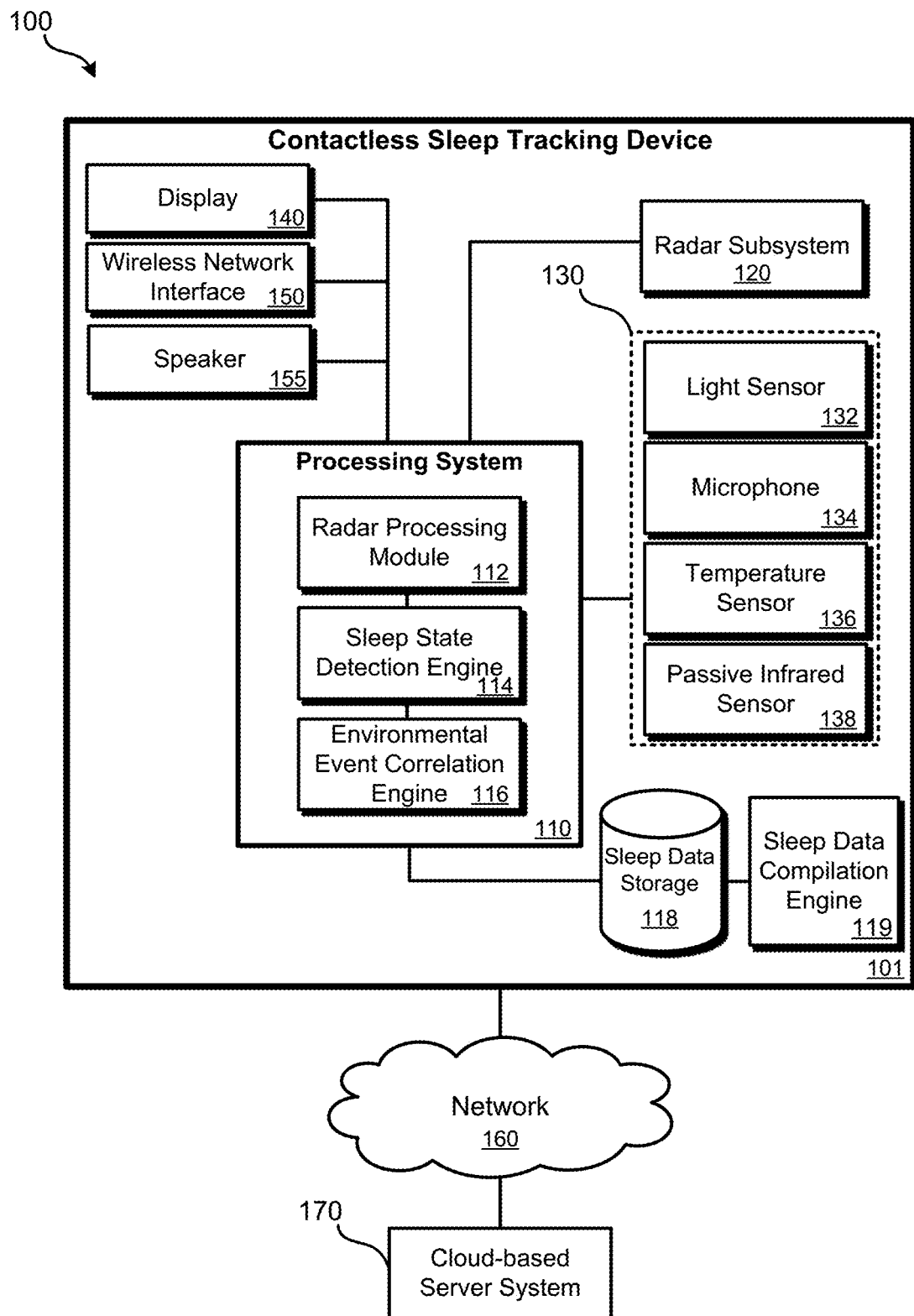
FIG. 1 illustrates an embodiment of a system for performing contactless sleep tracking.

Embodiments detailed herein are focused on performing contactless sleep monitoring, attributing causes of sleep interruptions, and systems and devices to perform contactless sleep monitoring and analysis. A single device may be situated bedside. For some embodiments, it is preferred that the single device makes no physical contact with a user or the user's bed. The device, without any physical contact, may monitor the user to assess whether the user is awake or asleep while in bed. When the user transitions from being asleep to awake, the device may determine what caused the user to wake. In addition to performing sleep monitoring, the device may monitor one or more environmental conditions, such as ambient sound, light, and temperature. If a loud enough sound, increase in lighting, and/or significant enough change in temperature are detected around the time that the user awoke, the environmental condition may be identified as the cause of the user waking.

Throughout one or more nights, the contactless sleep analysis device may monitor the user to determine when the user awoke during the night and what environmental condition may be to blame. When the user is awake, the user may be provided information indicative of when they awoke, how often they awoke and/or what, if any, environmental conditions were the likely causes of the user waking. If a same environmental condition is repeatedly attributed with causing the user to wake, the device may provide a recommendation that the user try to eliminate or decrease the presence of the environmental condition. For instance, if the lighting level in the user's sleeping environment tends to increase just before the user awakes, the user should address the cause of the lighting to improve their sleep. For instance, car headlights shining in a window or a display screen activating may be causing the light. To remedy, the user could adjust their window dressings or power down their display screen, respectively.

Detection of whether the user is asleep or awake may be accomplished using low-powered radar. Low-powered radar, which can involve the use of frequency-modulated continuous wave (FMCW) radar, may involve the contactless sleep analysis device emitting CW radar towards the user's bed. Reflected radio waves may be analyzed to determine a distance to the object that caused the reflection and a phase shift in the reflected radio waves. Large movements detected using radar may be used to determine if the user is awake or sleeping. Small movements may be used to measure the user's vital signs, such as heartrate and breathing rate.

FMCW can be particularly effective in observing vital signs of a user. Generally, FMCW allows for finer measurement of movement compared with ultra wideband (UWB). For example, devices based on UWB may be able to detect movement of 10 mm at a distance of 3 m, but FMCW devices may be able to measure movement of 2 mm at a similar distance. To realize this advantage, FMCW allows for the phase shift of emitted radio waves to be measured to detect small displacements of an object.

The contactless sleep analysis device may be highly privacy-preserving. Sleep data might not be collected without explicit permission being granted by a user. When sleep data is being collected, an indication as such may be presented on the display. In some embodiments, sleep-related data is not transmitted to a remote server. Rather, in such embodiments, the sleep data is available only at the device locally. In some embodiments, the user may be required to give explicit consent for any sleep-related data to be transmitted to a remote server for storage and/or analysis. In some embodiments, no identity of the user is stored with the sleep data; therefore it might not be possible to ascertain to whom the sleep data corresponds without additional information.

In some embodiments, sleep analysis may be performed on more than one user concurrently. In such multiple user arrangements, two users may be the most likely arrangement (e.g., two spouses); however, three or more users may also be possible (e.g., two spouses and small child). Such an arrangement can allow for a sleep analysis to be performed individually for each user. The contactless sleep analysis device may store or output sleep data for each user separately and may provide each user with a separate sleep report, which may be indicative of environmental events that likely caused the individual user to awake. Therefore, advantageously, despite a single contactless sleep analysis device being present, multiple users sleeping in a same bed may have their sleep separately monitored over a same time period.

As previously detailed for a single user, environmental factors may be monitored using one or more environmental sensors. Environmental factors may be monitored to determine if an environmental factor caused a user to wake. Additionally, a user waking may be attributed to another user moving. For instance, if a first user rolls over in bed, this motion may be identified as the environmental factor that caused the second user to wake.

Depending on the setup of a user's bedroom, the direction from the contactless sleep analysis device to where the one or more users sleep may vary. For example, a user may have the contactless sleep analysis device on a nightstand that is taller than the user's bed, while another user may have the sleep device on a nightstand that is the same height or shorter than the user's bed. Additionally or alternatively, the contactless sleep analysis device may be rotated horizontally at an angle to where the user sleeps. In some or all of the detailed embodiments herein, the direction monitored by the contactless sleep analysis device may be targeted vertically and/or horizontally toward the one or more users.

A beam-steering module, which may perform preprocessing on received digital data from a radar subsystem, may perform weighted delay and sum (WDAS) beam-steering.

Depending on the number and location of antennas through which reflected radio waves are sensed by the radar subsystem, targeting may be performed vertically and/or horizontally. Beam-steering may take into account the specific layout of antennas of the radar subsystem or may be antenna layout agnostic. Through a training process, a beam-steering direction in which the most vital-signal related movement occurs may be identified by the contactless sleep tracking device. The weights associated with this direction may be applied during sleep tracking such that digital beam-steering is performed to target the region where the user is likely located.

A contactless sleep detection device, with or without a beam-steering module, may be used for cough and/or snore detection and attribution for one or more users. Detecting a cough and/or snore based on audio can be a relatively accurate process. However, determining the particular source of the cough or snore may be challenging. In addition to or instead of performing sleep tracking, devices detailed herein can function as contactless cough detection and attribution devices. (While this document focuses on cough detection and attribution, such systems and methods can be applied to snoring or other sounds (e.g., talking in sleep) by using a detection system configured or trained to detect the desired sound.

If a contactless cough and/or snore detection and attribution device ("cough attribution device") is being used to monitor a single user, a determination can be made as to whether a detected cough was performed by the monitored user. For some embodiments, the cough attribution process is at least partially based on FMCW radar signals. For example, the cough may have originated from another person in the vicinity, a pet, or audio output by a television or other audio output device. If the cough attribution device is being used to monitor multiple users, the cough may be attributed to one of the monitored multiple users or attributed to none of the multiple users if the cough is determined to have originated from some source other than the multiple users (again, such as another person in the vicinity, a pet, or audio output by a television or other audio output device).

The cough attribution device may incorporate data about a monitored user coughing into a sleep report provided to the user or cough data may be presented in a stand-alone report. Cough data for a particular user may be compiled over an extended period of time (e.g., days, weeks, months) and may allow for cough trend information to be provided to the user, such as an indication that the amount of coughing by the user over the extended period of time is trending up, down, or remaining roughly constant.

To perform sleep tracking, cough detection and attribution, and/or other forms of health monitoring, a setup process may be performed to ensure that a user has positioned the sleep tracking device or cough attribution device appropriately and that the ambient environment is configured in such a way as to permit the device to operate properly. For some embodiments, the setup process includes training the system to look at or target the user or users typical sleeping location(s) in the bed using beam-steering. A user may request to setup sleep tracking (or other form of health monitoring process) and may take a mock sleeping position. Using radar, the user may be monitored to determine if the user is still within a distance range monitored by the sleep tracking device. The user may be determined to be static based on a trained machine-learning model or, possibly, by detecting the user's breathing to the exclusion of any other significant movements. If the user is determined to be present and static, the user may monitored for a period of time to determine if the user remains present and static for at least a threshold amount of time (or some other form of determination that uses a threshold criterion at least partially based on time). If a determination is made that the user has been classified as present and static for a sufficiently long period of time, sleep tracking may be activated and an indication may be output to the user indicating that setup has been successfully performed. By such a setup process being successfully completed, the device is pointed adequately towards where the user sleeps, is at an acceptable distance, and other moving objects have been removed from the environment. If either the user was not determined to be still or, once identified as still, the user was not classified as remaining within that state for a sufficient period of time, the setup process may fail and the user may be provided with recommendations on steps to take to improve the likelihood of it completing successfully when setup is again attempted.

Further detail regarding such embodiments and additional embodiments can be understood in relation to the figures. FIG. 1 illustrates an embodiment of a system 100 for performing contactless sleep detection and disturbance attribution. System 100 can include: contactless sleep tracking device 101 ("device 101"); network 160; and cloud-based server system 170. Device 101 can include: processing system 110; sleep data storage 118; radar subsystem 120; environmental sensor suite 130; display 140; wireless network interface 150; and speaker 155. Generally, device 101 can include a housing that houses all of the components of device 101. Further detail regarding such a housing, according to some embodiments, is provided in relation to FIG. 3A and FIG. 3B.

Processing system 110 can include one or more processors configured to perform various functions, such as the functions of: radar processing module 112; sleep state detection engine 114; and environmental event correlation engine 116. Processing system 110 can include one or more special-purpose or general-purpose processors. Such special-purpose processors may include processors that are specifically designed to perform the functions detailed herein. Such special-purpose processors may be ASICs or FPGAs which are general-purpose components that are physically and electrically configured to perform the functions detailed herein. Such general-purpose processors may execute special-purpose software that is stored using one or more non-transitory processor-readable mediums, such as random access memory (RAM), flash memory, a hard disk drive (HDD), or a solid state drive (SSD).

Radar subsystem 120 (also referred to as a radar sensor) can be a single integrated circuit (IC) that emits, receives, and outputs data indicative of a received, reflected waveform. The output of radar subsystem 120 may be analyzed using radar processing module 112 of processing system 110. Further detail regarding radar subsystem 120 and radar processing module 112 is provided in relation to FIG. 2.

Device 101 may include one or more environmental sensors, such as all, one, or some combination of the environmental sensors provided as part of environmental sensor suite 130. Environmental sensor suite 130 can include: light sensor 132; microphone 134; temperature sensor 136; and passive infrared (PIR) sensor 138. In some embodiments, multiple instances of some or all of these sensors may be present. For instance, in some embodiments, multiple microphones may be present. Light sensor 132 may be used for measuring an ambient amount of light present in the general environment of device 101. Microphone 134 may be used for measuring an ambient noise level present in the general environment of device 101. Temperature sensor 136 may be used for measuring an ambient temperature of the general environment of device 101. PIR sensor 138 may be used to detect moving living objects (e.g., persons, pets) within the general environment of device 101. Other types of environmental sensors are possible. For instance, a camera and/or humidity sensor may be incorporated as part of environmental sensor suite 130. As another example, active infrared sensors may be included. In some embodiments, some data, such as humidity data, may be obtained from a nearby weather station that has data available via the Internet. In some embodiments, active acoustic sensing methods, included, but not limited to sonar and ultrasound, and including either single or arrayed acoustic sources and/or receivers may be implemented. Such arrangements may be used as one or more adjunct sensing modalities incorporated with the other sensors and methods described herein.

In some embodiments, one, some, or all of sensors of environmental sensor suite 130 may be external device to 101. For instance, one or more remote environmental sensors may communicate with device 101, either directly (e.g., via a direct wireless communication method, via a low-power mesh network) or indirectly (e.g., through one or more other devices via the low-power mesh network, via an access point of a network, via a remote server).

Device 101 may include various interfaces. Display 140 can allow processing system 110 to present information for viewing by one or more users. Wireless network interface 150 can allow for communication using a wireless local area network (WLAN), such as a WiFi-based network. Speaker 155 can allow for sound, such as synthesized speech, to be output. For instance, responses to spoken commands received via microphone 134 may be output via speaker 155 and/or display 140. The spoken commands may be analyzed locally by device 101 or may be transmitted via wireless network interface 150 to cloud-based server system 170 for analysis. A response, based on the analysis of the spoken command, can be sent back to device 101 via wireless network interface 150 for output via speaker 155 and/or display 140. Additionally or alternatively, the speaker 155 and microphone 134 may be collectively configured for active acoustic sensing, including ultrasonic acoustic sensing. Additionally or alternatively, other forms of wireless communication may be possible, such as using a low-power wireless mesh network radio and protocol (e.g., Thread) to communicate with various smart home devices. In some embodiments, a wired network interface, such as an Ethernet connection, may be used for communication with a network. Further, the evolution of wireless communication to fifth generation (5G) and sixth generation (6G) standards and technologies provides greater throughput with lower latency which enhances mobile broadband services. 5G and 6G technologies also provide new classes of services, over control and data channels, for vehicular networking (V2X), fixed wireless broadband, and the Internet of Things (IoT). Such standards and technologies may be used for communication by device 101.

The low-power wireless mesh network radio and protocol may be used for communicating with power limited devices. A power-limited device may be an exclusively battery powered device. Such devices may rely exclusively on one or more batteries for power and therefore, the amount of power used for communications may be kept low in order to decrease the frequency at which the one or more batteries need to be replaced. In some embodiments, a power-limited device may have the ability to communicate via a relatively high power network (e.g., WiFi) and the low-power mesh network. The power-limited device may infrequently use the relatively high power network to conserve power. Examples of such power-limited devices include environmental sensors (e.g., temperature sensors, carbon monoxide sensors, smoke sensors, motion sensors, presence detectors) and other forms of remote sensors.

Notably, some embodiments of device 101 do not have any still camera or video camera. By not incorporating an on-board camera, users nearby may be reassured about their privacy. For example, device 101 can typically be installed in a user's bedroom. For many reasons, a user would not want a camera located in such a private space or aimed toward the user while the user is sleeping. In other embodiments, device 101 may have a camera, but the camera's lens may be obscured by a mechanical lens shutter. In order to use the camera, the user may be required to physically open the shutter to allow the camera to have a view of the environment of device 101. The user can be assured of privacy from the camera when the shutter is closed.

Wireless network interface 150 can allow for wireless communication with network 160. Network 160 can include one or more public and/or private networks. Network 160 can include a local wired or wireless network that is private, such as a home wireless local area network. Network 160 may also include a public network, such as the Internet. Network 160 can allow for device 101 to communicate with remotely located cloud-based server system 170.

Cloud-based server system 170 can provide device 101 with various services. Regarding sleep data, cloud-based server system 170 can include processing and storage services for sleep-related data. While the embodiment of FIG. 1 involves processing system 110 performing sleep state detection and environmental event correlation, in other embodiments, such functions may be performed by cloud-based server system 170. Also, in addition or in alternate to sleep data storage 118 being used to store sleep data, sleep-related data may be stored by cloud-based server system 170, such as mapped to a common user account to which device 101 is linked. If multiple users are monitored, the sleep data may be stored and mapped to a master user account or to the corresponding users' accounts.

Regardless of whether a single user or multiple users are monitored, each user may be required to provide their informed consent. Such informed consent may involve each user consenting to an end user agreement that involves data being used in compliance with HIPAA and/or other generally-accepted security and privacy standards for health information. Periodically, user may be required to renew their consent to collection of sleep data, such as annually. In some embodiments, each end user may receive a periodic notification, such as via a mobile device (e.g., smartphone) that reminds each user that their sleep data is being collected and analyzed and offers each user the option to disable such data collection.

Cloud-based server system 170 may additionally or alternatively provide other cloud-based services. For instance, device 101 may additionally function as a home assistant device. A home assistant device may respond to vocal queries from a user. In response to detecting a vocal trigger phrase being spoken, device 101 may record audio. A stream of the audio may be transmitted to cloud-based server system 170 for analysis. Cloud-based server system 170 may perform a speech recognition process, use a natural language processing engine to understand the query from the user, and provide a response to be output by device 101 as synthesized speech, an output to be presented on display 140, and/or a command to be executed by device 101 (e.g., raise the volume of device 101) or sent to some other smart home device. Further, queries or commands may be submitted to cloud-based server system 170 via display 140, which may be a touchscreen. For instance, device 101 may be used to control various smart home devices or home automation devices. Such commands may be sent directly by device 101 to the device to be controlled or may be sent via cloud-based server system 170.

Based on data output by radar processing module 112, sleep state detection engine 114 may be used to determine whether a user is likely asleep or awake. Sleep state detection engine 114 may progress through a state machine, such as detailed in relation to FIG. 5, or may use the state identified using such a state machine to determine whether the user is likely awake or asleep. For example, if a user is determined to be in bed and still for at least a period of time, the user may be identified as asleep. The output of sleep state detection engine 114 may be used by environmental event correlation engine 116. Environmental event correlation engine 116 may analyze data received from environmental sensor suite 130. Data from each environmental sensor device may be monitored for: 1) an increase of the environmental condition above a fixed defined threshold (or some other form of determination that uses a threshold criterion); and/or 2) an increase in the environmental condition by at least a predefined amount or percentage. Alternatively, some other form of threshold criterion may be used to analyze changes in the environmental condition. As an example, data indicating the light level in the ambient environment may be continuously or periodically output by light sensor 132. Environmental event correlation engine 116 may determine whether: 1) the ambient amount of lighting has increased from below a fixed defined threshold to above the fixed defined threshold (or some other form of determination that uses a threshold criterion at least partially based on lighting); and/or 2) the ambient amount of lighting has increased by at least a predefined amount of percentage. If options 1, 2, or both occur, it may be determined that an environmental event has occurred. This environmental event may be timestamped by environmental event correlation engine 116. Environmental event correlation engine 116 may then determine whether the user waking can be attributed to the identified environmental event. Further detail regarding the relationship between environmental events and sleep events is provided in relation to FIG. 6.

Figure 2A:
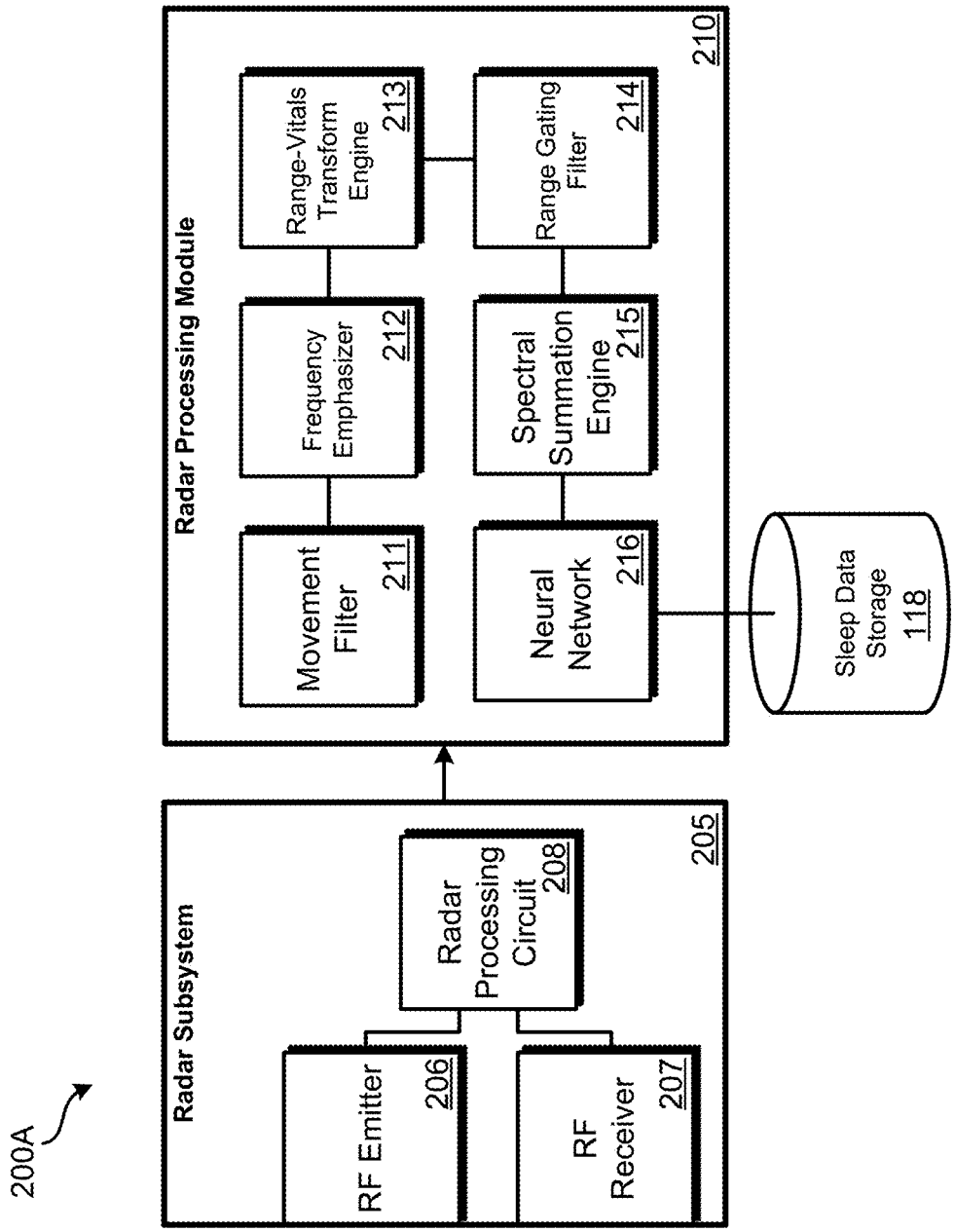
FIG. 2A illustrates an embodiment of a sleep tracking system.

FIG. 2A illustrates an embodiment of a sleep tracking system 200A ("system 200A"). System 200A can include radar subsystem 205 (which can represent an embodiment of radar subsystem 120); radar processing module 210 (which can represent an embodiment of radar processing module 112); and beam-steering module 230.

Radar subsystem 205 may include RF emitter 206, RF receiver 207, and radar processing circuit 208. RF emitter 206 can emit radio waves, such as in the form of continuous-wave (CW) radar. RF emitter 206 may use frequency-modulated continuous-wave (FMCW) radar. The FMCW radar may operate in a burst mode or continuous sparse-sampling mode. In burst mode, a frame or burst of multiple chirps, with the chirps spaced by a relatively short period of time, may be output by RF emitter 206. Each frame may be followed by a relatively long amount of time until a subsequent frame. In a continuous sparse-sampling mode, frames or bursts of chirps are not output, rather chirps are output periodically. The spacing of chirps in the continuous sparse sampling mode may greater in duration than the spacing between chirps within a frame of the burst mode. In some embodiments, radar subsystem 205 may operate in a burst mode, but output raw chirp waterfall data for each burst may be combined (e.g., averaged) together to create simulated continuous sparse-sampled chirp waterfall data. In some embodiments, raw waterfall data gathered in burst mode may be preferable for gesture detection while raw waterfall data gathered in a continuously-sparse sampling mode may be preferable for sleep tracking, vital sign detection, and, generally, health monitoring. Gesture detection may be performed by other hardware or software components that use the output of radar subsystem 205 that are not illustrated.

RF emitter 206 may include one or more antennas and may transmit at or about 60 GHz. The frequency of radio waves transmitted may repeatedly sweep from a low to high frequency (or the reverse). The power level used for transmission may be very low such that radar subsystem 205 has an effective range of several meters or an even shorter distance. Further detail regarding the radio waves generated and emitted by radar subsystem 205 are provided in relation to FIG. 2C.

RF receiver 207 includes one or more antennas, distinct from the transmit antenna(s), and may receive radio wave reflections off of nearby objects of radio waves emitted by RF emitter 206. The reflected radio waves may be interpreted by radar processing circuit 208 by mixing the radio waves being transmitted with the reflected received radio waves, thereby producing a mixed signal that can be analyzed for distance. Based on this mixed signal, radar processing circuit 208 may output raw waveform data, which can also be referred to as the raw chirp waterfall data for analysis by a separate processing entity. Radar subsystem 205 may be implemented as a single integrated circuit (IC) or radar processing circuit 208 may be a separate component from RF emitter 206 and RF receiver 207. In some embodiments, radar subsystem 205 is integrated as part of device 101 such that RF emitter 206 and RF receiver 207 are pointing in a same direction as display 140. In other embodiments, an external device that includes radar subsystem 205 may be connected with device 101 via wired or wireless communication. For example, radar subsystem 205 may be an add-on device to a home assistant device.

For radar subsystem 205, if FMCW is used, an unambiguous FMCW range can be defined. Within this range, a distance to objects can be accurately determined. However, outside of this range, a detected object could be incorrectly interpreted as nearer than an object within the unambiguous range. This incorrect interpretation can be due to the frequency of the mixed signal and the sampling rate of the ADC used by the radar subsystem to convert the received analog signals to digital signals. If the frequency of the mixed signal is above the Nyquist rate of the sampling of the ADC, the digital data output by the ADC representative of the reflected radar signal can be incorrectly represented (e.g., as a lower frequency indicative of a closer object).

When using device 201 to monitor sleep patterns and vital statistics, a user may be instructed that the user should be the closest person to the device 201. However, it may be possible that another person or an animal is present within the bed. It may be necessary to define the unambiguous FMCW range to be far enough, such as two meters, such that both persons (or, approximately the width of the bed) fall within the unambiguous FMCW range of radar subsystem 205. Two meters may be an ideal distance since this distance is approximately the width of a large commercially available bed (e.g., a king size bed).

Raw waveform data may be passed from radar subsystem 205 to radar processing module 210. The raw waveform data passed to radar processing module 210 may include waveform data indicative of continuous sparse reflected chirps due to radar subsystem 205 operating in a continuous sparse sampling mode or due to radar subsystem 205 operating in a burst mode and a conversion process to simulate raw waveform data produced by radar subsystem 205 operating in a continuous sparse sampling mode being performed. Processing may be performed to convert burst sampled waveform data to continuous sparse samples using an averaging process, such as each reflected group of burst radio waves being represented by a single averaged sample. Radar processing module 210 may include one or more processors. Radar processing module 210 may include one or more special-purpose or general-purpose processors. Special-purpose processors may include processors that are specifically designed to perform the functions detailed herein. Such special-purpose processors may be ASICs or FPGAs which are general-purpose components that are physically and electrically configured to perform the functions detailed herein. General-purpose processors may execute special-purpose software that is stored using one or more non-transitory processor-readable mediums, such as random access memory (RAM), flash memory, a hard disk drive (HDD), or a solid state drive (SSD). Radar processing module 210 may include: movement filter 211; frequency emphasizer 212; range-vitals transform engine 213; range gating filter 214; spectral summation engine 215; and neural network 216. Each of the components of radar processing module 210 may be implemented using software, firmware, or as specialized hardware.

The raw waveform data output by radar subsystem 205 may be received by radar processing module 210 and first processed using movement filter 211. In some embodiments, it is important that movement filter 211 is the initial component used to perform filtering. That is, the processing performed by radar processing module 210 is not commutative in some embodiments. Typically, vital sign determination and sleep monitoring may occur when a monitored user is sleeping or attempting to sleep in a bed. In such an environment, there may typically be little movement. Such movement may be attributed to the user moving within the bed (e.g., rolling over while trying to get to sleep or while asleep) and the user's vital signs, including movement due to breathing and movement due to the monitored user's heartbeat. In such an environment, a large portion of emitted radio waves from RF emitter 206 may be reflected by static objects in the vicinity of the monitored user, such as a mattress, box spring, bed frame, walls, furniture, bedding, etc. Therefore, a large portion of the raw waveform data received from radar subsystem 205 may be unrelated to user movements and the user's vital measurements.

Movement filter 211 may include a waveform buffer that buffers "chirps" or slices of received raw waveform data. For instance, sampling may occur at a rate of 10 Hz. In other embodiments, sampling may be slower or faster. Movement filter 211 may buffer twenty seconds of received raw waveform chirps in certain embodiments. In other embodiments, a shorter or longer duration of buffered raw waveform data is buffered. This buffered raw waveform data can be filtered to remove raw waveform data indicative of stationary objects. That is, for objects that are moving, such as a monitored user's chest, the user's heartbeat and breathing rate will affect the distance and velocity measurements made by radar subsystem 205 and output to movement filter 211. This movement of the user will result in "jitter" in the received raw waveform data over the buffered time period. More specifically, jitter refers to the phase shifts caused by moving objects reflecting emitted radio waves. Rather than using the reflected FMCW radio waves to determine a velocity of the moving objects, the phase shift induced by the motion in the reflected radio waves can be used to measure vital statistics, including heartrate and breathing rate, as detailed herein.

For stationary objects, such as furniture, a zero phase shift (i.e., no jitter) will be present in the raw waveform data over the buffered time period. Movement filter 211 can subtract out such raw waveform data corresponding to stationary objects such that motion-indicative raw waveform data is passed to frequency emphasizer 212 for further analysis. Raw waveform data corresponding to stationary objects may be discarded or otherwise ignored for the remainder of processing by radar processing module 210.

In some embodiments, an infinite impulse response (IIR) filter is incorporated as part of movement filter 211. Specifically, a single-pole IIR filter may be implemented to filter out raw waveform data that is not indicative of movement. Therefore, the single-pole IIR filter may be implemented as a high-pass, low-block filter that prevents raw waveform data indicative of movement below a particular frequency from passing through to frequency emphasizer 212. The cut-off frequency may be set based on known limits to human vital signs. For example, a breathing rate may be expected to be between 10 and 60 breaths per minute. Movement data indicative of a lower frequency than 10 breaths per minute may be excluded by the filter. In some embodiments, a band-pass filter may be implemented to exclude raw waveform data indicative of movement at high frequencies that are impossible or improbable for human vital signs. For instance, a heartrate, which can be expected to be above a breathing rate, may be unlikely to be above 150 beats per minute for a person in a resting or near-resting state. Raw waveform data indicative of a higher frequency may be filtered out by the band pass filter.

In some embodiments, it may be possible to further fine-tune the frequencies of raw waveform data that movement filter 211 passes to frequency emphasizer 212. For instance during an initial configuration phase, a user may provide information about the monitored user (e.g., himself, a child), such as age data. Table 1 indicates typical respiratory rates for various ages. Similar data may be present for heartrate. The filter may be configured to exclude data that is outside of the expected breathing rate, heartrate range, or both.

TABLE 1

| Age | Breathing Rate Range (breaths per minute) |
|---|---|
| Birth-6 weeks | 30-60 |
| 6 months | 25-40 |
| 3 years | 20-30 |
| 6 years | 18-25 |
| 10 years | 17-23 |
| Adults | 12-18 |
| 65-80 years old | 12-28 |
| >80 years old | 10-30 |

The vital signs of the monitored user being measured are periodic impulse events: a user's heartrate may vary over time, but it can be expected that the user's heart will continue to beat periodically. This beating is not a sinusoidal function, but rather may be understood as an impulse event, more analogous to a square wave having a relatively low duty cycle that induces motion in the user's body. Similarly, a user's breathing rate may vary over time, but breathing is a periodic function performed by the user's body that is analogous to sinusoidal function, except that a user's exhale is typically longer than their inhale. Further, at any given time, a particular window of waveform data is being analyzed. Since a particular time window of waveform data is being analyzed, even a perfect sinusoid within that window can result in spectral leakage in the frequency domain. Frequency components due to this spectral leakage should be deemphasized.

Frequency emphasizer 212 may work in conjunction with range-vitals transform engine 213 to determine the one (e.g., breathing) or two (e.g., breathing plus heartbeat) frequency components of the raw waveform data. Frequency emphasizer 212 may use frequency windowing, such as a 2D Hamming window (other forms of windowing are possible, such as a Hann window), to emphasize important frequency components of the raw waveform data and to deemphasize or remove waveform data that is attributable to spectral leakage outside of the defined frequency window. Such frequency windowing may decrease the magnitude of raw waveform data that is likely due to processing artifacts. The use of frequency windowing can help reduce the effects of data-dependent processing artifacts while preserving data relevant for being able to separately determine heartrate and breathing rate.

For a stationary bedside FMCW radar-based monitoring device, which may be positioned within 1 to 2 meters of the one or more users being monitored to detect breathing and heartrate (e.g., using radar as emitted in FIG. 2C), a 2D Hamming window that emphasizes frequencies in the range of 10 to 60 bpm (0.16 Hz to 1 Hz) for breathing and 30 to 150 bpm (0.5 to 2.5 Hz) for heartbeat provide for sufficiently good signals to make reliable measurements without requiring advance knowledge of the subject's age or medical history.

Since heartrate and breathing rate are periodic impulse events, the frequency domain heartrate, and breathing rate may be represented by different fundamental frequencies, but each may have many harmonic components at higher frequencies. One of the primary purposes of frequency emphasizer 212 may be to prevent the frequency ripples of harmonics of the monitored user's breathing rate from affecting the frequency measurement of the monitored user's heartrate (or the reverse). While frequency emphasizer 212 may use a 2D Hamming window, it should be understood that other windowing functions or isolating functions can be used to help isolate frequency ripples of the monitored user's breathing rate from the frequency ripples of the monitored user's heartrate.

Range-vitals transform engine 213 analyzes the received motion-filtered waveform data to identify and quantify the magnitude of movement at specific frequencies. More particularly, range-vitals transform engine 213 analyzes phase jitter over time to detect relatively small movements due to a user's vital signs that have a relatively low frequency, such as breathing rate and heart rate. The analysis of range-vitals transform engine 213 may assume that the frequency components of the motion waveform data are sinusoidal. Further, the transform used by range-vitals transform engine 213 can also identify the distance at which the frequency is observed. Frequency, magnitude, and distance can all be determined at least in part because radar subsystem 205 uses an FMCW radar system.

Prior to applying the transform of range-vitals transform engine 213, a zero-padding process may be performed by range-vitals transform engine 213 to add a number of zeros to the motion-filtered raw waveform data. By performing a zero-padding process, the resolution within the frequency domain can be increased effectively, allowing for more accurate low-rate measurements (e.g., a low heartrate, a low breathing rate). For example, zero-padding can help numerically increase resolution to detect differences of half a breath per minute compared to a resolution of a breath per minute without zero-padding. In some embodiments, three to four times the number of zeros compared to the buffered sample size of the raw waveform data may be added. For example, if twenty seconds of buffered raw waveform data are analyzed, sixty to eighty seconds' worth of zero padding may be added to the sample. Specifically, the range of three to four times zero padding of the sample was found to substantially increase resolution while not making the transform process overly complex (and, thus, processor use-intensive).

In order to determine the amount of zero padding to be performed, equations 1-3 may be used. In equation 1, RPM resolution may ideally be less than 1.

$$RPM_{resolution} = 60 * \frac{chirp\_rate}{n\_fft\_slow\_time} \quad \text{Eq. 1}$$

$$n\_FFT\_slow\_time\_min = (nearest\_power\_of\_2)(60 * chirp\_rate) \quad \text{Eq. 2}$$

In some embodiments, a chirp rate (chirp_rate) of 30 Hz may be used. Such a frequency may have sufficient margin from Nyquist limits of the upper limit of breathing rate and heartbeat rate. n_FFT_slow_time_min may, therefore, be 2048. Given a 20 second window for estimating respiration statistics, Equation 3 results in a value of 600.

$$n\_chirps\_for\_respiration = 20 * chirp\_rate = 600 \quad \text{Eq. 3}$$

This value of 600 is smaller than the required vitals-FFT size and makes range-vitals transform engine 213 perform a 3× to 4× zero padding. A balance in how much zero padding to perform may be based on increasing the frequency resolution and associated increases in the amount of computation needed to perform the FFT. A 3× to 4× zero padding has been found to provide sufficient resolution for heartrate and breath rate while moderating the amount of computation needing to be performed.

Range-vitals transform engine 213 can perform a series of Fourier transform (FT) to determine the frequency components of the received raw waveform data output by frequency emphasizer 212. Specifically, a series of fast Fourier transform (FFT) may be performed by range-vitals transform engine 213 to determine the specific frequencies and magnitudes of waveform data at such frequencies.

Waveform data obtained over a period of time can be expressed in multiple dimensions. A first dimension (e.g., along the y-axis) can relate to multiple samples of waveform data from a particular chirp and a second dimension (e.g., along the x-axis) relates to a particular sample index of waveform data gathered across multiple chirps. A third dimension of data (e.g., along the z-axis) is present indicative of the intensity of the waveform data.

Multiple FFTs may be performed based on the first and second dimension of the waveform data. FFTs may be performed along each of the first and second dimensions: an FFT may be performed for each chirp and an FFT may be performed for each particular sample index across multiple chirps that occurred during the period of time. An FFT performed on waveform data for a particular reflected chirp can indicate one or more frequencies, which, in FMCW radar, are indicative of the distances at which objects are present that reflected emitted radio waves. An FFT performed for a particular sample index across multiple chirps can measure the frequency of phase jitter across the multiple chirps. Therefore, the FFT of the first dimension can provide the distance at which a vital statistic is present and the FFT of the second dimension can provide a frequency of the vital statistic. The output of the FFTs performed across the two dimensions is indicative of: 1) the frequencies of vital statistics; 2) the ranges at which the vital statistics were measured; and 3) the magnitudes of the measured frequencies. In addition to values due to vital statistics being present in the data, noise may be present that is filtered, such as using spectral summation engine 215. The noise may be partially due to heartrate and breathing not being perfect sinusoidal waves.

To be clear, the transform performed by range-vitals transform engine 213 differs from a range-Doppler transform. Rather than analyzing changes in velocity (as in a range-Doppler transform), periodic changes in phase shift over time are analyzed as part of the range-vitals transform. The range-vitals transform is tuned to identify small movements (e.g., breathing, heart rate) occurring over a relatively long period of time by tracking changes in phase, referred to as phase jitter. As previously detailed, zero padding is performed to allow for sufficient resolution for accurate determination of heartrate and breathing rate.

Range gating filter 214 is used to monitor a defined range of interest and exclude waveform data due to movement beyond the defined range of interest. For arrangements detailed herein, the defined range of interest may be 0 to 1 meter. In some embodiments, this defined range of interest may be different or possibly set by a user (e.g., via a training or setup process) or by a service provider. In some embodiments, a goal of this arrangement may be to monitor the one person closest to the device (and exclude or segregate data for any other person farther away, such as a person sleeping next to the person being monitored). In other embodiments, if both persons are to be monitored, the data may be segregated, as detailed in relation to FIG. 12. Therefore, range-vitals transform engine 213 and range gating filter 214 serve to segregate, exclude, or remove movement data attributed to objects outside of the defined range of interest and sum the energy of movement data attributed to objects within the defined range of interest. The output of range gating filter 214 may include data that has a determined range within the permissible range of range gating filter 214. The data may further have a frequency dimension and a magnitude. Therefore, the data may possess three dimensions.

Spectral summation engine 215 may receive the output from range gating filter 214. Spectral summation engine 215 may function to transfer the measured energy of harmonic frequencies of the heartrate and breathing rate and sum the harmonic frequency energy onto the fundamental frequency's energy. This function can be referred to as a harmonic sum spectrum (HSS). Heartrate and breathing rate are not sinusoidal; therefore, in the frequency domain, harmonics will be present at frequencies higher than the fundamental frequency of the user's breathing rate and the fundamental frequency of the user's heartrate. One of the primary purposes of spectral summation engine 215 is to prevent harmonics of the monitored user's breathing rate from affecting the frequency measurement of the monitored user's heartrate (or the reverse). The HSS may be performed at the second order by summing the original spectrum with a down-sampled instance (by a factor of two) of the spectrum. This process may also be applied at higher order harmonics such that their respective spectra are added to the spectrum at the fundamental frequency.

At this stage, for a person in bed who is lying still (with the exception of movement due to breathing and heartrate), it will be expected that two major frequency peaks will present in the frequency data. However, if the monitored user is physically moving, such as rolling over in bed, the energy will be significantly distributed across the frequency spectrum (a broader distribution). Such large physical movement may manifest itself in the frequency data as being a large number of small peaks. If the bed is empty, rather than a person being present, there may be no or almost no frequency components above the noise floor since movement filter 211 has previously filtered raw waveform data corresponding to static objects. The distribution and magnitude of frequency peaks across the spectrum may be used to determine if the user is likely awake or asleep.

Spectral summation engine 215 may output a feature vector that is indicative of heartrate (e.g., in beats per minute) and breathing rate (e.g., in breaths per minute). The feature vector can indicate frequency and magnitude. Neural network 216 may be used to determine whether the heartrate and/or breathing rate indicated in the output of the feature vector from spectral summation engine 215 should be considered valid. Therefore, the heartrate and breathing rate output by spectral summation engine 215 may be stored, presented to a user, and/or treated as valid based on the output of neural network 216. Neural network 216 may be trained (e.g., using supervised learning performed using a training set of data) to output one of three states, such as those indicated in Table 2 by performing a spectral analysis. Vital statistic data may be considered valid when the user is determined to be present and the detected movement is due to the user's vital signs.

Each state in Table 2 is associated with a different spectral energy and spectral sparsity profile. Spectral energy refers to a summation of the energy across the frequency spectrum detected due to motion being present within the monitored region. Spectral sparsity represents whether movement tends to be distributed across a wide range of frequencies or clustered at a few specific frequencies. For instance, if energy peaks occur at few frequencies, such as when the user's vital signs are detected (but not other movement), spectral sparsity is high. However, if peaks (over a threshold value) or some other form of determination based on a threshold criterion at least partially based on magnitude) occur at many frequencies, spectral sparsity is low.

As an example, motion due to a vital sign, such as a heartbeat, may be indicative of significant movement (e.g., high spectral energy) at specific frequencies (e.g., high spectral sparsity); motion due to a user moving a limb may also be indicative of significant movement (high spectral energy), but may have low spectral sparsity. The neural network may be trained to distinguish between each state based on the spectral energy profile output by spectral summation engine 215. Therefore, neural network 216 may be provided two features, a first value representing spectral energy and a second value representing spectral sparsity.

The output of spectral summation engine 215 may be characterized as a feature vector having a first dimension of frequency and a second dimension of amplitude. The first value representing spectral energy may be calculated by determining the maximum amplitude present in the feature vector output by spectral summation engine 215. This maximum amplitude value may be normalized to a value within 0 to 1. The second value representing the spectral sparsity may be calculated by subtracting the median amplitude of the feature vector from the maximum amplitude. Again here, the calculated sparsity may be normalized to a value within 0 to 1.

Table 2 represents a generalization of how the features of spectral energy and spectral sparsity is used as features by the trained neural network to classify the state of the monitored region.

TABLE 2

| State of Monitored Region | Spectral Energy | Spectral Sparsity |
|---|---|---|
| User present and vitals-only movement | High | High |
| User present and moving (limb and torso movements) | High | Low |
| No user present | Low | Low |

The state of the monitored region classified by neural network 216 may be used in determining the monitored user's sleep state or, more generally, whether the user is moving or still within bed. The state of the monitored region as determined by the performed classification of neural network 216 may further be used to determine if the vital statistics output by spectral summation engine 215 should be trusted or ignored. For accurate vital statistic determination, heartrate and breathing rate may be identified as likely accurate when neural network 216 determines that the user is present and still (i.e., no large physical movements; however, movement is occurring due to breathing and/or heartbeat). In some embodiments, the vital statistics output by spectral summation engine 215 may be exclusively stored locally (e.g., to alleviate privacy concerns); in other embodiments, the vital statistics output may be transmitted to cloud-based server system 170 for remote storage (in alternative or in addition to such data being stored locally).

Neural network 216 may be initially trained using a large set of training data of amplitude and frequency feature vectors that have been properly tagged with a classification as mapping the spectral energy and the spectral sparsity to the corresponding ground-truth state of the monitored region. Alternatively, neural network 216 may be initially trained using a large set of training data of amplitude and frequency feature vectors that has been properly classified as mapping the comprising spectral energy and the spectral sparsity pairs each properly tagged to the corresponding ground-truth state of the monitored region. The neural network may be a fully connected neural network that is not time-dependent. In some embodiments, a machine-learning arrangement, classifier, or form of artificial intelligence other than a neural network may be used.

In other embodiments, rather than a spectral energy value and a spectral sparsity value being the features used by the neural network, a neural network, possibly with extra front-end convolutional layers, can be trained to use the output of range gating filter 214 directly. Rather, an embodiment of a convolutional network can analyze the frequency and magnitude data output by range gating filter 214 to classify the state of the user. The convolutional neural network may be trained to utilize offline training that is based on a set of spectral measurements mapped to the ground truth state of the monitored region prior to system 200B being used by an end user.

The sleep state determined by neural network 216 may be stored, along with time data, to sleep data storage 118. The vital statistics output by spectral summation engine 215 can be stored to a vital statistic datastore when neural network 216 indicates that the monitored user is present and still. Other vital statistic data may be discarded or possibly flagged to indicate it is less likely to be correct. The data stored to sleep data storage 118 and a vital statistic datastore may be stored locally at device 101. In some embodiments, storage occurs at only device 101. Such an implementation may help alleviate a concern about health-related data being transmitted and stored remotely. In some embodiments, the monitored user may elect to have sleep data and vital statistic data transmitted via a network interface (e.g., wireless network interface 150), stored, and analyzed externally, such as by cloud-based server system 170. Storage by cloud-based server system 170 may have significant benefits, such as the ability for the user to access such data remotely, allow access to a medical provider, or participate in research studies. The user may retain the ability to delete or otherwise remove the data from cloud-based server system 170 at any time.

In some embodiments, radar processing module 210 may be wholly or partly located remotely from device 101. While radar subsystem 205 may need to be local to the monitored user, the processing of radar processing module 210 may be moved to cloud-based server system 170. In other embodiments, a smart home device that is in local communication (e.g., via a LAN or WLAN) with device 101 may perform some or all of the processing of radar processing module 210. In some embodiments, a local communication protocol, such as involving a mesh network, can be used to transmit the raw waveform data to the local device that will be performing the processing. Such communication protocols can include Wi-Fi, Bluetooth, Thread, or communication protocols of the IEEE 802.11 and 802.15.4 families. Similar to the processing, storage of the sleep data and vital statistic data may occur at cloud-based server system 170 or another smart home device in the home at which device 101 is located. In still other embodiments, radar processing module 210 may be incorporated with radar subsystem 205 as a single component or system of components.

The stored sleep data of sleep data storage 118 and the vital statistic data may be used to provide the user with short-term and long-term trends relating to their sleeping patterns, vital statistics, or both by sleep data compilation engine 119. For instance, each morning, graphs, statistics, and trends may be determined by sleep data compilation engine 119 based on data stored to sleep data storage 118 and output for display by sleep data compilation engine 119 via display 140. A graph that is indicative of sleep data from the previous night and possibly one or more graphs indicative of breathing rates and heartrate during the previous night may be presented. Similar graphs, trends, and statistics may be output for significantly longer periods of time, such as weeks, months, years, and even multi-year stretches of time by sleep data compilation engine 119. Other uses for sleep data and vital statistics may be possible. For instance, if certain triggers regarding heartrate, breathing rate, and/or sleeping patterns are triggered, a medical professional may be notified. Additionally or alternatively, a notification may be output to the user indicating that the collected data is potentially concerning or is indicative of a healthy person. In some instances, specific sleep problems may be identified, such as sleep apnea. Sleep data may be output via speaker 155 using synthesized speech (e.g., in response to the user waking, in response to a spoken user command, or in response to a user providing input via a touchscreen, such as display 140). Such sleep data may also be represented graphically and or textually on display 140.

System 200A may additionally include beam-steering module 230. Beam-steering module 230 may include channel weighting engine 231, which may be implemented similarly to the components of radar processing module 210 using software, firmware, and/or hardware. Beam-steering module 230 is illustrated as separate from radar processing module 210 because it processes data received from radar subsystem 205 to emphasize data received from a particular direction and deemphasize data received from other directions. Beam-steering module 230 may be implemented using the same hardware as radar processing module 210. For instance, beam-steering module 230 may be a software process that modifies the radar data received from radar subsystem 205 prior to movement filter 211 being applied. Device 101 may be a surface-top device that is intended to be placed in a particular location, connected with a continuous power supply (e.g., a household power outlet) and interacted with via voice and/or a touchscreen. Therefore, radar subsystem 205 may remain pointed at a portion of the ambient environment for significant periods of time (e.g., multiple hours, days, weeks, months). Generally speaking, beam-steering module 230 may be used to map the environment (e.g., room) in which device 101 is located and steer the sensing direction of radar subsystem 205 to a zone within the field-of-view of radar subsystem 205 most likely to have a user present.

Targeting the region within the field-of-view of radar subsystem 205 may help decrease an amount of false negatives and false positives caused by movement of objects other than a user. Further, targeting can help compensate for an angle and location of device 101 relative to where the user sleeps. (For instance, device 101 may be located on a nightstand that is at a different height than the user's bed. Additionally or alternatively, radar subsystem 205 device 101 might not be pointed directly at the location in the bed where the user sleeps.)

When no user is determined to be present, such as based on low spectral energy and low spectral density of Table 2, an optimal beam steering process may be performed by channel weighting engine 231 and beam steering system 232. While no user is present, an analysis can be performed to determine which directional alignment of radar subsystem 205 provides minimal-clutter.

Figure 2B:
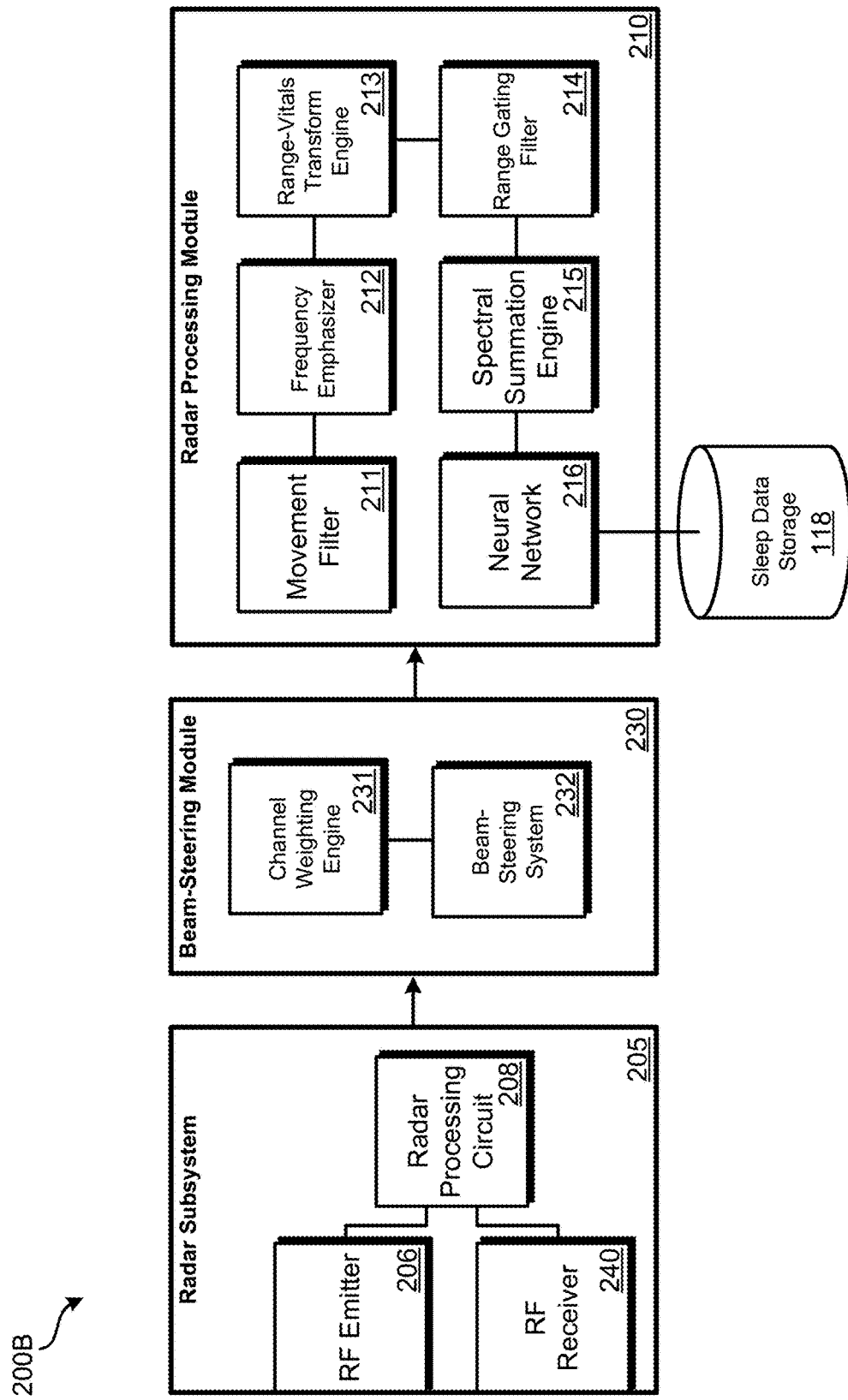
FIG. 2B illustrates an embodiment of a sleep tracking system with integrated beam targeting.

FIG. 2B illustrates an embodiment of a sleep tracking system 200B ("system 200B") which can perform beam targeting. Beam targeting performed by using beam-steering module 230 can focus on radar reflections from a region in which a user may be present and ignore or at least decrease the use of radar reflections from objects that cause interference, such as a nearby wall or large object.

Radar subsystem 240 may contain multiple antennas to receive reflected radar radio waves. In some embodiments, three antennas may be present. These antennas may be aligned in an "L" pattern, such that two antennas are horizontally orthogonal and two antennas are vertically orthogonal with one of the antennas being used in both the horizontal arrangement and vertical arrangement. By analyzing the phase difference in received radar signals, a weighting may be applied to target the received radar beam vertically and/or horizontally. In other embodiments, the antennas may be aligned in a different pattern and/or the beam targeting may be performed using a single receive antenna and multiple transmit antennas or by both multiple transmit and multiple receive antennas.

Vertical targeting may be performed to compensate for a vertical tilt of the device in which system 200B is incorporated. For instance, as discussed below in relation to FIG. 3A, the face of contactless sleep tracking device 300 may be tilted with respect to where a user will typically be sleeping.

Horizontal targeting may be performed to compensate for emitted radar being pointed towards an object that causes interference. For instance, if a user's bed headboard is against a wall, the headboard and/or wall may occupy a significant portion of the field-of-view of radar subsystem 120. Radar reflections from the headboard and/or wall are not be useful in determining data about the user; therefore, it may be beneficial to deemphasize reflections from the wall and/or headboard and emphasize reflections obtained away from the wall and/or headboard. Therefore, the receive beam may be steered horizontally away from the wall and the headboard by weighting applied to the received radar signals.

In system 200B, beam-steering module 230 is present to perform processing on the raw chirp waterfall received from radar subsystem 205 before processing is performed by radar processing module 210. Therefore, beam-steering module 230 can function as a preprocessing module prior to the analysis of radar processing module 210 and can serve to emphasize regions where one or more users are expected to be present. Beam-steering module 230 may be implemented using hardware, software, or firmware; therefore, beam-steering module 230 may be implemented using the same one or more processors as radar processing module 210.

Beam-steering module 230 can include channel weighting engine 231 and beam steering system 232. Channel weighting engine 231 can be used to perform a training process to determine a series of weightings to be applied to received radar signals from each antenna prior to the received radar signals being mixed together. Channel weighting engine 231 may perform a training process when a monitored region is determined to be empty. During such time, the strength of signals received from large static objects (e.g., walls, headboards) can be analyzed and weightings can be set to steer the beam horizontally (and possibly vertically) away from such objects. Therefore, the amount of reflection in a static environment may be minimized for a particular distance range (e.g., up to one meter) from the device by channel weighting engine 231 steering the receive radar beam. Such training may also be performed when a user is present. That is, the receive beam of radar subsystem 205 can be steered to where motion is detected, or specifically, to where vital signs of a user are present.

The weightings determined by channel weighting engine 231 may be used by beam steering system 232 to individually apply a weight to the received reflected radar signals of each antenna. The received signals from each antenna may be weighted, then mixed together for processing by radar processing module 210. Further detail regarding how various embodiments of beam-steering module 230 may be implemented are detailed in relation to FIGS. 14-17. Beam-steering module 230 can be used in combination with any other embodiment detailed herein.

Figure 2C:
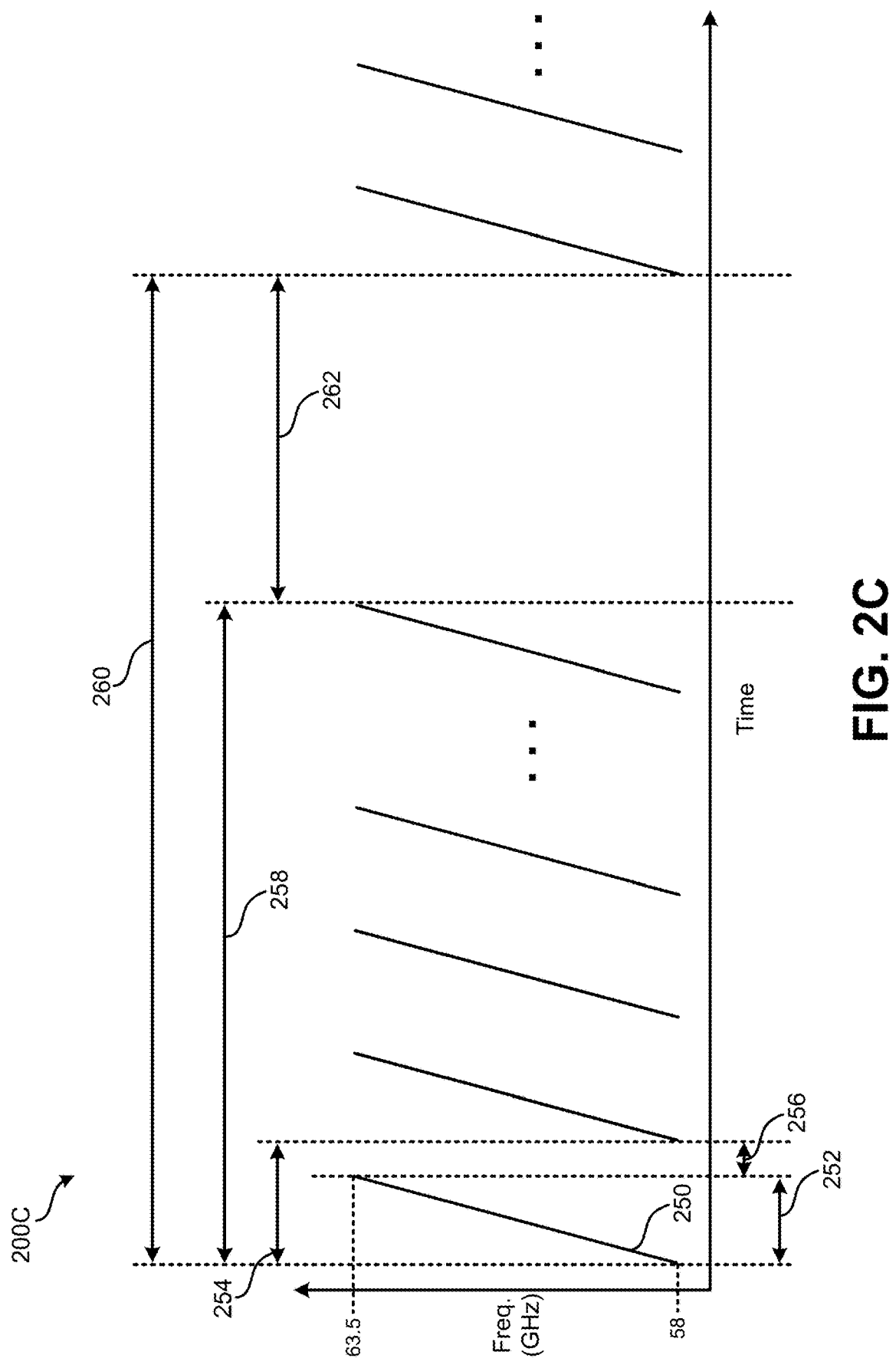
FIG. 2C illustrates an embodiment of frequency-modulated continuous wave radar radio waves output by a radar subsystem.

FIG. 2C illustrates an embodiment of chirp timing diagram 200C for frequency modulated continuous wave (FMCW) radar radio waves output by a radar subsystem. Chirp timing diagram 200C is not to scale. Radar subsystem 205 may generally output radar in the pattern of chirp timing diagram 200C. Chirp 250 represents a continuous pulse of radio waves that sweeps up in frequency from a low frequency to a high frequency. In other embodiments, individual chirps may continuously sweep down from a high frequency to a low frequency, from a low frequency to a high frequency, and back to a low frequency, or from a high frequency to a low frequency and back to a high frequency. In some embodiments, the low frequency is 58 GHz and the high frequency is 63.5 GHz. (For such frequencies, the radio waves may be referred to as millimeter waves.) In some embodiments, the frequencies are between 57 and 64 GHz. The low frequency and the high frequency may be varied by embodiment. For instance, the low frequency and the high frequency may be between 45 GHz and 80 GHz. The frequencies select may be selected at least in part to comply with governmental regulation. In some embodiments, each chirp includes a linear sweep from a low frequency to a high frequency (or the reverse). In other embodiments, an exponential or some other pattern may be used to sweep the frequency from low to high or high to low.

Chirp 250, which can be representative of all chirps in chirp timing diagram 200C, may have chirp duration 252 of 128 μs. In other embodiments, chirp duration 252 may be longer or shorter, such as between 50 μs and 1 ms. In some embodiments, a period of time may elapse before a subsequent chirp is emitted. Inter-chirp pause 256 may be 205.33 μs. In other embodiments, inter-chirp pause 256 may be longer or shorter, such as between 10 μs and 1 ms. In the illustrated embodiment, chirp period 254, which includes chirp 250 and inter-chirp pause 256, may be 333.33 μs. This duration varies based on the selected chirp duration 252 and inter-chirp pause 256.

A number of chirps that are output, separated by inter-chirp pauses may be referred to as frame 258 or frame 258. Frame 258 may include twenty chirps. In other embodiments, the number of chirps in frame 258 may be greater or fewer, such as between 1 and 100. The number of chirps present within frame 258 may be determined based upon a maximum amount of power that is desired to be output within a given period of time. The FCC or other regulatory agency may set a maximum amount of power that is permissible to be radiated into an environment. For example, a duty cycle requirement may be present that limits the duty cycle to less than 10% for any 33 ms time period. In one particular example in which there are twenty chirps per frame, each chirp can have a duration of 128 us, and each frame being 33.33 ms in duration. The corresponding duty cycle is (20 frames)*(0.128 ms)/(33.33 ms), which is about 7.8%. By limiting the number of chirps within frame 258 prior to an inter-frame pause, the total amount of power output may be limited. In some embodiments, the peak EIRP (effective isotropically radiated power) may be 13 dBm (20 mW) or less, such as 12.86 dBm (19.05 mW). In other embodiments, the peak EIRP is 15 dBm or less and the duty cycle is 15% or less. In some embodiments, the peak EIRP is 20 dBm or less. That is, at any given time, the amount of power radiated by the radar subsystem might never exceed such values. Further, the total power radiated over a period of time may be limited.

Frames may be transmitted at a frequency of 30 Hz (33.33 ms) as shown by time period 260. In other embodiments, the frequency may be higher or lower. The frame frequency may be dependent on the number of chirps within a frame and the duration of inter-frame pause 262. For instance, the frequency may be between 1 Hz and 50 Hz. In some embodiments, chirps may be transmitted continuously, such that the radar subsystem outputs a continuous stream of chirps interspersed with inter-chirp pauses. Tradeoffs can be made to save on the average power consumed by the device due to transmitting chirps and processing received reflections of chirps. Inter-frame pause 262 represents a period of time when no chirps are output. In some embodiments, inter-frame pause 262 is significantly longer than the duration of frame 258. For example, frame 258 may be 6.66 ms in duration (with chirp period 254 being 333.33 μs and 20 chirps per frame). If 33.33 ms occur between frames, inter-frame pause 262 may be 26.66 ms. In other embodiments, the duration of inter-frame pause 262 may be larger or smaller, such as between 15 ms and 40 ms.

In the illustrated embodiment of FIG. 2C, a single frame 258 and the start of a subsequent frame are illustrated. It should be understood that each subsequent frame can be structured similarly to frame 258. Further, the transmission mode of the radar subsystem may be fixed. That is, regardless of whether a user is present or not, the time of day, or other factors, chirps may be transmitted according to chirp timing diagram 200C. Therefore, in some embodiments, the radar subsystem always operates in a single transmission mode, regardless of the state of the environment or the activity attempting to be monitored. A continuous train of frames similar to frame 258 may be transmitted while device 101 is powered on.

Figure 3A:
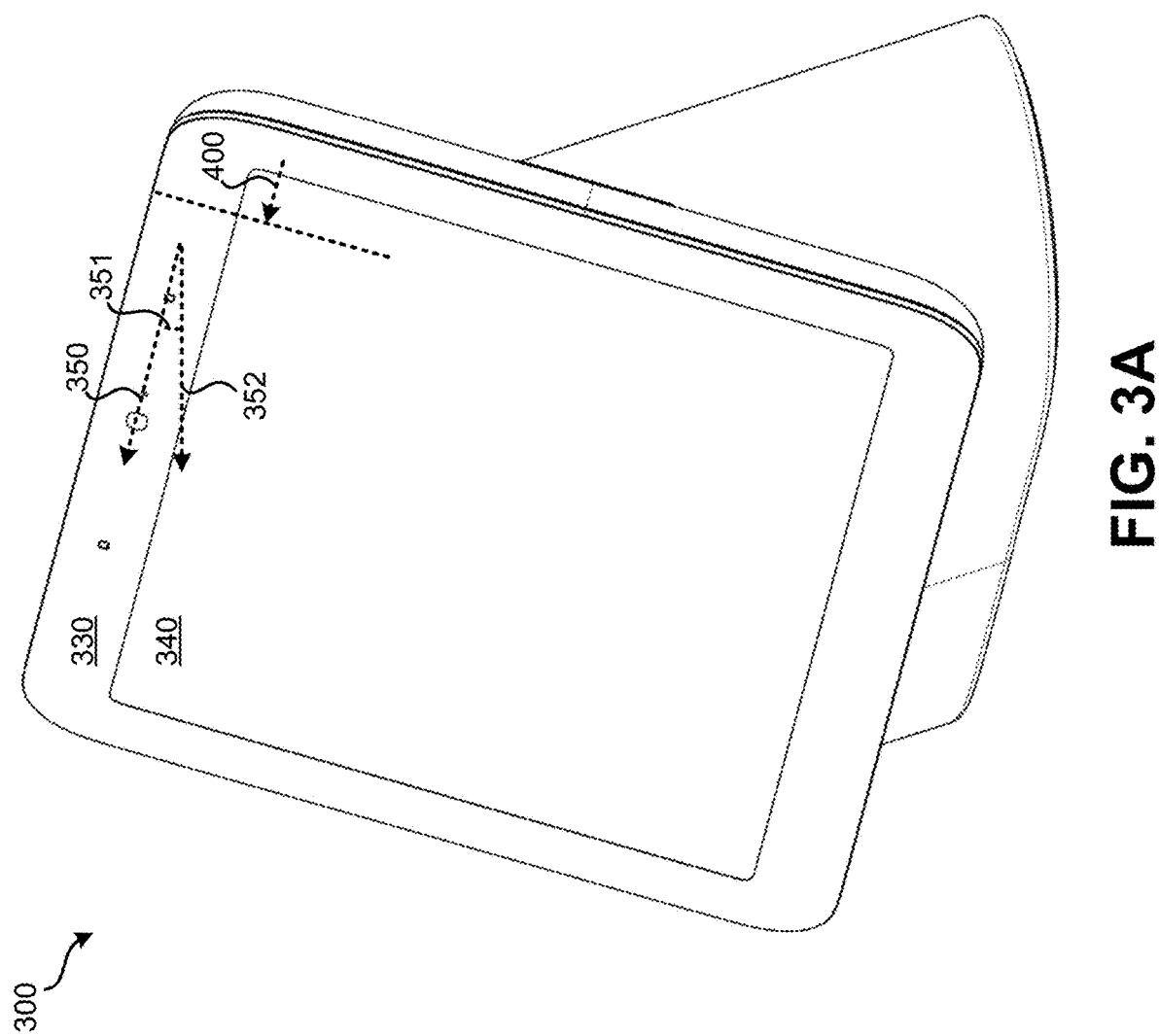
FIG. 3A illustrates an embodiment of a contactless sleep tracking device.

FIG. 3A illustrates an embodiment of a contactless sleep tracking device 300 ("device 300"). Device 300 may have a front surface that includes a front transparent screen 340 such that a display is visible. Such a display may be a touchscreen. Surrounding front transparent screen 340 may be an optically-opaque region, referred to as bezel 330, through which radar subsystem 205 may have a field-of-view of the environment in front of device 300. Cross-section view 400 is detailed in relation to FIG. 4.

For purposes of the immediate following description, the terms vertical and horizontal describe directions relative to the bedroom in general, with vertical referring to a direction perpendicular to the floor and horizontal referring to a direction parallel to the floor. Since the radar subsystem, which may be an Infineon® BGT60 radar chip, is roughly planar and is installed generally parallel to bezel 330 for spatial compactness of the device as a whole, and since the antennas within the radar chip lie in the plane of the chip, then, without beam targeting, a receive beam of radar subsystem 120 may be pointed in direction 350 that is generally normal to bezel 330. Due to a departure tilt of bezel 330 away from a purely vertical direction, which is provided in some embodiments to be about 25 degrees in order to facilitate easy user interaction with a touchscreen functionality of the transparent screen 340, direction 350 may point upwards from horizontal by departure angle 351. Assuming device 300 will typically be installed on a bedside platform (e.g., nightstand) that is roughly the same height as the top of a mattress on which a user will sleep, it may be beneficial for the receive beam of radar subsystem 120 to be targeted in horizontal direction 352 or an approximately horizontal (e.g., between −5° and 5° from horizontal) direction. Therefore, vertical beam targeting can be used to compensate for departure angle 351 of the portion of device 300 in which radar subsystem 120 is present.

FIG. 3B illustrates an exploded view of an embodiment of contactless sleep tracking device 300. Device 300 can include: display assembly 301; display housing 302; main circuit board 303; neck assembly 304; speaker assembly 305; base plate 306; mesh network communication interface 307; top daughterboard 308; button assembly 309; radar assembly 310; microphone assembly 311; rocker switch bracket 312; rocker switch board 313; rocker switch button 314; Wi-Fi assembly 315; power board 316; and power bracket assembly 317. Device 300 can represent an embodiment of how device 101 may be implemented.

Display assembly 301, display housing 302, neck assembly 304, and base plate 306 may collectively form a housing that houses all of the remaining components of device 300. Display assembly 301 may include an electronic display, which can be a touchscreen, that presents information to a user. Display assembly 301 may, therefore, include a display screen, which can include a metallic plate of the display that can serve as a grounding plane. Display assembly 301 may include transparent portions away from the metallic plate that allow various sensors a field of view in the general direction in which display assembly 301 is facing. Display assembly 301 may include an outer surface made of glass or transparent plastic that serves as part of the housing of device 300.

Display housing 302 may be a plastic or other rigid or semi-rigid material that serves as a housing for display assembly 301. Various components, such as main circuit board 303; mesh network communication interface 307; top daughterboard 308; button assembly 309; radar assembly 310; and microphone assembly 311 may be mounted on display housing 302. Mesh network communication interface 307; top daughterboard 308; radar assembly 310; and microphone assembly 311 may be connected to main circuit board 303, using flat wire assemblies. Display housing may be attached with display assembly 301, using an adhesive.

Mesh network communication interface 307 may include one or more antennas and may enable communication with a mesh network, such as a Thread-based mesh network. Wi-Fi assembly 315 may be located a distance from mesh network communication interface 307 to decrease the possibility of interference. Wi-Fi assembly 315 may enable communication with a Wi-Fi based network.

Radar assembly 310, which can include radar subsystem 120 or radar subsystem 205, may be positioned such that its RF emitter and RF receiver are away from the metallic plate of display assembly 301 and are located a significant distance from mesh network communication interface 307 and Wi-Fi assembly 315. These three components may be arranged in approximately a triangle to increase the distance between the components and decrease interference. For instance, in device 300, a distance of at least 74 mm between Wi-Fi assembly 315 and radar assembly 310 may be maintained. A distance of at least 98 mm between mesh network communication interface 307 and radar assembly 310 may be maintained. Additionally, distance between radar assembly 310 and speaker 318 may be desired to minimize the effect of vibrations on radar assembly 310 that may be generated by speaker 318. For instance, for device 300, a distance of at least 79 mm between radar assembly 310 and speaker 318 may be maintained. Additionally, distance between the microphones and radar assembly 310 may be desired to minimize any possible interference from the microphones on received radar signals. Top daughterboard 308 may include multiple microphones. For instance, at least 12 mm may be maintained between a closest microphone of top daughterboard 308 and radar assembly 310.

Other components may also be present. A third microphone assembly may be present, microphone assembly 311, which may be rear-facing. Microphone assembly 311 may function in concert with the microphones of top daughterboard 308 to isolate spoken commands from background noise. Power board 316 may convert power received from an AC power source to DC to power the components of device 300. Power board 316 may be mounted within device 300 using power bracket assembly 317. Rocker switch bracket 312, rocker switch board 313, and rocker switch button 314 may be collectively used to receive user input, such as up/down input. Such input may be used, for example, to adjust a volume of sound output through speaker 318. As another user input, button assembly 309 may include a toggle button that a user can actuate. Such a user input may be used to activate and deactivate all microphones, such as for when the user desires privacy and/or does not want device 300 to respond to voice commands.

Figure 4:
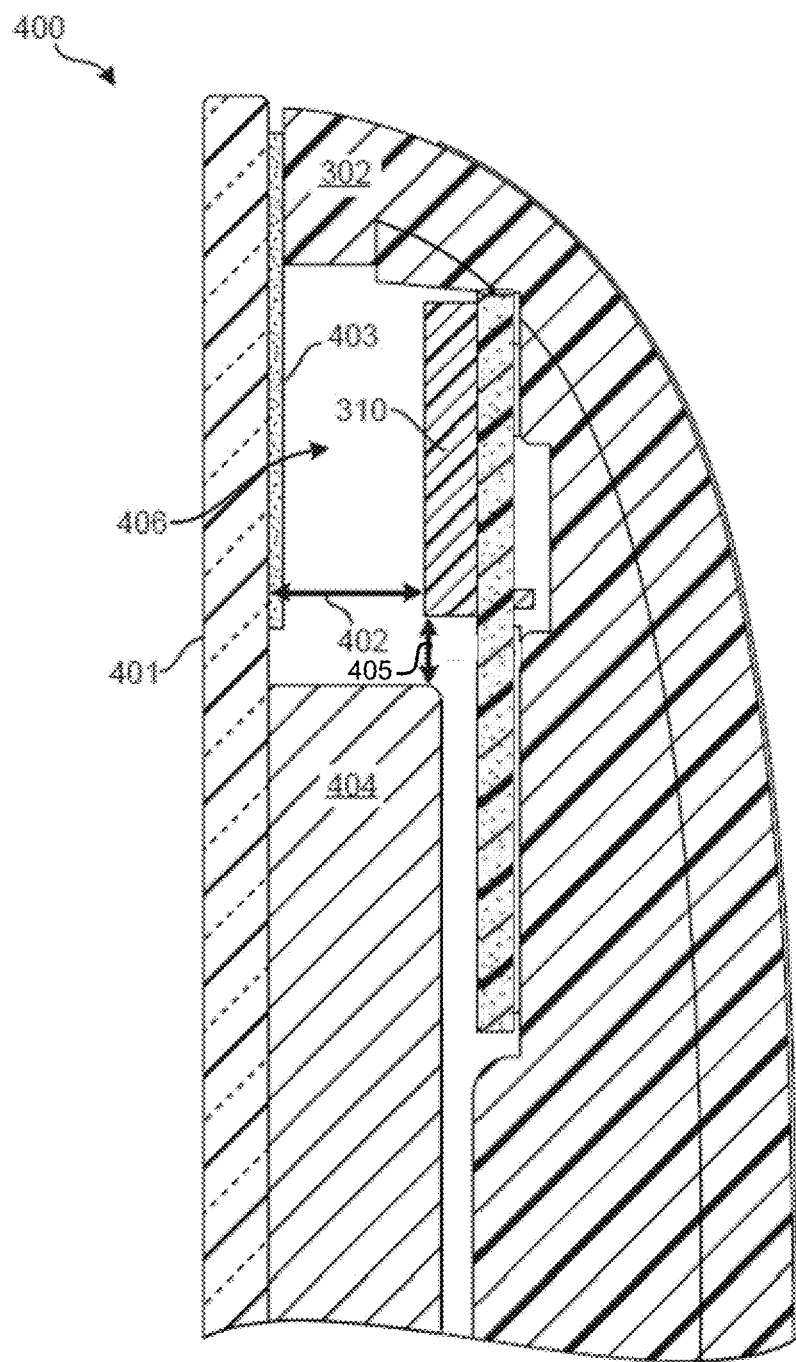
FIG. 4 illustrates a cross-sectional view of a contactless sleep tracking device.

FIG. 4 illustrates a cross-sectional view of device 300. Screen 401, which may be glass or plastic, may be attached to display housing 302, such as by using adhesive 403. Screen 401 and metallic housing 404 may be part of display assembly 301. Between radar assembly 310 and screen 401 may be air gap 406. Radar assembly 310 may be mounted such that a minimum amount of undesirable reflection is caused by refractive index differences encountered by electromagnetic waves traveling outward from the radar assembly 310 and through the front of device 300. Distance 402 may be between 2 and 2.3 mm, which corresponds to somewhat less than half of a free-space wavelength of 5 mm at 60 GHz, which may be about the frequency of RF signals output by the RF emitter of radar assembly 310. By the distance corresponding to somewhat less (or more) than a half wavelength, an anti-cavity is created. If exactly a half wavelength distance is used, constructive interference may be present, which can be avoided to prevent unwanted reflected signals from being received. Additionally, a significantly larger or smaller air gap size can be used to ensure constructive interference does not occur. Adhesive 403 may be considered to have little to no effect on radar reflections.

Distance 405 may be at least 1 mm, such as 1.2 mm. The farther radar assembly 310 is separated from metallic housing 404, the less interference may be caused by metallic housing 404 on emitted and received RF by metallic housing 404. A ground of radar assembly 310 may be connected with metallic housing 404 such that radar assembly 310 uses metallic housing 404 as a ground plane.

Figure 5:
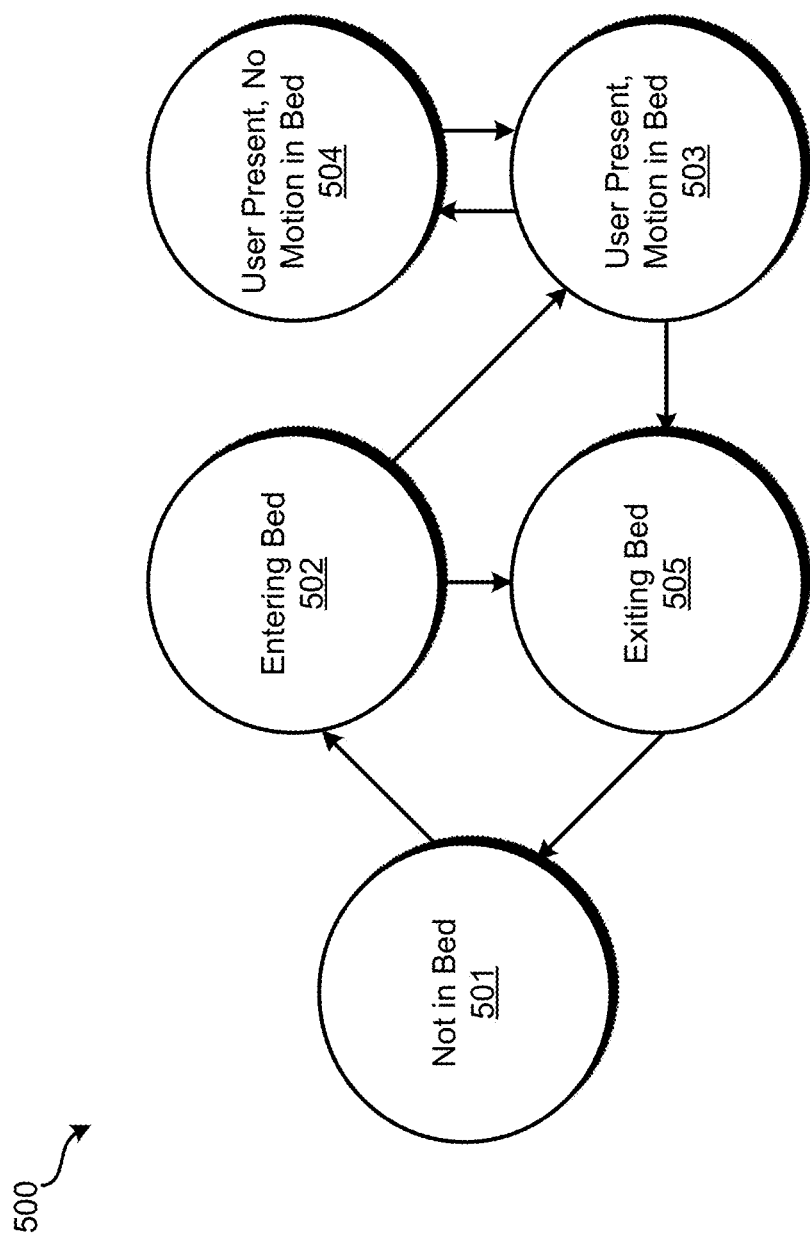
FIG. 5 illustrates an embodiment of a state machine for determining when a person is sleeping.

FIG. 5 illustrates an embodiment of a state machine 500 for determining when a person is sleeping. Based upon data output by radar processing module 112, sleep state detection engine 114 may determine whether a person is sleeping using state machine 500. It should be understood that in some embodiments, sleep state detection engine 114 is incorporated as part of the functionality of radar processing module 112 and does not exist as a separate module. State machine 500 may include five possible sleep states: entering bed state 501; not in bed state 502; motion in bed state 503; no motion in bed state 505; and exiting bed state 504.

If no motion-indicative waveform data is present, this may be indicative that the user is not in bed. A user who is in bed can be expected to always be moving in at least small amounts due to their vital signs. Therefore, if zero movement is observed, the user may be judged to be in state 501. Following state 501 being determined, the next possible state that may be determined is state 502. In state 502, the monitored user is entering bed. Significant user motion may be sensed, such as according to Table 2. This may be indicative of a user entering bed and may cause the state to transition from state 501 to state 502.

From state 502, motion may continue to be detected in bed, such as due to the user rolling around, getting positioned, moving pillows, sheets, and/or blankets, reading a book, etc. State 502 may transition to state 503 while such motion continues to be detected. Alternatively, if motion is detected, then zero motion is detected, this may be indicative that state 505 has been entered by the monitored user exiting bed. If this condition occurs, state 502 may transition to state 505, then back to state 501. Generally, state 504 may be interpreted as the user being asleep and state 503 may be interpreted as the user being awake. In some embodiments, more than a threshold amount of time (or some other form of determination that uses a form of threshold criterion at least partially based on time) in state 504 is necessary to classify the user as asleep and more than a threshold amount of time (or some other form of determination that uses a form of threshold criterion at least partially based on time) in state 503 is necessary to classify the user as awake. For instance, movement in bed of less than five seconds may be interpreted as the user moving while still asleep if the user was previously determined to be asleep. Therefore, if a user transitions to state 503 from state 504, experiences some number of movement events, then returns to state 504 within less than a duration of time, the user may be identified as having experienced a "sleep arousal" in which the user's sleep is disturbed, but the user has not been awoken. Such sleep arousals may be tracked together with or separate data may be maintained from episodes where the user is judged to have fully awoken.

From state 503, the monitored user may be determined to be exiting bed at state 505 and may become motionless at state 504. To be "motionless" at state 504 refers to no large movements being performed by the monitored user, but the user continuing to perform small motions due to vital signs. In some embodiments, only when the monitored user's state is determined to be state 504 are vital signs treated as accurate and/or stored, recorded, or otherwise used to measure the user's vital signs. Data collected during state 503 and state 504 may be used to determine the monitored user's general sleep patterns (e.g., how much time tossing and turning, how much quality sleep, when deep sleep occurred, when REM sleep occurred, etc.). After a user enters state 504 for a predefined period of time, the user may be assumed to be asleep until the user exits state 504. When a user initially transitions to state 504, the user may be required to stay in state 504 for some amount of time, such as two to five minutes, to be considered asleep. If a user is in state 503 for at least a defined period of time, the user may be identified as awake. However, if the user enters state 503 from state 504 for less than the defined period of time, and returns to state 504, the user may be identified as just moving within their sleep and has been continuously asleep.

Figure 6:
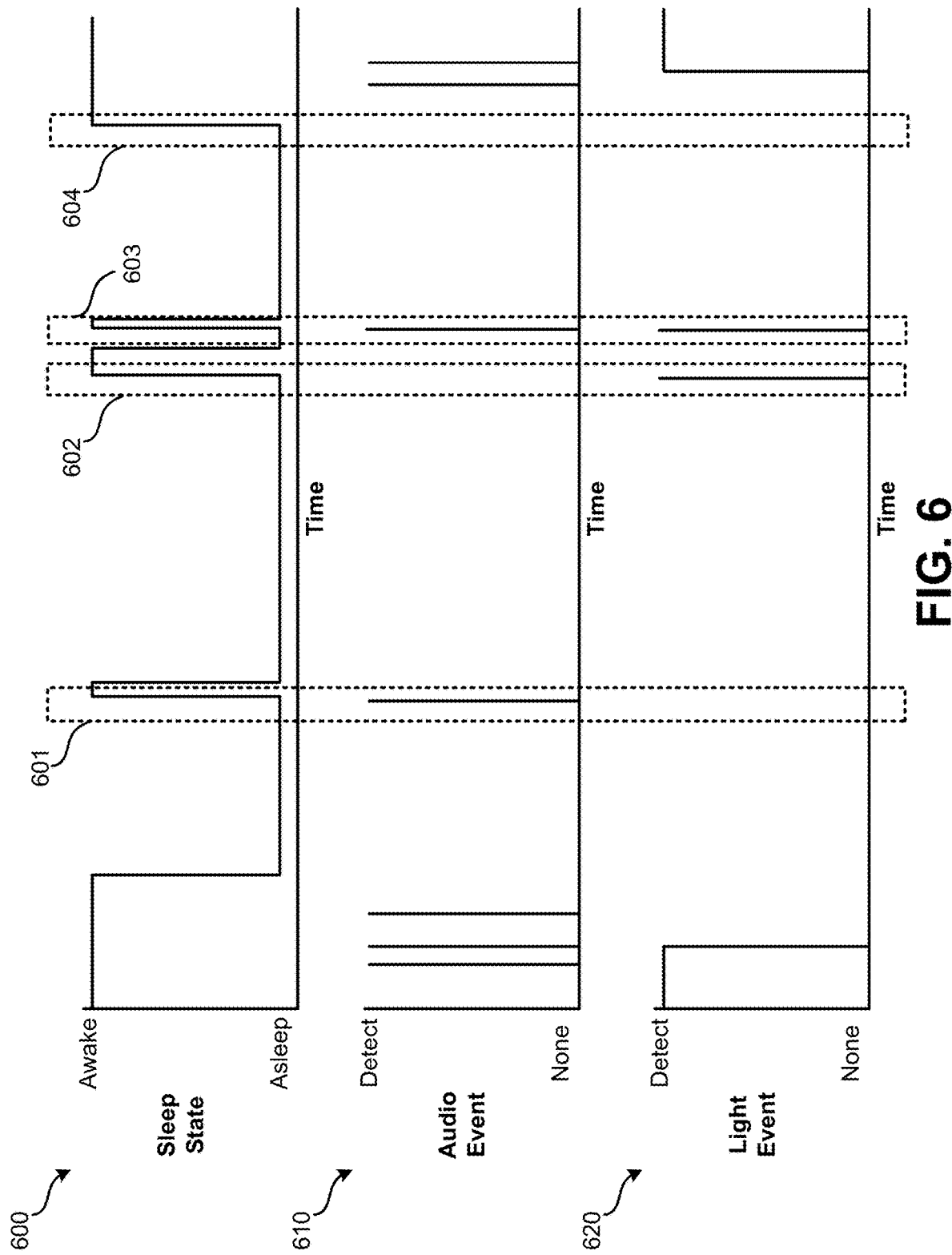
FIG. 6 illustrates timelines of detected sleep states and environmental disturbances.

FIG. 6 illustrates timelines of detected sleep states and environmental disturbances. Sleep timeline 600 illustrates when a user is determined to be awake or asleep, such as according to state machine 500. Audio timeline 610 illustrates when an environmental audio event is detected by device 101. Light timeline 620 illustrates when an environmental light event is detected by device 101. In the example of FIG. 6, device 101 monitors audio and light. In other embodiments, device 101 may monitor audio or light. In still other embodiments, one or more additional environmental conditions may be monitored, such as temperature or movement of other living things (e.g., using a PIR sensor). A sound event may be detected if: 1) a detected amount of sound in the environment exceeds a fixed sound level threshold (or some other form of determination that uses a threshold criterion at least partially based on sound); or 2) the ambient sound level increases by more than a defined threshold amount or percentage (or some other form of determination that uses a threshold criterion at least partially based on sound). A light event may be detected if: 1) a detected amount of light exceeds a fixed light threshold; or 2) the ambient lighting level increases by more than a defined threshold amount or percentage (or some other form of determination that uses a threshold criterion at least partially based on lighting level). A similar analysis may be performed for temperature. For movement monitoring, if another living object is detected moving within the room, an event may be recorded as detected.

A time may be recorded each time a user transitions from being asleep to awake. For each detected audio event and each detected light event, a time may also be recorded and mapped to the environmental event. To determine if a sleep event (e.g., a transition from asleep to awake) likely corresponds to an environmental event, if the environmental event occurs with a time window around the sleep event, the sleep event may be interpreted as having been caused by the environmental event. In some embodiments, the time window precedes the sleep event by a fixed amount of time, such as five seconds. In some embodiments, the time window additionally trails the sleep event by a fixed amount of time, which can be shorter than the preceding time, such as by two seconds. In order for the environmental event to cause the user to awaken, the environmental event would logically have to proceed the user waking. However, due to variances in the detection, processing, and/or analysis of audio, light, temperature, or other factors, it may be accurate to have a trailing time period after the sleep event during which, if the environmental event is determined to have occurred, the environmental event is "blamed" for waking the user. As an example, if significant change in temperature is detected shortly after the user awakes, it may be likely that it took time for the temperature shift to be detected and the user was awoken by the temperature change.

In the example of FIG. 6, during time period 601, a user is detected as transitioning from asleep to awake. During time period 601, an audio event is detected, but no light event. Since the audio event is within the defined time period around the sleep event, the user awaking is attributed to the detected audio event. During time period 602, a light event is detected but no audio event. Since the light event is within the defined time period around the sleep event, the user awaking is attributed to the detected light event. During time period 603, a light event and an audio event are detected. Since the light event and audio event are within the defined time period around the sleep event, the user awaking is attributed to both the detected light and audio events. During time period 604, no environmental event is detected. Since no environmental event is within the defined time period around the sleep event, the user awaking is not attributed to any environmental event.

The data used to indicate the timelines may be used to provide the user with a nightly report of sleep. For instance, when requested by the user or at a defined time in the morning, a graphical or textual report may be presented that indicates: 1) when a user awoke during the night; 2) what environmental events were detected; and 3) instances of waking that were attributed to an environmental event.

If multiple users are present within a same bed, movement of a first user may be the environmental factor that wakes the second user. Therefore, if a first user is detected as in state 503, and the other user is determined to wake within a time window of the first user entering state 503, the first user may be the environmental factor for waking the second user.

Figure 7:
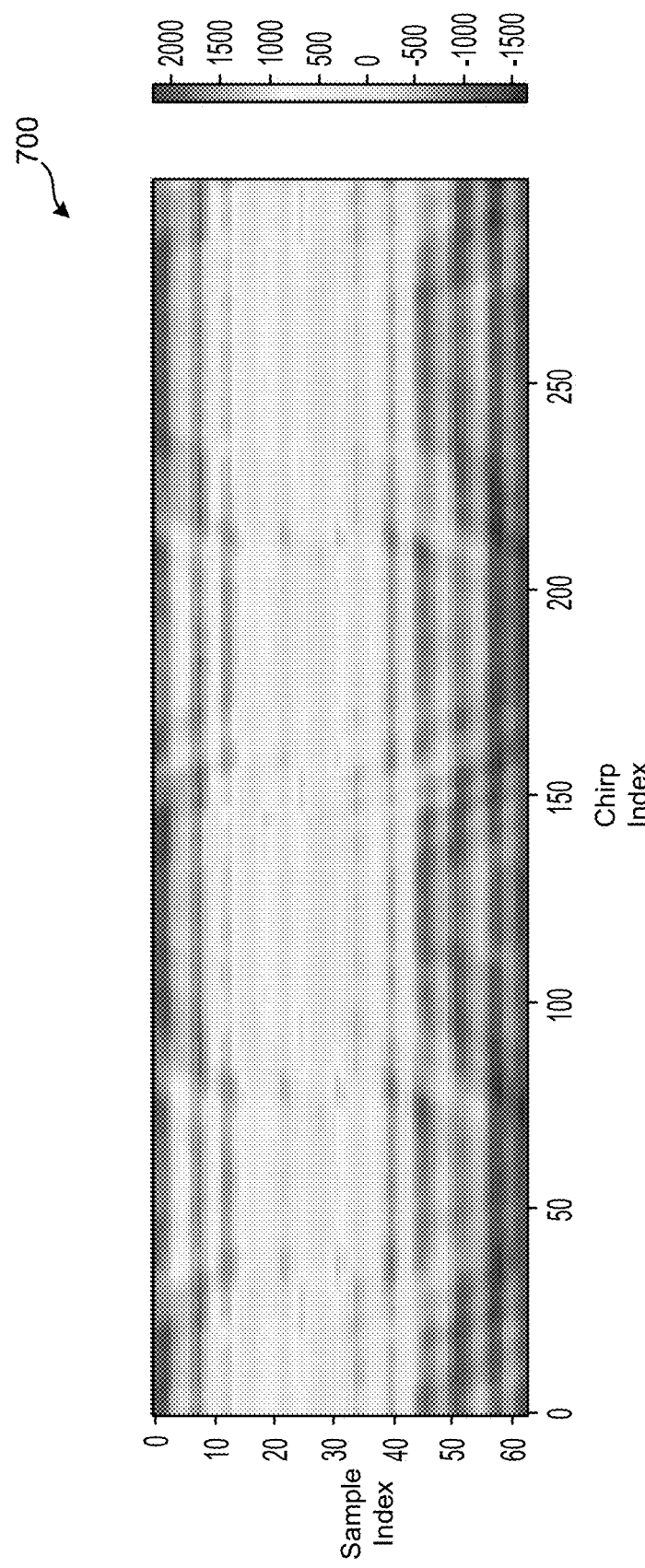
FIG. 7 illustrates an embodiment of waveform data in which movement due to vital signs of a user are observable.

FIG. 7 illustrates an embodiment of raw waveform data or raw chirp waterfall data in which movement due to vital signs of a user is observable. Embodiment 700 represents raw waveform data (which can also be referred to as raw chirp waterfall data) output by radar subsystem 205. Along the x-axis, a chirp index is indicated. This chirp index indicates an arbitrary identifier for the particular chirp corresponding to the data arranged along the y-axis and the RF intensity data, indicated by the shading. The scale of shading represents normalized values that can be output by the ADC of radar subsystem 205. Along the y-axis, a sample index is indicated. For each chirp indicated along the x-axis, a number of samples are measured at a time interval. For instance, sixty-four samples may be measured for each chirp. The RF intensity of the reflected radio waves may be measured at each sample index.

Embodiment 700 is representative of device 101 being aimed at a monitored sleeping user who is generally still from a distance of less than one meter. In embodiment 700, slight "waves" are visible over time in the raw waveform data due to the user's chest and/or abdomen rising and falling thereby effecting the reflection of the radio waves. The frequency of these relatively slow movements can be measured over time to determine a frequency of the user's vital signs. In the illustrated embodiment, the visible waves are caused by the user's breathing pattern at approximately 13.5 breaths per minute.

In addition to the visible waves, a significant amount of the RF intensity is due to reflections by static objects. For example, at sample index 64, regardless of the chirp index, the RF intensity remains high, possibly due to reflection by a large object, such as a wall. Such static reflections can be filtered out by movement filter 211 prior to other signal processing.

Figure 8:
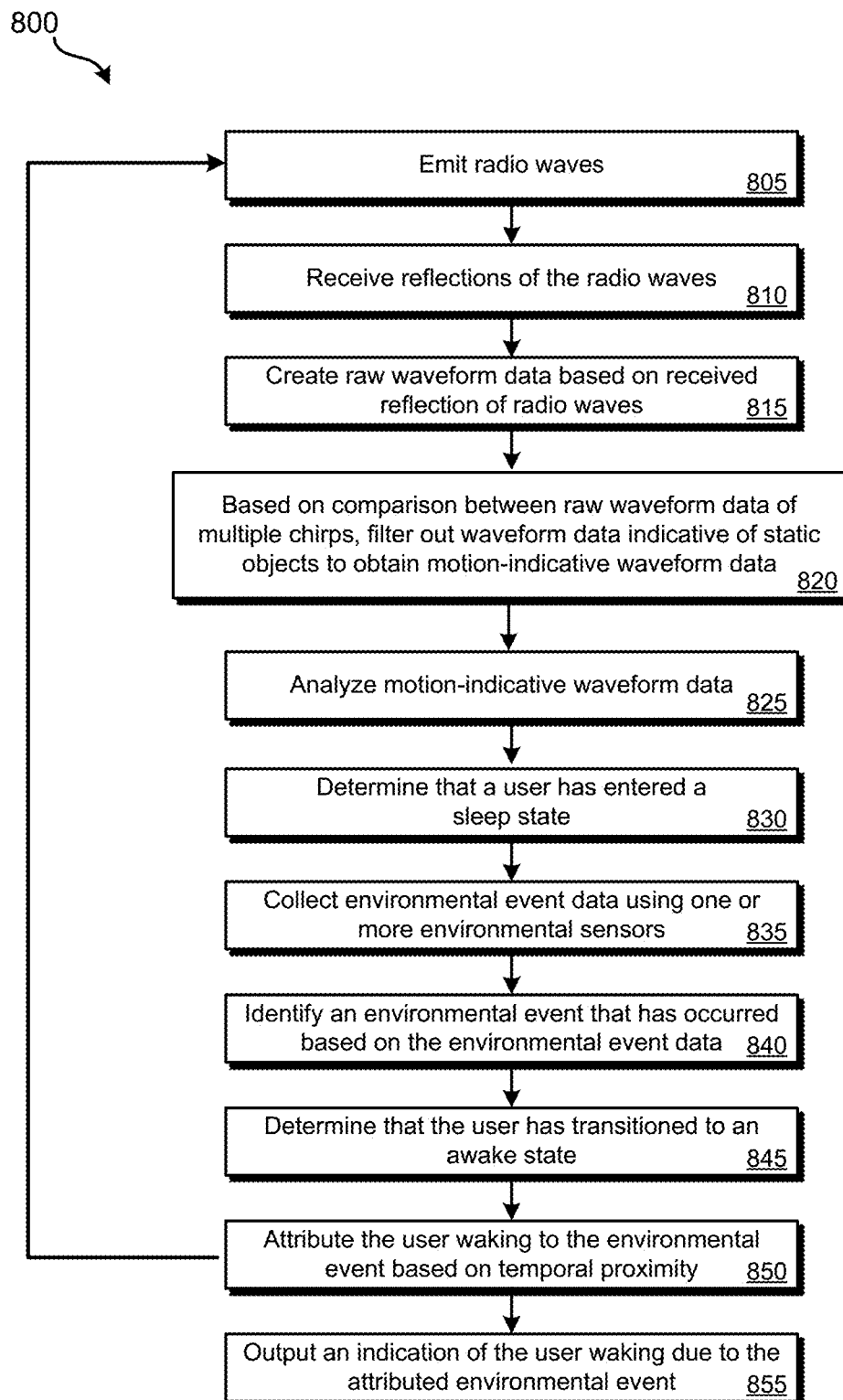
FIG. 8 illustrates an embodiment of a method for performing contactless sleep detection and disturbance attribution.

Various methods may be performed using the systems, devices, and arrangements detailed in relation to FIGS. 1-7. FIG. 8 illustrates an embodiment of a method 800 for performing contactless sleep detection and disturbance attribution. Method 800 may be performed using system 100, system 200A, device 300, or some other form of system that can transmit, receive, and analyze radar, such as an FMCW radar.

At block 805, radio waves are emitted. The radio waves emitted may be continuous-wave radar, such as FMCW. The radio waves emitted at block 805 may be emitted in accordance with the FMCW radar scheme of FIG. 2C. The radio waves emitted may be emitted by RF emitter 206 of radar subsystem 205. At block 810, reflections of the radio waves are received, such as by RF receiver 207 of radar subsystem 205. The reflections received at block 810 may be reflected off of moving objects (e.g., a person having a heartbeat and breathing) and stationary objects. A phase shift may be present in the radio waves reflected by a moving object. For each FMCW chirp emitted at block 805, a number of samples may be measured of reflected RF intensity, such as 64 samples. Fewer or greater numbers of samples may be measured in other embodiments.

At block 815, raw waveform data, which can also be referred to as the raw chirp waterfall data, may be generated based on received reflected radio waves. A mixed signal generated by mixing the reflected radio waves with the transmitted radio waves may be indicative of distance and a phase shift. For each of these samples, intensity and phase shift may be measured. Over time, a window of raw waveform data may be created and stored in a buffer for analysis. Referring to FIG. 2, block 815 may be performed by radar processing module 210.

At block 820, samples of the waveform data that have been buffered may be compared. Waveform data that is indicative of static objects (that is, zero phase shift), which can be defined as objects having movement below a particular frequency (or at least a threshold phase shift or some other form of determination that uses a threshold criterion at least partially based on phase shift), may be filtered out and discarded such that waveform data that is indicative of movement above a particular frequency is saved for further analysis. Block 220 may be performed before block 825 to remove a large portion of the waveform data attributed to static objects and more readily make data attributed to movements of a user detectable.

At block 825, the motion-indicative waveform data may be analyzed. This analysis may be performed to identify and separate data attributable to user motion, heartrate, and breathing rate. Detail regarding how the motion-indicative waveform data may be analyzed is detailed in relation to the components of radar processing module 210. That is, processing using movement filter 211, frequency emphasizer 212, range-vitals transform engine 213, range gating filter 214, spectral summation engine 215, and neural network 216 may be performed in order to produce data to be analyzed to determine the user's sleep state and, possibly, the user's vital statistics.

At block 830, a sleep state of a user may be determined, such as using the state machine of FIG. 5. Based upon an output from the radar processing module, a sleep state detection engine may determine whether a user is likely asleep (e.g., no significant motion within bed, but vital statistics detected) or awake (e.g., major motion detected within bed). At block 835, a determination may be made that a user has entered a sleep state based on the analyzed radar data.

While the user is in the sleep state, one or more environmental sensors may be active and gathering data that is provided to a processing system. The environmental conditions may be monitored to determine if an environmental event occurs. Such environmental conditions can include one or more of: light, sound, temperature, smell, movement, etc. These environmental conditions may be monitored constantly or periodically while the user is asleep (e.g., following block 830). In some embodiments, the device performing method 800 may perform such monitoring constantly regardless of whether the user is detected as present (and asleep) or absent.

At block 840, a determination that an environmental event has occurred may be made based on environmental data obtained from the one or more environmental sensors. At block 840, data from each environmental sensor device may be monitored for: 1) an increase of the environmental condition above a fixed defined threshold (or some other form of determination that uses a threshold criterion); and/or 2) an increase in the environmental condition by at least a predefined amount or percentage. If either of these events occurs, an environmental event is identified as having occurred. An indication of the environmental event may be stored in association with a timestamp. At block 845, while environmental conditions are being monitored, the user is determined to transition from sleep to awake. Referring to state machine 500, this determination can involve the state machine being in state 503 for at least a predetermined amount of time.

At block 850, the user being determined to have entered the awake state from the sleep state at block 845 is attributed to the environmental event identified at block 840 based on the environmental event occurring within a predefined time period of the user waking. The predefined time period may precede the time at which the user awakes, or may span from before the user wakes until after the user is identified as awake. The amount of time preceding the user awaking may be longer than the trailing time for the time period. In some embodiments, the time period varies in duration based on the specific type of environmental event (e.g., a temperature event may involve a longer trailing time than a sound event). When an environmental event is attributed with waking the user, data may be stored indicating the environmental event that caused the user to wake, when the event occurred, and/or how many times the type of environmental event has caused the user to awake over some period of time (e.g., the last week, the last month).

At block 855, an indication of the user waking one or more times due to one or more environmental events may be output to the user. This output can involve a report being presented to the user. The report may be for a particular night or for some other period of time, such as the previous week. If the number of times a specific type of environmental event has woken the user exceeds a defined threshold (or some other form of determination that uses a threshold criterion), the user may be presented with a recommendation to remedy the environmental event. In some embodiments, the user may receive an oral report via synthesized speech when the user is awake. In some embodiments, the user may be emailed a report periodically about their sleep (e.g., once per week).

Figure 9:
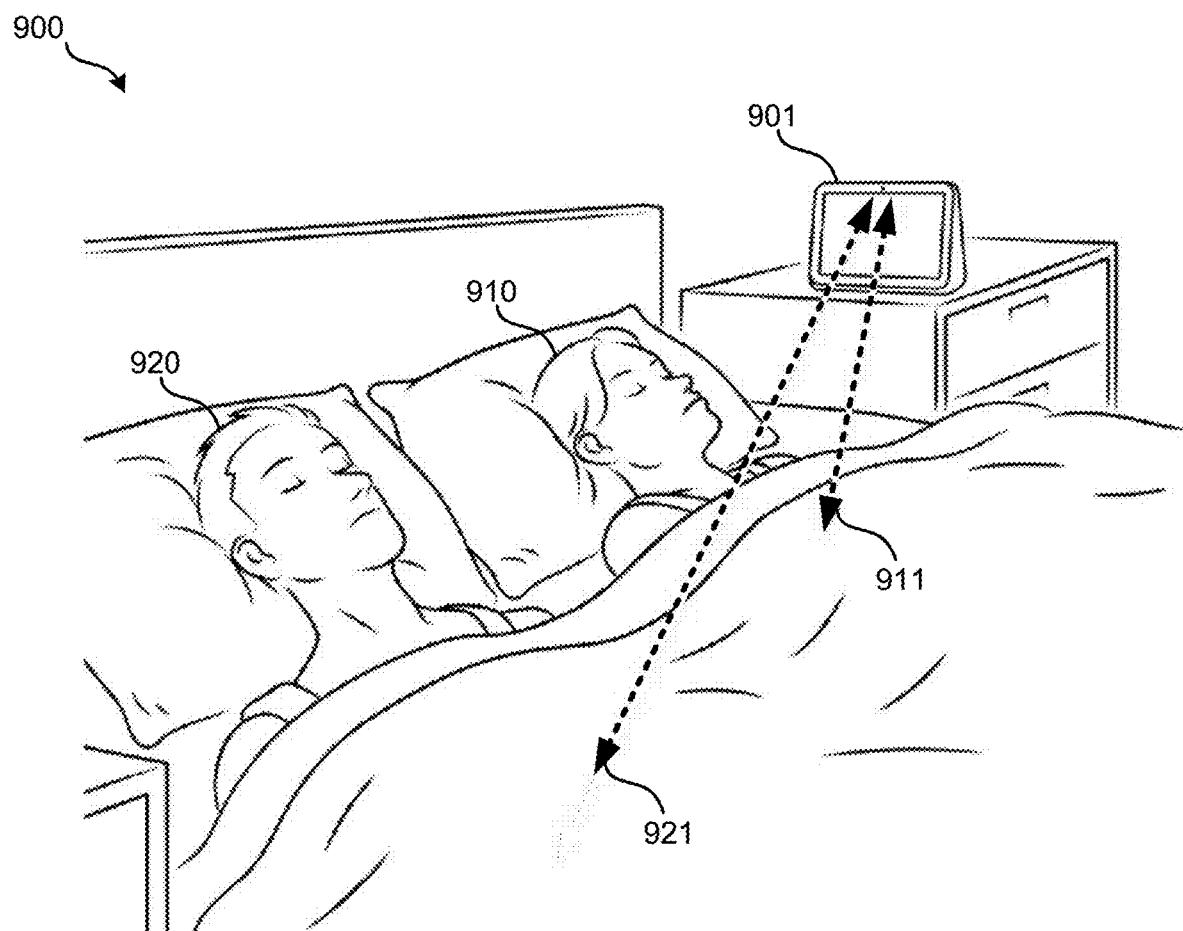
FIG. 9 illustrates an embodiment of a contactless sleep tracking device monitoring multiple users.

While the previous embodiments detailed in relation to the figures are primarily focused on monitoring the sleep of a single user, these same concepts can be applied to multiple users who are sleeping in close proximity to each other (e.g., within the same bed or within two beds having little to no space between them). FIG. 9 illustrates an embodiment 900 of a contactless sleep tracking device monitoring multiple users. Contactless sleep tracking device 901 ("device 901") can represent an embodiment of contactless sleep tracking device 101 of FIG. 1 and/or device 300 that is configured to monitor multiple users over a same time period. In embodiment 900, two users are present within a bed and are both having their sleep monitored by device 901. A different distance is present between user 910 and device 901 (distance 911) and user 920 and device 901 (distance 921).

While separate sleep data may be created and stored by device 901 for each user, user 910 and user 920 might not be in bed for exactly the same time period. For example, user 920 may go to bed earlier or later than user 910; similarly user 920 may get up from bed in the morning earlier or later than user 910. As a further example, user 910 or user 920 may temporarily leave bed in the middle of the night (e.g., for a bathroom visit) and subsequently return to bed. Therefore, when a user exits the bed, device 901 can continue to monitor sleeping for the other user that remains in bed. Device 901 can track which user has exited bed to ensure that sleep data remains attributed to the correct user despite one or more exits from and entries to bed.

Figure 10:
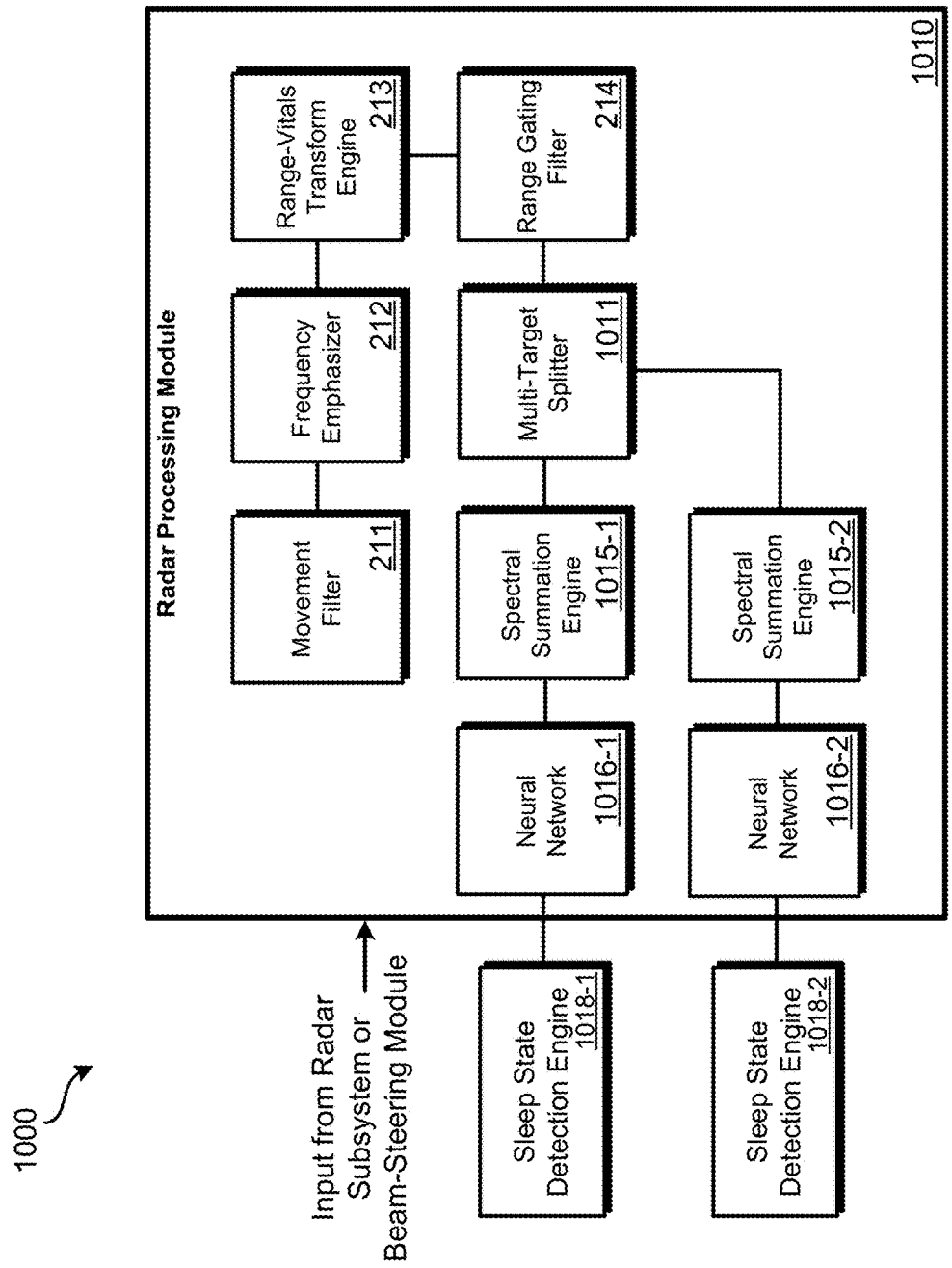
FIG. 10 illustrates an embodiment of a sleep tracking system that can track multiple users.

FIG. 10 illustrates an embodiment of a sleep tracking system 1000 that can track multiple users. System 1000 can function similarly to system 200A of FIG. 2. More specifically, radar subsystem 205 may be unchanged and beam-steering module 230 may be unchanged. For radar processing module 1010, several components may be unchanged from radar processing module 210: movement filter 211; frequency emphasizer 212; range-vitals transform engine 213; and range gating filter 214 may function as detailed in relation to device 200.

Radar processing module 1010 may additionally include multi-target splitter 1011. Multi-target splitter 1011 may serve to: identify the number of users present; and map data received from the radar subsystem (which can have been processed using movement filter 211, frequency emphasized 212, and/or range-vitals transform engine 213) to the associated user.

As an initial step, multi-target splitter 1011 may compress multi-dimensional data to fewer dimensions. Data received by multi-target splitter 1011 may have: a first dimension indicating a frequency of movement; a second dimension of distance from device 901; and/or a third dimension of intensity of movement. One or more of these dimensions may be eliminated to aid in a clustering process performed by multi-target splitter 1011. For instance, the dimension of movement frequency can be removed by using the sample having the greatest magnitude of movement frequency for a given distance. After such compressing, data may have two dimensions: a distance and a magnitude. This data may then be clustered.

Of note, distance can be represented in the multi-dimensional data by a single value. Therefore, only a distance from system 1000, regardless of direction, is tracked. The user, as part of an installation procedure, can be instructed to situate system 1000 to a side of the bed, such as on a nightstand. By system 1000 being to the side of a bed, two (or more) users lying side-by-side will have their corresponding movement detected at different distances. In other embodiments, rather than the data received by multi-target splitter 1011 having three dimensions, four or five dimensions may be present to capture a direction or precise location (e.g., 3D coordinates) of movement. By using such a greater number of dimensions related to location of movement, the user may be freed to situate system 1000 in any direction relative to the users.

Multi-target splitter 1011 may then be tasked with performing an unsupervised clustering process. The total number of users present is not known, so the process may need to determine the number of clusters. As previously discussed, while a user may have previously provided data that indicates two users desire their sleep data monitored, the users may enter and/or leave bed at different times. Therefore, at any given time, the data may need to be analyzed to identify whether one, two, or more than two users are present. In some embodiments, clustering may be restricted to filing a maximum of two clusters (that is, a restriction may be provided that no more than two people are monitored at a time).

To perform unsupervised clustering, multi-target splitter 1011 may perform a density-based clustering algorithm to the received data (which has been reduced by one or more dimensions). Density-based clustering may be performed using the density-based spatial clustering of applications with a noise (DBSCAN) algorithm. DBSCAN, given a set of points in a space, may group together points that are closely packed together (e.g., have many nearby neighbors). It should be understood that other forms of clustering besides the DBSCAN algorithm may be performed. Multi-target splitter 1011 may be initially configured with parameters for the DB SCAN algorithm, such as the minimum number of points required to form a dense region and the size of a point's neighborhood (typically represented by epsilon).

The output of the clustering process may be an indication of a number of clusters and a center location of each cluster (or a boundary of the cluster). To separate the clusters, a midpoint location between the two clusters may be located by multi-target splitter 1011. The midpoint may be calculated as the midpoint exactly between the locations output by the clustering algorithm. If three clusters are present (e.g., indicative of three users), two midpoints may be output, with each midpoint being the midpoint between two neighboring users.

Based on the location of the midpoint, a data set may be created for each user. Therefore, if two clusters are present (indicative of two users), the data received by multi-target splitter 1011 may be split into two datasets based on the location of the midpoint. Each dataset may subsequently be separately analyzed. Depending on the number of users (which is the same as the number of clusters), different instances of spectral summation engine 1015 (e.g., 1015-1, 1015-2) may be used to independently analyze the portion of the data output by range gating filter 214 mapped to each user. Each spectral summation engine of spectral summation engines 1015 may function as detailed in relation to spectral summation engine 215 for its respective received portion of data from range gating filter 214.

For instance, spectral summation engine 1015-1 may analyze the data determined by multi-target splitter 1011 as mapped to a first user and spectral summation engine 1015-2 may analyze the data determined by multi-target splitter 1011 as mapped to the second user. In some embodiments, there is no overlap in data sent to the separate spectral summation engines 1015. That is, data from range gating filter 214 is sent is separated into two datasets (for two users) and each dataset is sent to one of spectral summation engines 1015. If more than two users are present, a matching number of spectral summation engines 1015 may be present to process each data set and the number of datasets created matches the number of users detected.

For each user (and, therefore, for each cluster and instance of spectral summation engine 1015), a separate instance of neural network 1016 (or some other form of analysis engine) may be implemented (e.g., neural network 1016-1, 1016-2). Each instance of neural network 1016 may function similarly to neural network 216 for each set of data received from its corresponding spectral summation engine of spectral summation engines 1015. The output of each of neural networks 1016 may be output to a corresponding sleep state detection engine of sleep state detection engines 1018 (e.g., sleep state detection engine 1018-1, sleep state detection engine 1018-2). Each instance of sleep state detection engine 1018 may function similarly to sleep state detection engine 114. Therefore, for each user, their sleep state is monitored independently based on the data determined to correspond to that user by multi-target splitter 1011. When multiple users are identified, corresponding instances of a spectral summation engine, neural network, and sleep state detection engine may be instantiated for each detected user.

The output of each of sleep state detection engine 1018 may be stored and used similarly to what is detailed in relation to FIG. 1. That is, sleep data for each user may be mapped to the appropriate user. Therefore, times at which each user was asleep and awake may be stored such that a sleep report can be generated for each user individually (such as similar to sleep timeline 600).

Further, for each user, correlation between waking and environmental events may be performed separately. Referring to FIG. 6, a similar analysis may be performed for each individual user (based on the data mapped to the user by multi-target splitter 1011). For instance, an audio event may be attributed with waking a first user, but a second user may sleep through the audio event (and therefore the audio event would be attributed with waking the first user but not be attributed with waking the second user).

As an additional environmental event that may be monitored (e.g., in addition to light, sound, temperature, etc.), motion of other users may be attributed as an environmental factor causing a user to wake. As an example, movement of a first user (e.g., rolling over in bed while asleep, waking and getting out of bed) may be sensed using the radar sensor. If, within a sufficiently close time period of the first user moving, a second user wakes, the first user may be assigned the "blame" for waking the second user. In some embodiments, a determination of what is sufficiently close can be a defined time period. In this example, in a sleep report for the second user, the first user may be attributed for causing the second user to wake at a particular time. It may even be possible for environmental events to be chained together. For instance, an audio event may cause the first user to wake. Motion of the first user may then cause the second user to wake. If the two events (the audio event followed by the second user being woken by the motion of the first user) occur within a defined period of time, the waking of the second user may be attributed to the audio event or to the combination of the audio event and the movement of the first user.

Figure 11A:
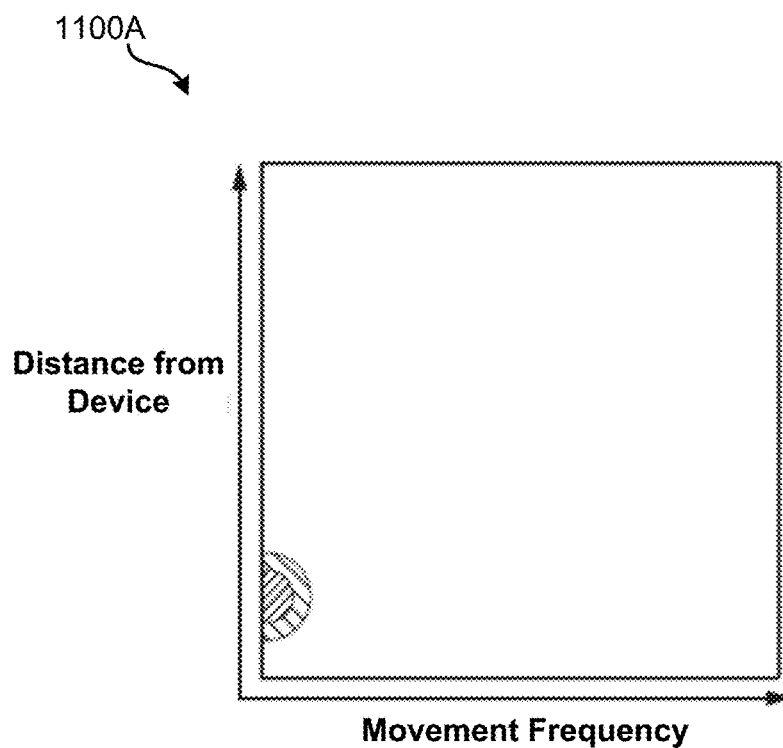
FIGS. 11A and 11B illustrate graphs of detected movement at various distances.
Figure 11B:
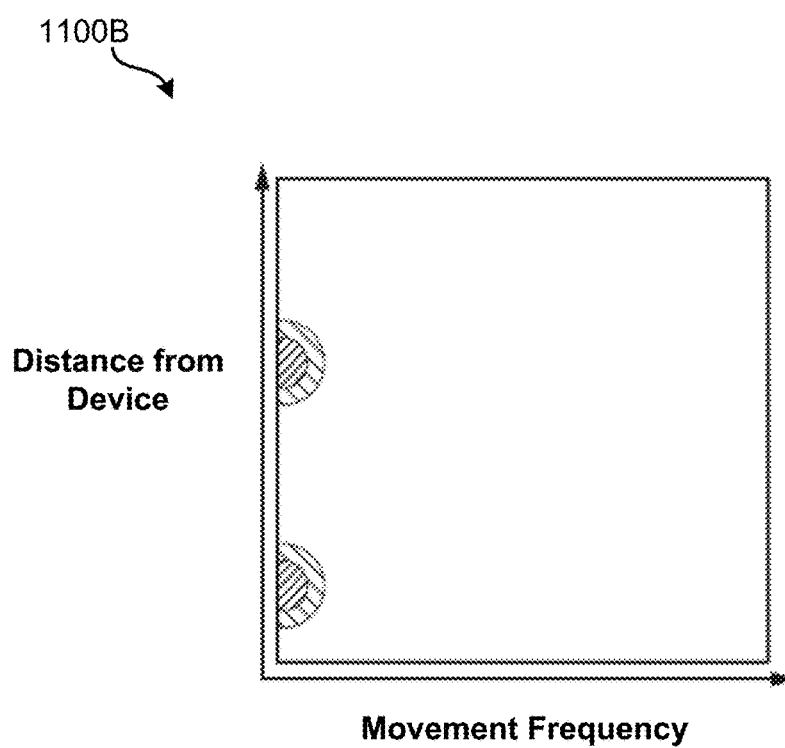

FIGS. 11A and 11B illustrate graphs of detected movement at various distances, such as detected by device 901. FIG. 11A is a graphical representation of data that can be received by multi-target splitter 1011. In a first dimension (e.g., y-axis), a distance at which movement is detected from the device is indicated. In a second dimension (e.g., x-axis), a frequency of detected movement may be indicated; in a third dimension (e.g., z-axis), a magnitude of movement may be indicated. In the illustrated graphs, magnitude (along the z-axis) is illustrated using shading. For example, a heartbeat may have a relatively high movement frequency but a small magnitude; and breathing may, at approximately the same distance, have a lower frequency, but a higher magnitude (such as because portions of the user's chest move more due to breathing than blood pumping).

As can be seen in graph 1110A of FIG. 11A, a single cluster of data is present. This arrangement is indicative of a single user being present within the detection range of device 901. However, in graph 1110B of FIG. 11B, two clusters are present at different distances. The frequency and magnitude of such data are similar, indicative of, for example, two different users breathing. Therefore, in graph 1110A, a single user is present in the detection range of the device 901 but for graph 1110B, two users are present in the detection range of device 901.

Figure 12:
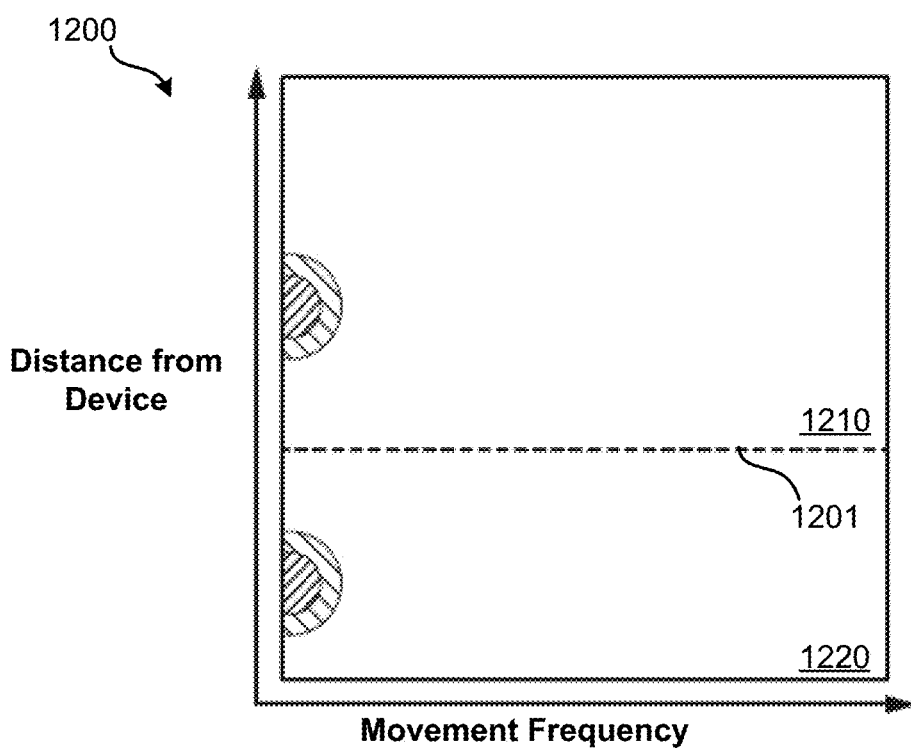
FIG. 12 illustrates a graph of detected movement being split into multiple targets.

FIG. 12 illustrates a graph 1200 of detected movement being split into multiple targets. Once the multi-target splitter has identified that two clusters are present and the locations of the two clusters, midpoint distance 1201 between the two locations may be determined. (As previously noted, the number of dimensions of the radar data may have been decreased; therefore, while graph 1200 indicates three dimensions, the multi-target splitter may have eliminated one or more dimensions, such as the movement frequency dimension. Therefore, the midpoint may be represented as a point on the y-axis.)

In graph 1200, motion represented in region 1210 may be attributed to a first user that is farther away from the device; motion represented in region 1220 may be attributed to a second user that is closer to the device. By monitoring such regions separately, two users can be monitored. If one of the clusters disappears, it may be indicative of the corresponding user exiting bed. The cluster that remains may be attributed to one of the users based on which side of midpoint distance 1201 the cluster is present. As long as a single cluster remains present, the single cluster may be attributed to the user for which the cluster was initially attributed based on which side of midpoint distance 1201 the cluster was detected. This may remain true even if the cluster migrates over midpoint distance 1201. As an example, consider if a first user exits bed. The second user may remain sleeping and may roll over to the center of the bed or even the other side of the bed after the first user has exited. The second user's sleep would remain tracked regardless of where the second user migrates to within the bed after the first user's exit.

Figure 13:
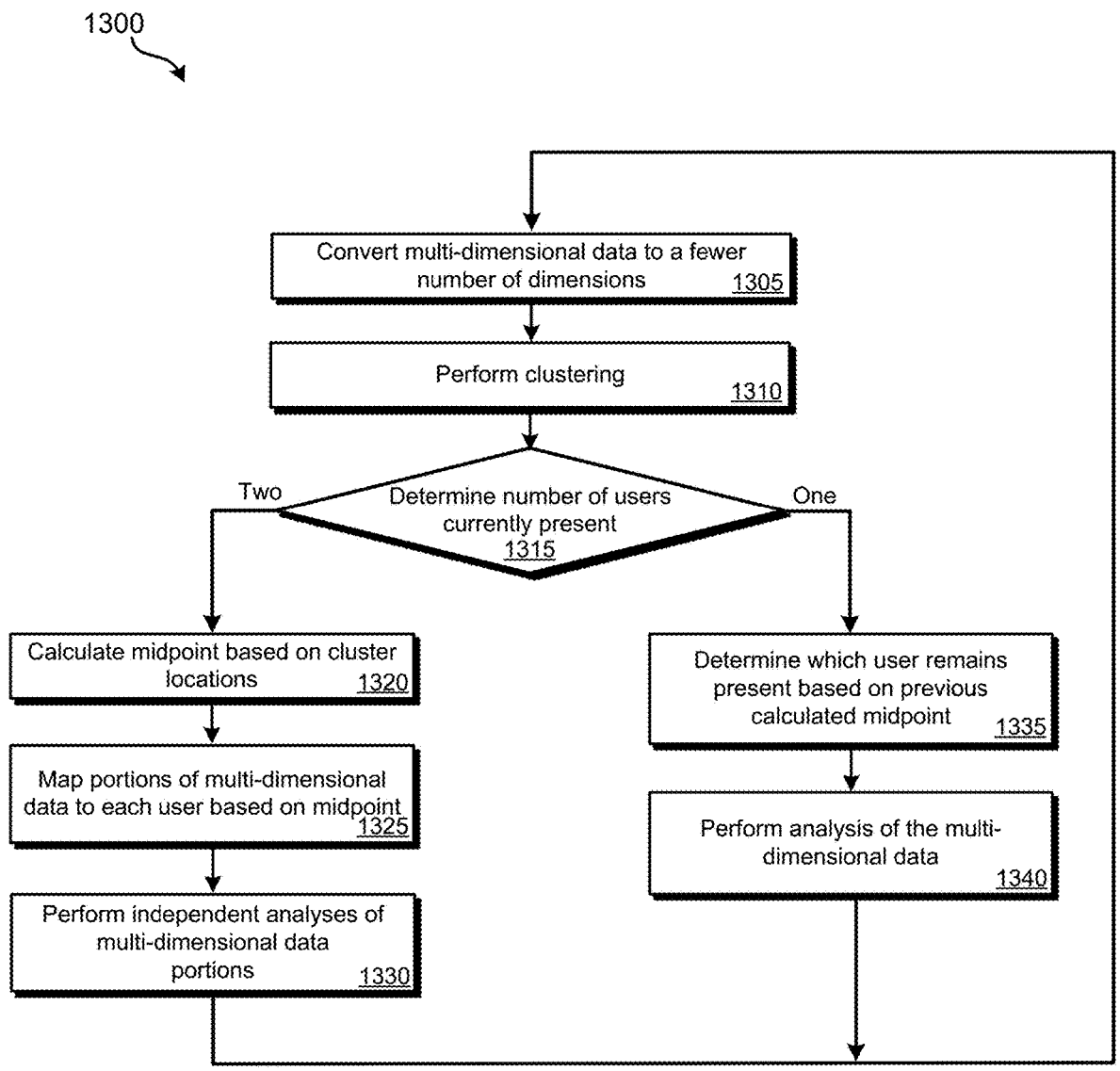
FIG. 13 illustrates an embodiment of a method for performing sleep tracking for multiple users.

Various methods may be performed to independently track the sleep of multiple users within a bed or adjoining beds. FIG. 13 illustrates an embodiment of a method 1300 for performing sleep tracking for multiple users. Typically, method 1300 may be used to separately monitor two users. However, it is possible the principles of method 1300 may be used to monitor more than two users. Method 1300 may be performed using radar processing module 1010, which may be incorporated as part of system 200A or system 200B. Further, such systems may be integrated as part of a single device, such as device 300 of FIGS. 3A and 3B.

At block 1305, waveform data may be received and analyzed after some amount of processing has been performed on the raw chirp waterfall data that has been received from a source. For example, referring to system 200A, radar subsystem 205 may output raw chirp waterfall data that is processed using movement filter 211, frequency emphasizer 212, range-vitals transform engine 213, and range gating filter 214. The processed waveform or waterfall data output by range gating filter 214 may be graphically represented similarly to the data of graphs 1100A and 1100B. That is, the data output by range gating filter 214 may have a first dimension representative of distance, a second dimension representative of frequency, and a third dimension representative of magnitude. In order to separate data for multiple users, this data may initially have one or more dimensions removed. At block 1305, one or more dimensions of the data may be removed, such as by using a maximum or average value for movement frequency for each distance (e.g., each distance range). By performing such a conversion, the frequency dimension may be eliminated, and the data may now only have distance and magnitude components for the analysis of block 1310.

At block 1310, a clustering process may be performed. The clustering may be performed on the data that has been reduced in dimensions from block 1305. The clustering of block 1310 can be understood as an unsupervised clustering problem. A key aspect of the clustering may be that the number of users present is unknown. For instance, while two users may typically sleep in a bed, on any given night, just a single user may be present, or the users may enter and exit bed at different times. A density-based clustering approach may be taken, such as by using the DB SCAN algorithm or some other algorithm, such as k-means clustering performed with progressive counts of assumed clusters, that can determine a number of clusters present and the location of such clusters (e.g., a center point of each cluster or location of the cluster along an axis).

At block 1315, based on the number of clusters determined at block 1310, a number of users present may be determined. The number of users may correspond to the number of clusters identified at block 1310. Therefore, if two clusters are identified, two users may be identified as present. While method 1300 focuses on one or two users being present, it is possible that more than two users may also be identified.

If two users are identified as present, method 1300 may proceed to block 1320. At block 1320, a midpoint between the two clusters may be determined. The midpoint may be the average of the two locations of the clusters identified at block 1310. In other embodiments, some other method for determining a location between the two clusters may be performed. The point determined at block 1320 can be used to determine to which user data should be attributed.

At block 1325, the processed multidimensional radar waterfall data or waveform data from block 1305 may then be respectively assigned, or mapped, to each user. In some embodiments, the processed multidimensional radar waterfall data can be mapped to either user but is not mapped to both. In other embodiments, there can be at least some overlap in data that is mapped to each user. Therefore, while the processed data having the reduced number of dimensions may be used for determining the midpoint; further processing may be performed using the multidimensional radar waterfall data from block 1305. At block 1325, a first point of the multidimensional data is assigned to a first user and a second portion of the multidimensional data is assigned to a second user based on the midpoint. For instance, the processed multidimensional radar waterfall data corresponding to a distance greater than the midpoint may be assigned to the second user; the processed multidimensional radar waterfall data corresponding to a distance less than the midpoint may be assigned to the first user.

At block 1330, independent analyses of the multidimensional data mapped to each user may be performed. The independent analyses may be performed to independently determine the sleep state of each user and determine any environmental factor that has woken the user (e.g., as detailed in relation to FIG. 6). Referring to FIG. 10, separate instances of components, such as spectral summation engines 1015 and neural networks 1016, may be used to analyze data mapped to each user. Sleep state detection may then be performed independently for each user based on the mapped data.

If, during a subsequent iteration of method 1300 after determining that two users are present, a determination is made at block 1315 that a single user is present, method 1300 may proceed to block 1335. Such a situation may occur when two users are sleeping in a same bed and one user gets out of bed, either for the day or temporarily. A determination of which user remains in bed may need to be made to attribute future sleep events to the still-in-bed user.

At block 1335, a determination may be made as to where the single cluster is located in relation to a previously determined midpoint from block 1320. The most recently determined midpoint from block 1320 may be used or, for example, an average of a number of most-recent midpoints. The user who remains in bed may be identified based on whether the cluster of the single user in bed is closer to the device than the midpoint or farther away from the device than the midpoint. The single cluster is attributed to the user who was previously identified on the same side of the midpoint when method 1300 identified two users as present. Following this analysis, even if the user rolls or otherwise moves within bed, the same single user will be attributed with the sleep data regardless of where the user is located with respect to the midpoint. That is, when a user exits, the midpoint is used to determine which user remains; future motion of the user that is still in bed with respect to the midpoint has diminished significance because it is already known which user has remained in bed and which has exited.

If the user who exited bed returns, it may be assumed that the user will resume being on the same sides of the bed as previously determined at block 1325. For instance, if a user on the far side of the bed exited, it may be assumed that when the user returns, they will be the user on the far side of the bed again.

At block 1340, an analysis may be performed to determine the sleep state of the single user. A spectral summation engine and neural network may be used to analyze data mapped to the single user. Sleep state detection continues to be performed for the single user even though another user has exited bed (or is otherwise no longer detected).

In FIGS. 14-17, a beam-steering module is detailed. The beam-steering modules of FIGS. 14 and 16 perform receive-side beam-steering. The specific radar subsystem used may reside on a single integrated circuit, such as Infineon's® BGT60 chip. As detailed in relation to FIG. 15, a single transmit antenna is present and multiple (e.g., 3) receive antennas are present. In other embodiments, multiple transmit antennas may be present to perform transmit-side beam-steering in addition to or instead of receive-side beam-steering.

A beam-steering module may process data provided from each antenna by radar subsystem 205 prior to such data being processed by radar processing module 210. A beam-steering module may serve to perform beam-steering, thereby emphasizing reflected radio waves received from a direction in which the user sleeps and deemphasizing reflected radio waves from other directions, such as static objects (e.g., a wall, headboard, etc.). It should be understood that the term beam-forming may be used interchangably with the term beam-steering. Beam-steering modules, as detailed herein, may be used with any of the detailed embodiments of contactless sleep tracking devices and associated methods. Beam-steering modules may function in the analog domain or digital domain. If the radar subsystem outputs digital data, the beam-steering module may function fully in the digital domain using digital components.

In digital embodiments, functionality of a beam-steering module may be implemented as software executed by the same one or more processors as radar processing module 210. Alternatively, functionality of a beam-steering module may be implemented by dedicated hardware or incorporated as part of radar subsystem 205.

Figure 14:
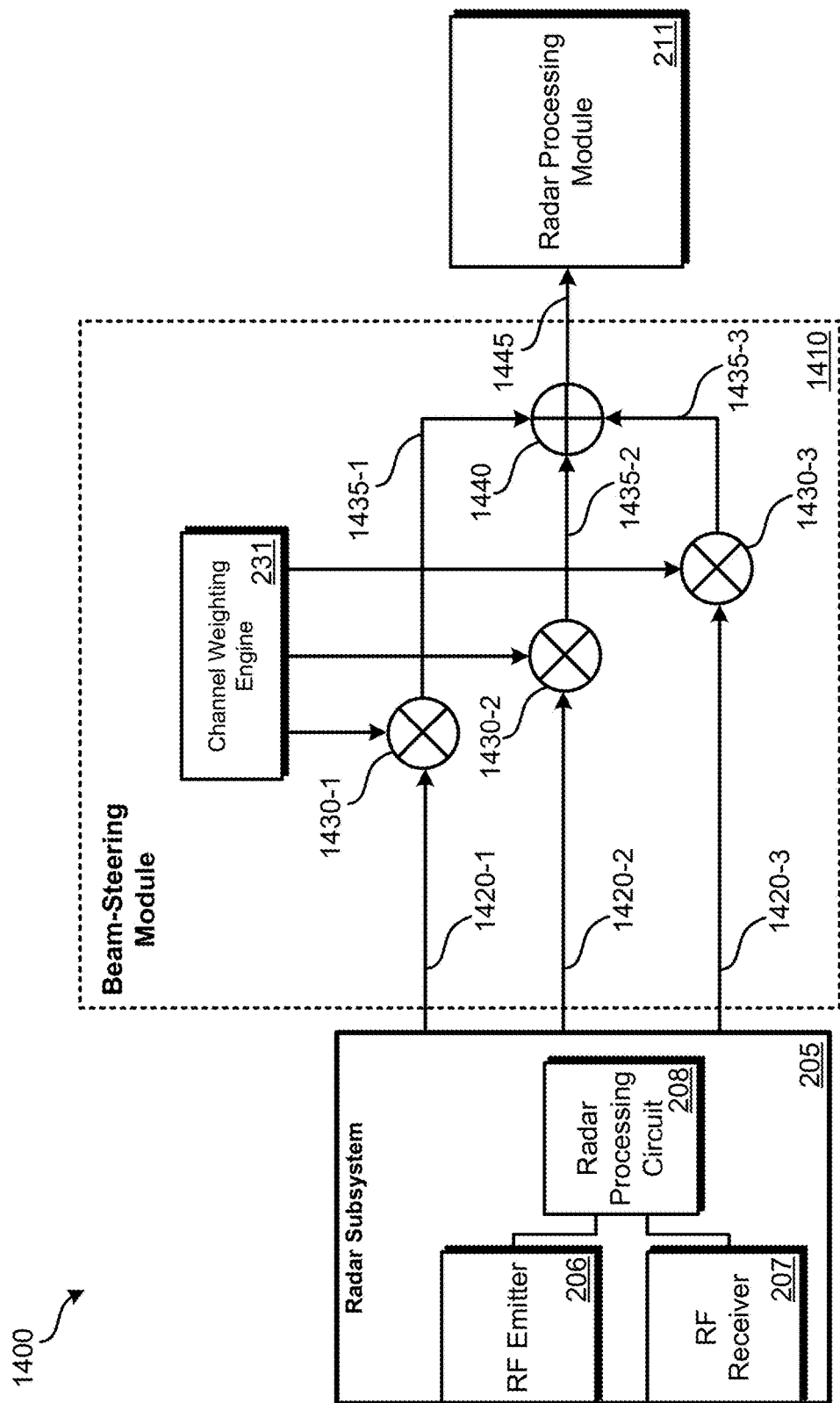
FIG. 14 illustrates an embodiment of a beam-steering module for a contactless sleep tracking device that targets the direction in which sleep tracking is performed.

FIG. 14 illustrates an embodiment 1400 of beam-steering module 1410 for targeting the direction in which sleep tracking is performed. Beam-steering module 1410 can represent an embodiment of beam-steering module 230. Generally, beam-steering module 1410 may apply a weight to each antenna data stream received from radar subsystem 205, sum the weighted inputs, and output the combined weighted antenna data stream to radar processing module 210. The weights applied may introduce a delay to the input of a particular antenna, which can be realized by the weight being a complex value. By a delay being introduced to one or more of the antenna data streams received from the antennas, the antenna receive beam can be effectively steered.

In embodiment 1400, three digital antenna data streams 1420 (1420-1, 1420-2, 1420-3) are received from radar subsystem 205 with each digital antenna data stream corresponding to a separate antenna. Therefore, in this embodiment, three antennas are present as part of radar subsystem 205. In other embodiments, radar subsystem 205 may have fewer (e.g., 2) or greater numbers (e.g., 4, 5, 6, 7, or more) of antennas, each with a corresponding raw antenna data stream output in digital form to beam-steering module 1410.

Mixers 1430 and combiner 1440 can represent beam steering system 232. Each of antenna data streams 1420 may be input to a separate mixer of mixers 1430. Mixers 1430 may be digitally implemented and may therefore represent software processes. Mixer 1430-1 mixes antenna data stream 1420-1 with a weight, represented by a complex value, output by channel weighting engine 231. Mixer 1430-2 mixes antenna data stream 1420-2 with a weight (which may be the same or differ from the weight applied at mixer 1430-1), output by channel weighting engine 231. Mixer 1430-3 mixes antenna data stream 1420-3 with a weight (which may be the same or different from each of the weights applied at mixers 1430-1 and 1430-2), output by channel weighting engine 231.

Channel weighting engine 231, which can represent a software process, may perform a training process to determine the values (e.g., complex values) representative of the weights that should be output to each of mixers 1430. In other embodiments, channel weighting engine 231 may be performed by separate specialized hardware or hardware that is incorporated as part of radar subsystem 205. The digital signals representing the weights output by channel weighting engine 231 may effectively apply a greater or smaller delay to each of antenna data streams 1420. The weights applied via mixers 1430 may be normalized to 1. Therefore, the sum of the three weights applied in embodiment 1400 may sum to 1.

Beam steering system 232 and beam-steering module 1410 can be used to implement weighted delay and sum (WDAS) beam-steering via mixers 1430. Equation 4 details how WDAS can be implemented:

$$\hat{x} = \Sigma_{i=1}^{M} w_i * x_i = \Sigma_{i=1}^{M} (a_i * e_i^{-j\pi\theta_i}) * x_i.$$ Eq. 4

In Equation 4, $w_i$ represents the channel weight, which can be a complex value to introduce phase delay; $x_i$ represents the incoming digital radar data (e.g., a FMCW radar chirp) from radar subsystem 205; $a_i$ represents the complex-valued weights that are responsible for phase-delaying different receive antenna signals with different magnitudes. The weightings output by channel weighting engine 231 may be determined by performing a least-squares optimization process. The least squares optimization process may be performed according to Equation 5.

$$\text{minimize} \|y - Xw\|^2$$ Eq. 5

In Equation 5, y represents vectorized data generated using the target beam. X represents the antenna data stream data received from radar subsystem 205; w represents the weights that are to be learned by channel weighting engine 231. As part of a training process to determine the most effective weights to target the user, various weights may be tested (e.g., in a pattern, randomly) in an attempt to obtain a minimized output of Equation 5. For example, if enough randomized weights are tested, it can be expected that the minimized output value can be obtained within an amount of error. By minimizing the output value according to the least-squares optimization process, the weights corresponding to the beam direction that most closely targets where the user is located within the bed may be obtained. These weights may then be used for future monitoring of the user. Periodically or occasionally, retraining may be performed to compensate for the user moving within the bed and/or the orientation and/or location of the sleep detection device being changed.

Prior to use, weights may be determined offline to compensate for a known tilt of the radar subsystem, such as indicated in FIG. 3A and indicated by directions 350 and 352. When a user is present, the optimal direction is determined for the user, such as by sweeping or randomly selecting weights. When a user is not present, one or more directions to stationary objects that produce significant reflections can be determined such that these one or more directions can be avoided when targeting a user.

It should be understood that a learning process other than a least squares optimization process may be performed by channel weighting engine 231. For instance, in some embodiments, a user may assist in the training process by providing an input indicating a direction from the contactless sleep tracking device to where the user sleeps. In other embodiments, a different form of automated learning process may be performed to target the beam at the user.

Channel weighting engine 231 may be triggered to determine weights on system 200B being booted or turned on. If motion is detected by system 200B, such as via an on-board accelerometer, channel weights may be recalculated.

A summation of the weighted antenna data streams 1435 (e.g., 1435-1, 1435-2, and 1435-3), as output by mixers 1430, may be received by combiner 1440. Combiner 1440 may output a single summed output 1445 to radar processing module 210. By at least one weight (that causes a delay) applied by mixers 1430 differing from the other weights applied by mixers 1430, the beam is effectively steered in a direction, which may have a vertical and/or horizontal component. Processing by radar processing module 210 may be performed as detailed in relation to FIGS. 2A and 2B.

Figure 15:
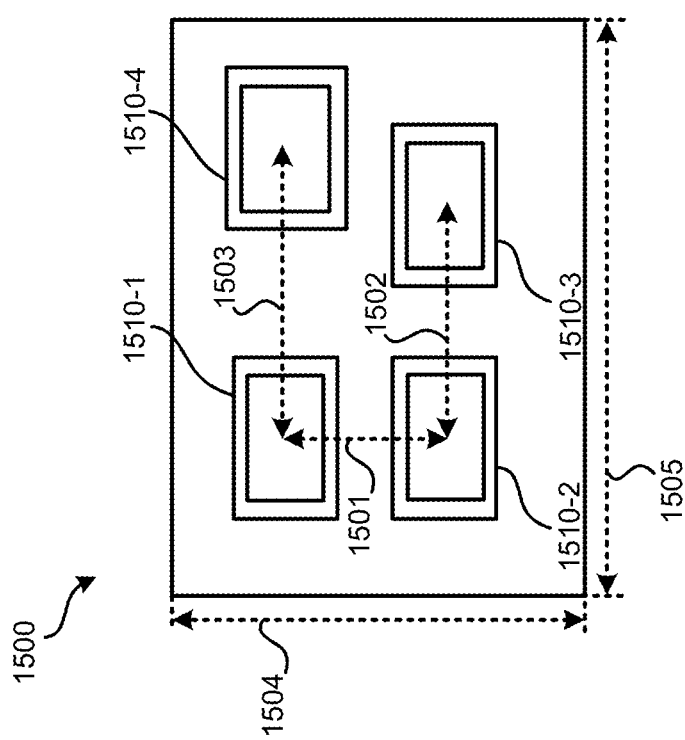
FIG. 15 illustrates an embodiment of the antenna layout of a radar subsystem that may be used in combination with a beam-steering module of a contactless sleep tracking device.

FIG. 15 illustrates an embodiment of a possible antenna layout of radar subsystem 1500. Radar subsystem 1500 may represent an embodiment of the integrated circuit that functions as radar subsystem 205. The entire IC may have dimensions of 6.5 mm (length 1505) by 5 mm (width 1504). In other embodiments, the entire IC has a length 1505 by width 1504 of between 7 mm by 7 mm and 4 mm by 4 mm. The illustrated embodiment of radar subsystem 205 has three receive antennas and one transmit antenna, but other embodiments may have a greater or fewer number of antennas. Radar subsystem 1500 may have receive antennas 1510-1, 1510-2, and 1510-3 distributed in an "L" pattern. That is, antennas 1510-1 and 1510-2 may be aligned on axis

1501 and antennas 1510-2 and 1510-3 may be aligned on axis 1502 which is perpendicular to axis 1501, as illustrated in FIG. 15. The center of antenna 1510-2 may be located 2.5 mm or less from the center of antenna 1510-1. The center of antenna 1510-2 may be located 2.5 mm or less from the center of antenna 1510-3.

Transmit antenna 1510-4 may be arranged separately from the L-shaped pattern of the receive antennas 1510-1, 1510-2, and 1510-3. That is, in some embodiments, a center of transmit antenna 1510-4 is not be located on an axis with antenna 1510-3 that is parallel to axis 1501. In some embodiments, transmit antenna 1510-4 is on axis 1503 with center of antenna 1510-1, with axis 1503 being parallel to axis 1502.

Each of antennas 1510 may be hollow rectangular dielectric resonance antennas (DRAs). Each of antennas 1510 may have a same set of dimensions. Alternatively, each of receive antennas 1510-1, 1510-2, and 1510-3 may have the same dimensions and transmit antenna 1510-4 may vary in dimensions from the receive antennas. In some embodiments, transmit antenna 1510-4 has a larger width, such as 0.2 mm larger, than receive antennas 1510-1, 1510-2, and 1510-3 but the same length.

In such an arrangement, the phase delay introduced by the applied weights between the antenna data stream of antenna 1510-1 and the data stream of antenna 1510-2 may affect the vertical direction of the receive beam and the phase delay introduced by weights between the antenna data stream of antenna 1510-2 and data stream of antenna 1510-3 may affect the horizontal direction of the receive beam (assuming the radar subsystem integrated circuit is present within the contactless sleep tracking device in approximately the same orientation).

In some embodiments, separate antennas are used for transmitting and receiving. For example, antenna 1510-4 may be used exclusively for transmitting, while antennas 1510-1, 1510-2, and 1510-3 are used exclusively for receiving.

Using a radar subsystem in which all the antennas are located on a single, relatively compact integrated circuit chip, as described, has been found to achieving a good balance of cost savings, reasonable ability to perform receive-side beam-steering, and a sufficiently wide antenna pattern in the horizontal plane that is able to encompasses common bed sizes (e.g., queen, king, full, twin). At the same time, a device incorporating such a radar subsystem allows it to be placed sufficiently close to a bed (e.g., within 1 m) that can also function as a personal assistant, including alarm clock functionality (which can replace an alarm clock), home control hub, and/or entertainment touchscreen device.

While the beam-steering module of embodiment 1400 does not factor in the arrangement of antennas 1510 with respect to each other, embodiment 1600 accommodates the topology of the antenna arrangement of radar subsystem 1500. In other embodiments, antennas 1510 may be arranged in a pattern other than an "L."

Figure 16:
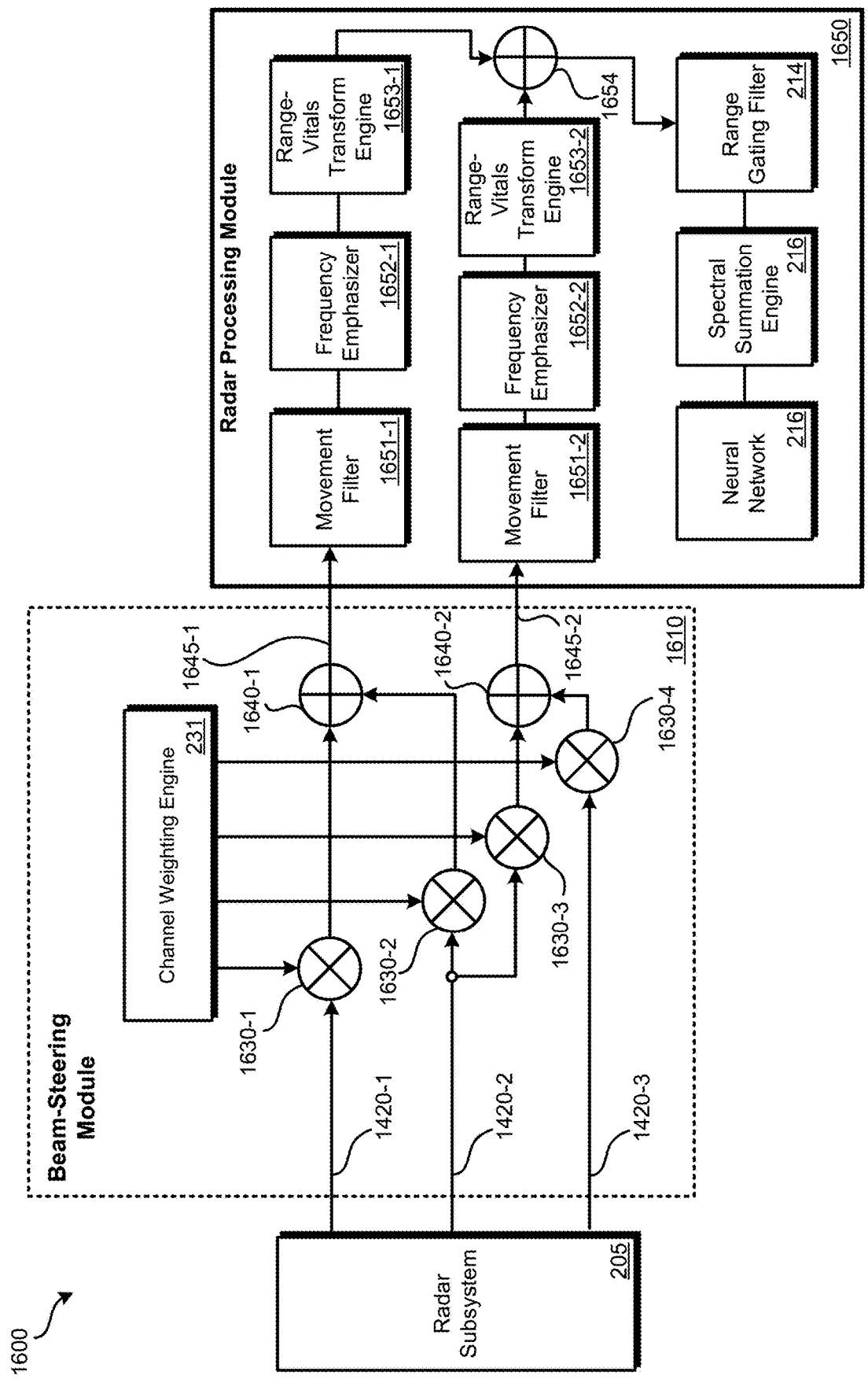
FIG. 16 illustrates another embodiment of a beam-steering module for targeting the direction in which sleep tracking is performed.

FIG. 16 illustrates an embodiment 1600 of a beam-steering module for targeting the direction in which sleep tracking is performed. In embodiment 1600, the antenna arrangement (i.e., antenna topology) of radar subsystem 205 is taken into account. By taking the antenna topology into account, more accurate beam-steering may be performed, which can result in more accurate tracking of a user while sleeping in the user's bed. Antenna 150-1 corresponds to antenna data stream 1420-1, antenna 1510-2 corresponds to antenna data stream 1420-2, and antenna 1510-3 corresponds to antenna data stream 1420-3. That is, a phase delay added between the data streams of antenna 1510-2 of radar subsystem 205 and antenna 1510-3 is used for horizontal beam targeting and a phase delay added between the data streams of antenna 1510-2 and antenna 1510-1 is used for vertical beam targeting. Depending on whether the data stream of antenna 1510-2 is used for vertical or horizontal beam targeting, a different weight may be applied using separate digitally implemented mixers.

As in embodiment 1400, in embodiment 1600, separate digital antenna data streams 1420 are received from each antenna of radar subsystem 205. Mixers 1630 and combiners 1640 can represent beam steering system 232 of FIG. 2B. In embodiment 1600, beam-steering module 1610 has four mixers 1630 (1630-1, 1630-2, 1630-3, and 1630-4). Similar to embodiment 1400, a value (e.g., complex value) output by channel weighting engine 231 may be mixed with each antenna data stream of antenna data streams 1420. However, different weights may be mixed with antenna data stream 1420-2, with two weighted outputs created, to be used separately for horizontal and vertical beam targeting. Antenna data stream 1420-1 may have a weight applied via mixer 1630-1 and may be combined via combiner 1640-1 with antenna data stream 1420-2 (which had a weight applied via mixer 1630-2). The weights applied at mixers 1630-1 and 1630-2 may sum to a normalized value of 1. Antenna data stream 1420-3 may have a weight applied via mixer 1630-4 and may be combined via combiner 1640-2 with antenna data stream 1420-2 which had a weight applied via mixer 1630-3. The weights applied at mixers 1630-3 and 1630-4 may sum to a normalized value of 1.

Channel weighting engine 231 may be implemented similarly to as implemented in embodiment 1400. Channel weighting engine 231 may perform a least-squares optimization process or some other optimization process to determine the optimal or near optimal direction of the receive beam. Channel weighting engine 231 may generate four outputs to be used for weighting in embodiment 1600 rather than three outputs as in embodiment 1400. Therefore, if a pattern or random set of values output for the weights is used as part of the least-squares optimization process, a greater number of sets of output values in embodiment 1600 may be tested to obtain the optimized set of output values used to set the weights as compared to embodiment 1400.

Two outputs 1645, output 1645-1 and output 1645-2, may be output to radar processing module 1650. Separate processing may then be performed by radar processing module 1650 for output 1645-1 and output 1645-2. At a high level, processing by radar processing module 1650 may be performed on each of outputs 1645 until direction is no longer used during processing. In embodiment 1600, separate instances of movement filters, frequency emphasizers, and range-vital transform engines may be applied to each of outputs 1645, then the results may be averaged or summed together. More specifically, output 1645-1 may be output to movement filter 1651-1, followed by frequency emphasizer 1652-1, followed by range-vitals transform engine 1653-1. Output 1645-2 may be output to movement filter 1651-2, followed by frequency emphasizer 1652-2, followed by range-vitals transform engine 1653-2. Movement filters 1651, frequency emphasizers 1652, and range-vital transform engines 1653 may function as detailed in relation to movement filter 211, frequency emphasizer 212, and range-vitals transform engine 213 of FIGS. 2A and 2B. The output of range-vitals transform engine 1653-1 and range-vitals transform engine 1653-2 may be summed or combined using combiner 1654. The output of combiner 1654, which can represent an average of the outputs of range-vitals transform engines 1653, may be processed by range gating filter 214 and later components as detailed in relation to FIGS. 2A and 2B.

Since radar processing module 1650 and beam-steering module 1610 may be performed as a software process executed by a general-purpose processor (or multiple processors), implementing more complex mixing, weights, and multiple instances of movement filters 1651, frequency emphasizer 1652, and range-vitals transform engine 1653 may require that enough processing capability be available. Therefore, assuming such processing power is available, no hardware changes to the contactless sleep tracking device may be needed to implement embodiment 1600 instead of embodiment 1400. In some embodiments, embodiment 1400 may be implemented and if sleep tracking results are inaccurate, embodiment 1600 may be implemented (or the reverse). Advantageously, in some embodiments in which the contactless sleep tracking device 300 comprises a smart-home management device (e.g., a Nest Home Hub) into which the radar functionalities are integrated, the smart-home management device being a network-connected combination of smart speaker, home assistant, and touchscreen-based control and/or entertainment hub, improvements to parameter computation methods and even entire radar processing algorithms can be achieved by in-the-field software updates pushed out as needed by a central cloud server via the Internet.

While the receive-side beam-steering aspects of embodiments 1400 and 1600 of FIGS. 14 and 16, respectively, are implemented in the digital domain, the functionality of beam-steering modules 1410 and 1610 may be implemented in the analog domain using analog components. If such beam-steering is performed in the analog domain, conversion to the digital domain may be performed following such analog beam-steering being performed such that digital data is provided to radar processing module 210 or 1650.

Figure 17:
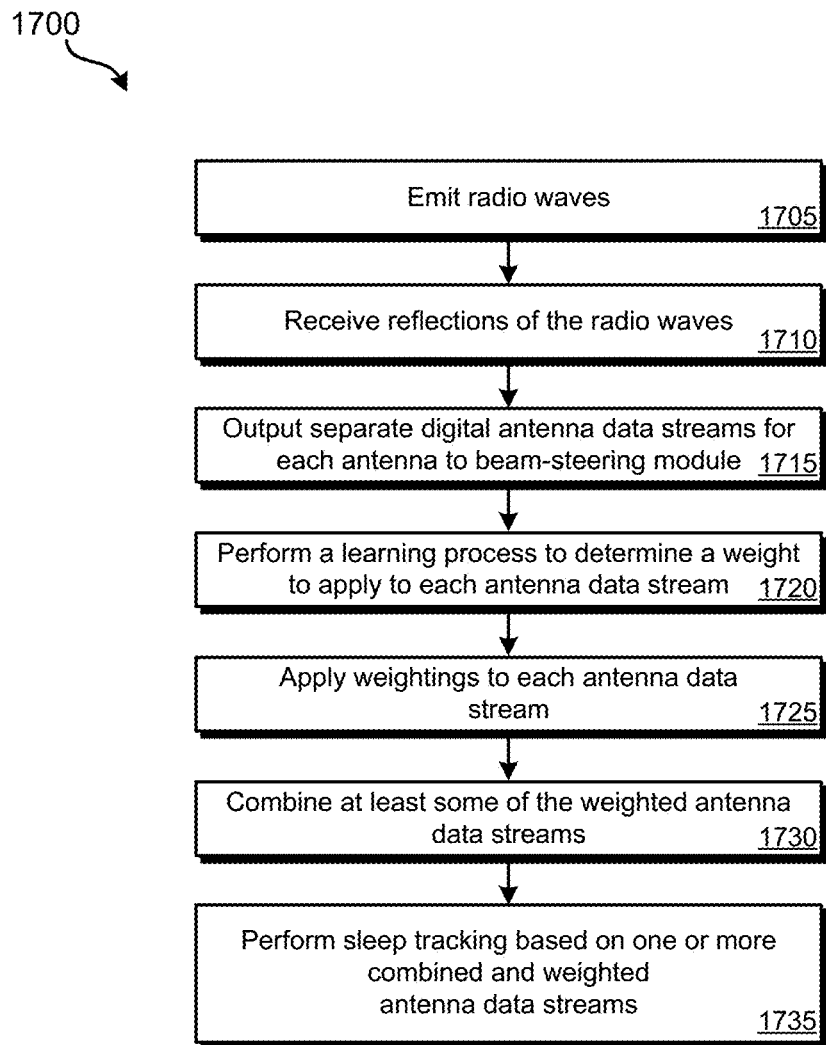
FIG. 17 illustrates an embodiment of a method for directionally targeting sleep tracking.

Various methods can be performed using embodiments of beam-steering modules, such as beam-steering modules 1410 and 1610 of FIGS. 14 and 16, respectively. FIG. 17 illustrates an embodiment of a method 1700 for directionally targeting sleep tracking (or, possibly, for some other form of tracking, such as for coughs as detailed in relation to FIGS. 18-21). Method 1700 may be performed using systems such as present in embodiments 1400 and 1600. In some of such embodiments, the antenna topology of FIG. 15, or some similar L-shaped topology, may be present. Method 1700 may be performed by such systems which are incorporated as part of device 300 of FIGS. 3A and 3B.

Method 1700 may be performed in combination with any of the preceding detailed methods. Therefore, overlap exists in the various blocks performed as part of the various methods as detailed below.

At block 1705, radio waves are emitted. The radio waves emitted can be continuous-wave radar, such as FMCW. The raw waveform data passed to radar processing module may include waveform data indicative of continuous sparse reflected chirps due to the radar subsystem operating in a continuous sparse sampling mode or due to the radar subsystem operating in a burst mode and a conversion process to simulate raw waveform data produced by the radar subsystem operating in a continuous sparse sampling mode being performed. The radio waves emitted at block 805 may be emitted in accordance with the FMCW radar scheme of FIG. 2C. The radio waves emitted can be emitted by RF emitter 206 of radar subsystem 205. At block 1710, reflections of the radio waves may be received, such as by multiple antennas of RF receiver 207 of radar subsystem 205. The reflections received at block 1710 may be reflected off of moving objects (e.g., a person having a heartbeat and breathing) and stationary objects. For each FMCW chirp emitted at block 1705, a number of samples may be measured of reflected RF intensity, such as 64 samples, at block 1710. Fewer or greater numbers of samples may be measured in other embodiments. A phase shift may be present in the radio waves reflected by a moving object. Blocks 1705 and 1710 may correspond to blocks performed as part of one or more of the other methods detailed herein, such as blocks 805 and 810 of method 800.

At block 1715, raw waveform data, which can also be referred to as raw chirp waterfall data, may be created based on received reflected radio waves by each antenna. The reflected radio waves may be indicative of distance and a phase shift. At a given frequency, such as 10 Hz, a number of samples may be taken, such as 64 samples. For each of these samples, intensity and phase shift data may be present, and may be output as a digital antenna data stream, with a separate antenna data stream being present for each antenna used to receive the reflected radio waves. Further processing may be performed in the digital domain. In other embodiments, the antenna data streams may be output by the radar subsystem as analog data and the weighting process may be performed in the analog domain. Over time, a window of raw waveform data may be created and stored in a buffer for analysis. Referring to FIG. 2, block 815 may be performed by radar processing module 210.

At block 1720, a learning process may be performed to determine a weight to apply to each received antenna data stream. As detailed in relation to channel weighting engine 231, various values that function as weights may be tested and a most effective set of weights may be determined that results in beam-steering that best targets the location of the user. The values applied may be complex and, thus, may function to introduce phase delay to one or more of the received antenna data streams. Such introduced delay can effectively target the receive antenna beam in a particular direction, which may have a vertical and/or horizontal component.

The learning process performed as part of block 1720 can involve a least-squares optimization process being performed or some other form of optimization. In some embodiments, a particular direction may be locked or limited for beam-steering purposes. For instance, horizontally, the beam may be desired to be at 90° to the face of the contactless sleep tracking device, such as shown in FIG. 3A. Alternatively, the beam may be limited to vary by a limited range from orthogonal to the face of the contactless sleep tracking device (e.g., 10°). Additionally or alternatively, the values used for weighting may compensate for a vertical inclination angle of the display of the contactless sleep tracking device, such as indicated in FIG. 3A in reference to directions 350 and 352. Therefore, the values used to determine the optimized angle may be restricted to within a particular range such that the vertical and/or horizontal direction of the beam stays within particular ranges (e.g., +/−10° horizontally, +2° to −25° vertically).

After the learning process of block 1720 is complete, blocks 1705, 1710, and 1715 continue to be performed such that antenna data streams continue to be output by the radar subsystem. At block 1725, the values to apply as weights determined at block 1720 may be applied to the antenna data streams to perform beam-steering while performing a sleep tracking process for one or more users. At block 1730, the weighted antenna data streams may be combined, such as by summing the data streams together. Block 1730 can involve all weighted antenna data streams being summed together, such as in embodiment 1400, to create a single output stream. Block 1730 can also include multiple output streams being created by summing different groups of weighted antenna streams together, such as in embodiment 1600. As in embodiment 1600, a particular antenna data stream may be used twice, with different weights applied, for use in targeting the receive antenna beam horizontally and vertically.

At block 1735, sleep tracking may be performed using one or more combined and weighted antenna data streams. In some embodiments, if a single output is present from block 1730, such as in embodiment 1400, processing may be performed by radar processing module 210 as detailed in relation to movement filter 211, frequency emphasizer 212, range-vitals transform engine 213, range gating filter 214, spectral summation engine 215, and neural network 216. In other embodiments, if more than one output is present from block 1725, such as in embodiment 1600, at least some processing of radar processing module 210 may be performed separate for each weighted and combined antenna data stream. For instance, the processing of a movement filter, frequency emphasizer, and range-vitals transform may be applied separately to each weighted and combined antenna data stream. Following such separate processing, the processing data streams may be averaged together and further processing as part of the sleep tracking process may be performed, such as by range gating filter 214, spectral summation engine 215, and neural network 216, as detailed in relation to FIGS. 2A and 2B. While block 1735 is focused on sleep tracking, block 1735 can additionally or alternatively be focused on cough attribution based on user movement as detailed in relation to FIGS. 18-21.

Embodiments of sleep tracking devices detailed herein can also function as a cough attribution device. Alternatively, in some embodiments, devices detailed herein do not perform sleep tracking functions but instead perform cough detection and attribution functions. When sleep data is presented to a user, cough data may be incorporated therein, such as the time and numbers of coughs for a particular user. Further, cough trends over time may be monitored for a particular user. The user may be informed how their amount of coughing over time (e.g., days, weeks, months, even years) has increased or decreased.

Figure 18:
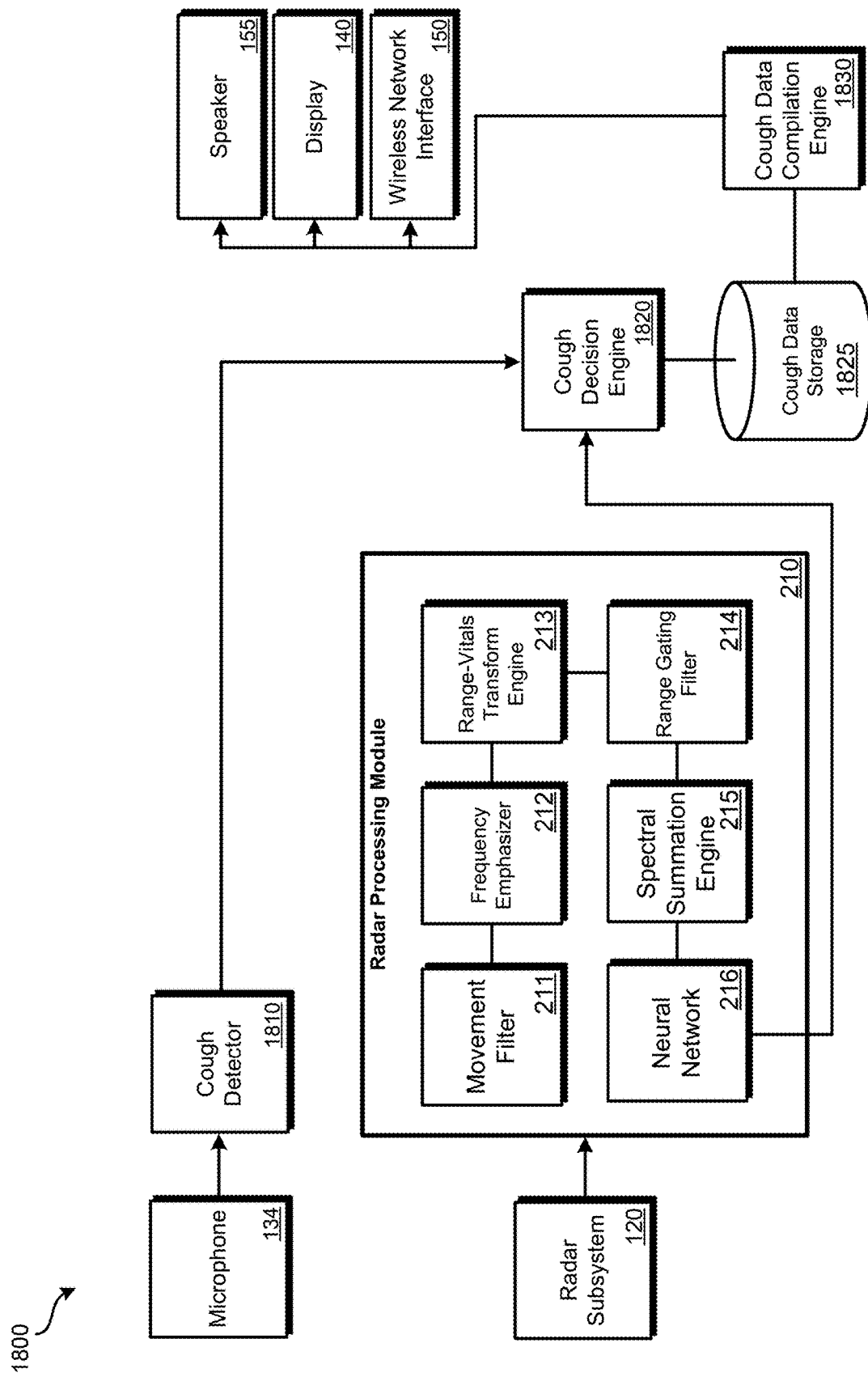
FIG. 18 illustrates a cough detection and attribution device.

FIG. 18 illustrates an embodiment of cough detection and attribution system 1800 ("cough attribution system 1800"). In some embodiments of contactless sleep tracking device 101, the functionality of cough attribution system 1800 is incorporated. Alternatively, cough attribution system 1800 can be implemented in a device that does not perform sleep tracking functions. Cough attribution system 1800, can include radar subsystem 205 (which can represent an embodiment of radar subsystem 120); radar processing module 210 (which can represent an embodiment of radar processing module 112) or radar processing module 1010 (which can also represent an embodiment of radar processing module 112). In some embodiments, a beam-steering module, such as beam-steering module 230, may be incorporated as part of cough attribution system 1800. In other embodiments, a beam-steering module is not present. Advantageously, by virtue of using radar and audio, system 1800 is capable of performing cough detection and attribution without making any physical contact with the monitored user or a bed of the monitored user.

Cough attribution system 1800 can include: microphone 134; radar subsystem 120 (which can be radar subsystem 205); cough detector 1810; radar processing module 210 (or 1010); cough data storage 1825; cough decision engine 1820; cough data compilation engine 1830; display 140; wireless network interface 150; and speaker 155. Any component of cough detector 1810, radar processing module 210 (or 1010), cough data storage 1825, cough decision engine 1820, cough data compilation engine 1830, which can represent software processes performed using one or more processors may be executed locally or may be performed remotely using a cloud-based server system.

Microphone 134 may continuously receive audio and output data based on the received audio to cough detector 1810. In some embodiments, microphone 134 is used to monitor an ambient environment for multiple forms of audio, such as a cough, disturbance or a spoken command, which may be triggered by a particular keyword or key phrase. In some embodiments, multiple microphones are present as part of the cough attribution device. Audio streams from such separate microphones may be combined together or analyzed separately. In some embodiments, audio is only monitored for coughs and/or disturbances when a user has been detected in bed by radar processing module 210 or radar processing module 1010, a feature that is advantageous for a bedside monitoring device since many users make a significant amount of noise just before entering bed, but are generally intending to be more quiet when they get into bed. Such an automatic entry into the detection mode can obviate the need for a specific voice command or button-press to start the cough monitoring process. Alternatively, or as an optional gating overlay for such feature, audio monitoring may be required to be explicitly authorized each time by the user to be activated. Preferably, the cough attribution system 1800 is configured such that all audio monitoring may be easily, readily, and verifiably disabled by the user at any time. For example, a hardware-based mechanical switch may be provided that disables all onboard microphones of cough attribution system 1800.

Cough detector 1810 may be a software-based process that is executed by a processing system, which includes one or more processors, that determines whether a cough is present in the audio stream received from microphone 134. Cough detector 1810 may be executed by the same processing system that executed radar processing module 210 or may be performed by a separate processing system. Cough detector 1810 may include a trained machine learning model that analyzes the received audio stream and outputs an indication of whether a cough is or is not present. When a cough is identified, a timestamp may be output along with the indication of the cough being present. Additionally or alternatively, to detect sounds other than a cough, a different form of detector may be implemented. For instance, in addition or in alternate to cough detector 1810, a snore detector may be implemented. Additionally or alternatively, for detecting talking in a user's sleep, a speech detector may be implemented. Similar components may be implemented for a user scratching, grinding teeth, flatulence, burping, hiccupping, and/or some other action or bodily function that can be identified using audio.

The trained machine learning model may include a neural network that was trained using truth-tagged training data that includes various identified coughs and audio samples that do not include coughs. In other embodiments, the trained machine learning model can use an arrangement other than a neural network to analyze received audio. While cough detector 1810 may determine whether a cough is present based on the audio stream received from microphone 134, radar may be used to determine whether a monitored user is the source of the cough.

After analysis of the audio stream by cough detector 1810, the audio stream received from microphone 134 may be deleted or otherwise discarded, in which case no audio captured by microphone 134 used for cough analysis would be preserved. Accordingly, even though audio capture performed via microphone 134 is active for cough detection, a user does not need to have privacy concerns due to the audio being discarded following cough detection being performed on the audio stream.

Radar subsystem 120 may function as detailed in relation FIGS. 1, 2A, and 2B. Raw radar data, based on detected reflected radio waves of an FMCW radar system may be output to radar processing module 210. In some embodiments, the one or more data streams output by radar subsystem 120 may first be targeted by a beam-steering module, such as beam-steering module 230, which is detailed in relation to FIGS. 14-17.

Radar processing module 210 may function as detailed in relation to FIGS. 2A and 2B. The output of neural network 216, as previously detailed, may be used to determine a state within state machine 500, such as whether a user is present within bed and moving or present in bed and not moving (besides vital signs). Therefore, an output of neural network 216 (or some other form of classification engine) indicates: 1) whether the user is in bed; and 2) whether the user is moving (more than just vital signs) may be output to cough decision engine 1820. In some embodiments, the state output by radar processing module 210 can include a timestamp.

Cough decision engine 1820 may be a software process that is performed by the processing system that performs the functions of radar processing module 210 and/or cough detector 1810. (It should be understood that for other detected sounds, such as snoring, a snore decision engine may be used in addition or in alternate to cough decision engine 1820.) This processing system may have one or more processors. Cough decision engine 1820 may analyze an indication of a cough being present received from cough detector 1810 in combination with an indication of motion of the user in bed received from radar processing module 210. The timestamps of the detected cough from cough detector 1810 and the detected motion in bed may be required to be within a sufficiently small time period of each other in order for cough decision engine 1820 to determine that the cough was the cause of the user moving. For instance, if the user moving is detected within a predefined time period, such as within the range extending from one second before to three seconds after the cough being detected, the cough and movement may be determined to be correlated (that is, the cough caused the movement). Due to the amount of processing time to analyze the radar data compared to the audio data, a sufficiently sized time range may be needed to identify the events as related. In some embodiments, the time window is +/−1 second. In other embodiments, the time window is greater (e.g., +/−2 seconds) or smaller (e.g., +/−0.7 seconds).

If a cough is detected by cough detector 1810 but the monitored user is not attributed with the cough by cough decision engine 1820 based on the data received from radar processing module 210, cough decision engine 1820 may discard information about the cough as unrelated to the monitored user. Alternatively, even if the cough is not identified as originating from the monitored user, the cough may be treated as an audio event, such as detailed in relation to FIG. 6. If the cough (as performed or output by someone or something else) is identified as an audio event that caused the monitored user to awake, the cough may be treated as any other audio or may be specifically stored as a cough event that awoke the monitored user.

Cough decision engine 1820, when a cough is detected and the cough is attributed to the monitored user, may store an indication of the cough and a timestamp of the cough to cough data storage 1825 of cough attribution system 1800. (Additionally or alternatively, if other forms of disturbances, such as snoring are monitored, cough data storage 1825 may be used to store such data or a separate data store may be used.) In some embodiments, the indication of the cough and the timestamp of the cough may be output to a cloud-based server system for storage. In some embodiments, based on the magnitude of the audio analyzed by cough detector 1810, an indication of the severity of the cough may be stored (e.g., whether it was a small, medium or large cough based upon a threshold-based volume analysis or some other form of determination that uses a threshold criterion at least partially based on sound volume). In some embodiments, a continuous string of coughs may be treated as a single cough event and an indication of a duration of the cough event may be stored.

Cough data storage 1825 may be incorporated as part of sleep data storage 118 or may be separately stored data. For instance, cough data may be stored in conjunction with sleep data. Cough data storage 1825 may represent a non-transitory processor-readable medium, such as a memory.

Cough data compilation engine 1830 may analyze data from cough data storage 1825 continuously or periodically, such as once per day, possibly when the user wakes in the morning. Cough data compilation engine 1830 may produce a nightly report that outputs data about the user coughing during the night. The nightly report may include information such as: 1) the number of times the user coughed during the night; 2) the duration of such coughs; 3) the time of such coughs; 4) whether the coughs awoke the user; and/or 5) the severity of such coughs. Such a nightly report may be output using synthesized speech via speaker 155 and/or may be represented using text and/or graphical indicators on display 140. Data from the nightly report may be output to a cloud-based server system via wireless network interface 150 for storage and/or further analysis. In other embodiments, the raw cough data from cough decision engine 1820 is output to the cloud-based storage system for analysis. For instance, the functionality of cough data compilation engine 1830 may be performed by a cloud-based server system. Cough data compilation engine 1830 may be used to alternatively or additionally output data about attribution of other sounds, such as snoring, talking, etc.

Cough data compilation engine 1830 may further produce long-term trend data that is incorporated as part of the nightly report or is part of a separate long-term trend report. The long-term trend data may be based on cough data analyzed over a longer period of time than one day or one night. For instance, the long-term trend data may analyze data over a time period such as: one week, multiple weeks, a month, multiple months, a year, multiple months, or some custom time period, such as a time period when a user identifies that they have an illness. The long-term trend data may be output to the user as part of the nightly report or at a less-frequent interval, such as once per week, and/or upon user request. The long-term trend data may be used to indicate to the user information such as: 1) whether the user's frequency of coughing at night is increasing, decreasing, or staying the same (e.g., within a threshold number, or some other form of threshold criterion, of coughs of the user's average cough count); 2) whether the user's cough intensity is increasing, decreasing, or staying the same (e.g., within a threshold range of the average intensity or some other form of determination that uses a threshold criterion at least partially based on intensity); 3) whether the user's cough duration is increasing, decreasing, or staying the same (e.g., within a threshold range of the average duration or some other form of determination that uses a threshold criterion at least partially based on cough duration); and/or 4) whether coughs are becoming more likely, or becoming less likely, or have about the same chance of waking the user from their sleep. In some embodiments, the long-term trend data is output when one of the trends is noteworthy, such as the user's cough frequency has significantly increased.

Such long-term trend data may be output using synthesized speech via speaker 155 and/or may be represented using text and/or graphical indicators on display 140. Data from the long-term trend data may be output to a cloud-based server system via wireless network interface 150 for storage and/or further analysis. In some embodiments, the long-term trend data for coughing is output with long-term trend data for sleeping of the user. In such embodiments, the functionality of cough data compilation engine 1830 may be incorporated with a sleep data compilation engine, such as sleep data compilation engine 119 of FIG. 1. Therefore, cough data may be output with sleep data.

Figure 19:
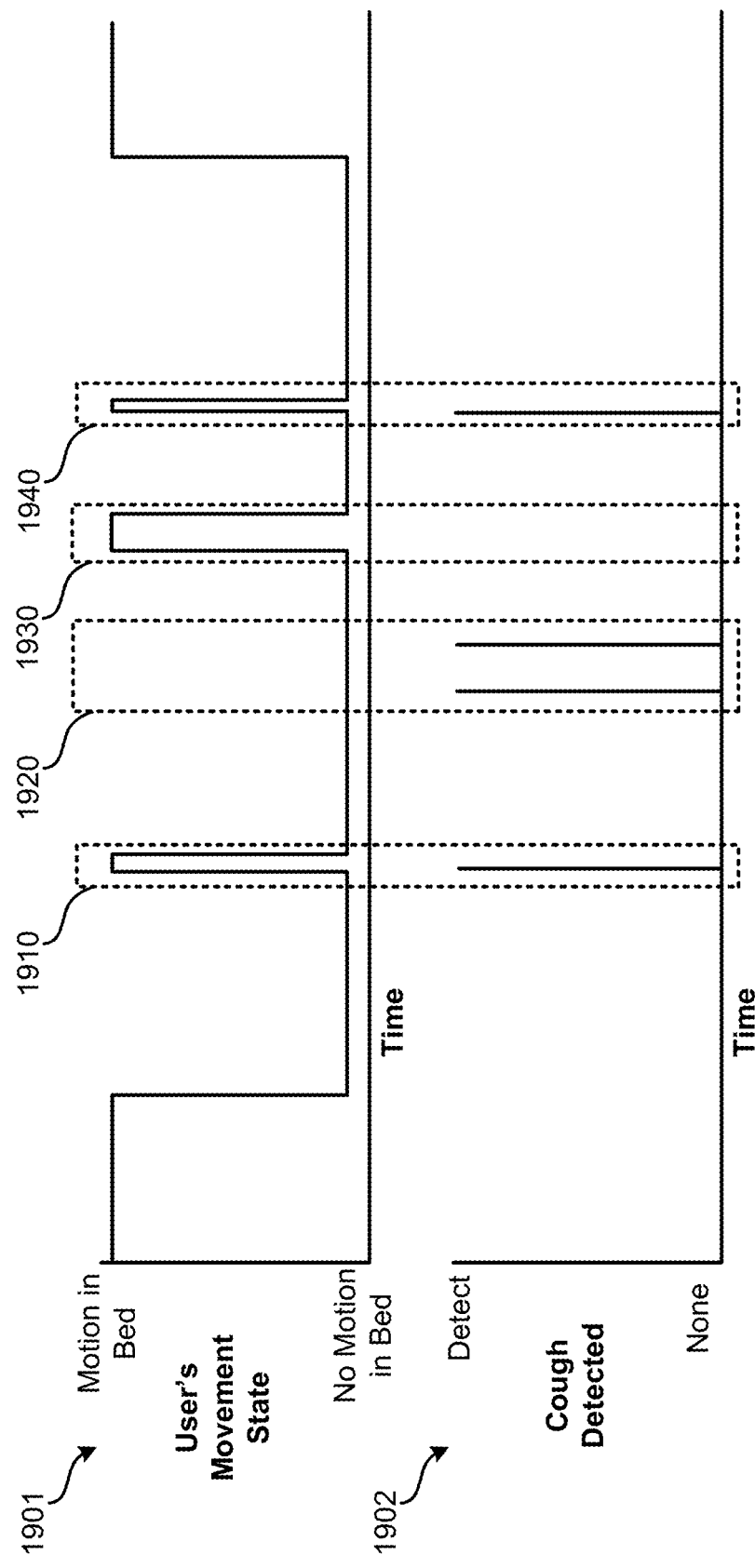
FIG. 19 illustrates examples of timelines of detected coughs and sleep disturbances for a single monitored user.

In some embodiments, a single user may be monitored. This may mean that a single user is present in a bed or may mean that the person who is closest to the cough attribution device is being monitored. However, even if a single person is being monitored, other sources of coughs and cough-like sounds may be nearby, such as other persons, animals (e.g., pets), wind or weather, passing vehicles, or speakers. FIG. 19 illustrates examples of timelines of detected coughs and a user's movement state for a single monitored user. Timeline 1901 illustrates a user's determined movement state based on radar data generated by radar subsystem 120 and processed by radar processing module 210. Timeline 1902 illustrates when a cough was detected by cough detector 1810 based on an audio stream from microphone 134. Notably, a cough being present in timeline 1902 does not necessarily correspond to the user of timeline 1901 since the cough may originate from a source other than the monitored user.

During time period 1910, a cough is detected based on the audio stream and motion is detected by radar processing module 210. In such a circumstance, cough decision engine 1820 attributes the monitored user with having coughed. Similarly, during time period 1940, a cough is detected based on the audio stream and motion is detected by radar processing module 210. Again here, cough decision engine 1820 attributes the monitored user with having coughed. Data indicative of the cough, cough duration, timestamp of the cough, and cough severity may be stored to cough data storage 1825.

During time period 1920, two coughs are detected. However, no motion of the user is detected. Therefore, while a cough may have been present in the audio, the cough is not attributed to the user and no cough data is stored for the user for those particular instances of coughs. In addition to such audio data being indicative of a cough sound having originated from another source, it may be indicative of a false-positive of a cough having been detected based on the audio. Regardless of whether the cough detection is a false positive or if the cough originated from a source other than the user, the data corresponding to that particular "cough" is not stored in relation to the user.

During time period 1930, motion is detected by the user in the bed by radar subsystem 120. This motion represents significant motion that is greater than movement of the user due to breathing or the user's heartbeat. However, no cough was detected based on the captured audio stream. Therefore, no cough data is stored for the user for time period 1930.

In some embodiments, multiple users may be monitored over a same time period. For example, two users sleeping in a same bed, such as in FIG. 9, may each have their sleeping tracked. Additionally or alternatively, each user's coughing may be tracked. If multiple users are having sleep and/or coughing tracked, radar processing module 1010 may be used in lieu of radar processing module 210. In such an embodiment, cough decision engine 1820 may receive two inputs from radar processing module 1010, thereby receiving a separate input for each user. Additional embodiments for three or more users are also possible by adding additional instances of the spectral summation engine and the neural network. Therefore, a separate output may be present for each monitored user that indicates whether the user is present in bed and moving or still. Cough detector 1810 may continue to function as detailed in relation to cough attribution system 1800.

Figure 20:
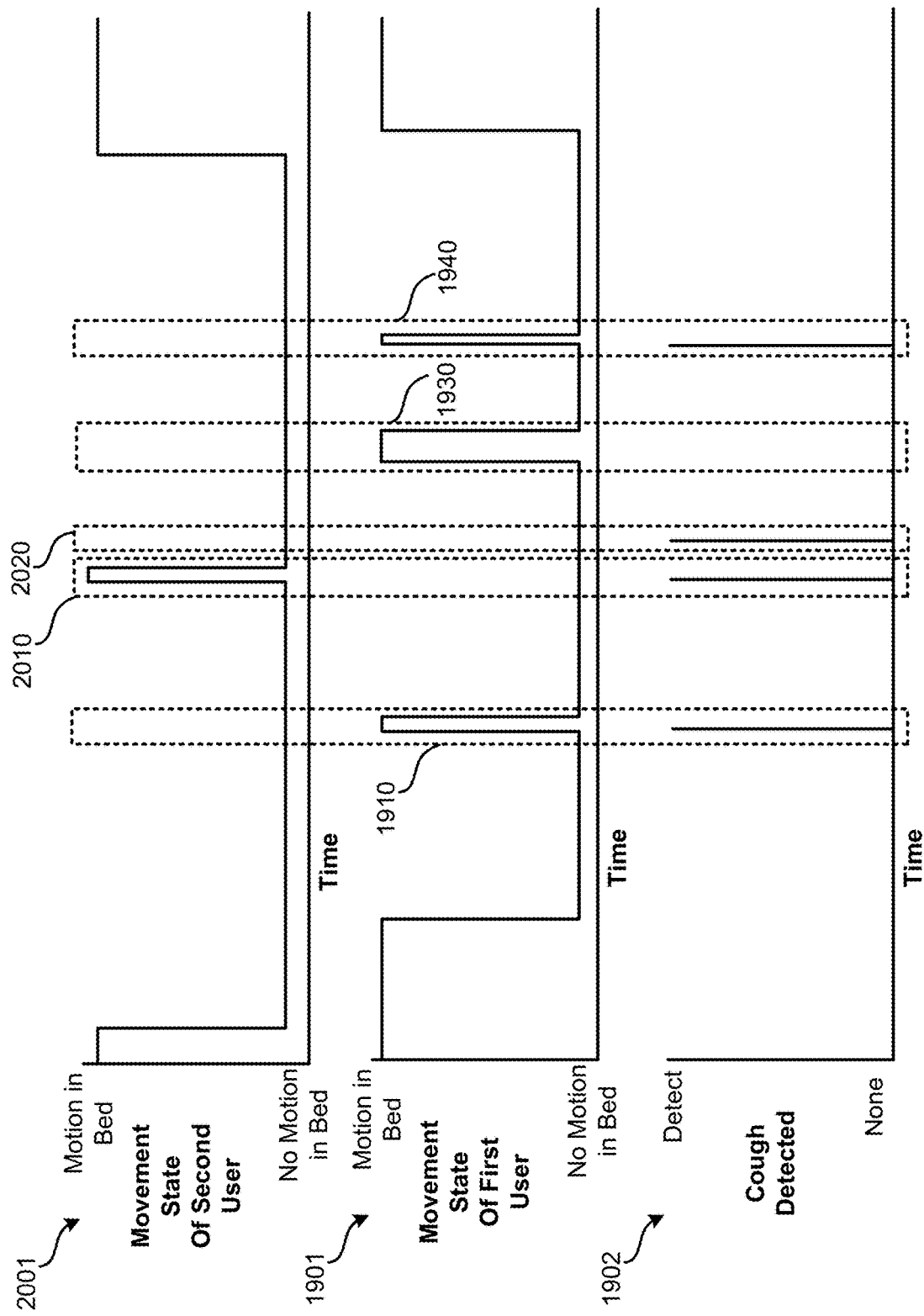
FIG. 20 illustrates examples of timelines of detected coughs and sleep disturbances for multiple monitored users.

FIG. 20 illustrates examples of timelines of detected coughs and motion in bed for multiple monitored users. Again here, timeline 1901 illustrates what movement state a user is determined to be in based on radar data generated by radar subsystem 120 and processed by radar processing module 1010. Timeline 1902 illustrates when a cough was detected by cough detector 1810 based on an audio stream from microphone 134.

During time period 1910, a cough is detected based on the audio stream and motion is detected by radar processing module 1010 for the first user. In such a circumstance, cough decision engine 1820 attributes the monitored first user with having coughed. Similarly, during time period 1940, a cough is detected based on the audio stream and motion is detected by radar processing module 1010 for the first user. Again here, cough decision engine 1820 attributes the monitored first user with having coughed. Data indicative of the cough, cough duration, timestamp of the cough, and cough severity may be stored to cough data storage 1825 as mapped to the first user.

During time period 2010, a cough is detected based on the audio stream and motion is detected by radar processing module 1010 for the second monitored user as indicated on timeline 2001. In such a circumstance, cough decision engine 1820 attributes the monitored second user with having coughed. Data indicative of the cough, cough duration, timestamp of the cough, and cough severity may be stored to cough data storage 1825 as mapped to the second monitored user.

During time period 2020, a cough is detected based on the audio stream but no motion of either monitored user is detected that is sufficient to classify the user as moving within bed. Therefore, the cough of time period 2020 is not mapped to either monitored user. During time period 1930, despite the first user moving within bed, because no cough is detected based on the audio stream, no indication of a cough is stored for either user. In some circumstances, a user may cough intensely enough that it causes both users to move (by the coughing user shaking the bed, which causes the other user to move). In such a circumstance, the user with the greater amount of movement in bed may be attributed with the cough.

It should be understood that timelines 1901, 1902, and 2001 are examples only. The number of coughs detected, whether one or more users are monitored, and the timing of coughs would vary based on the particular situation.

Figure 21:
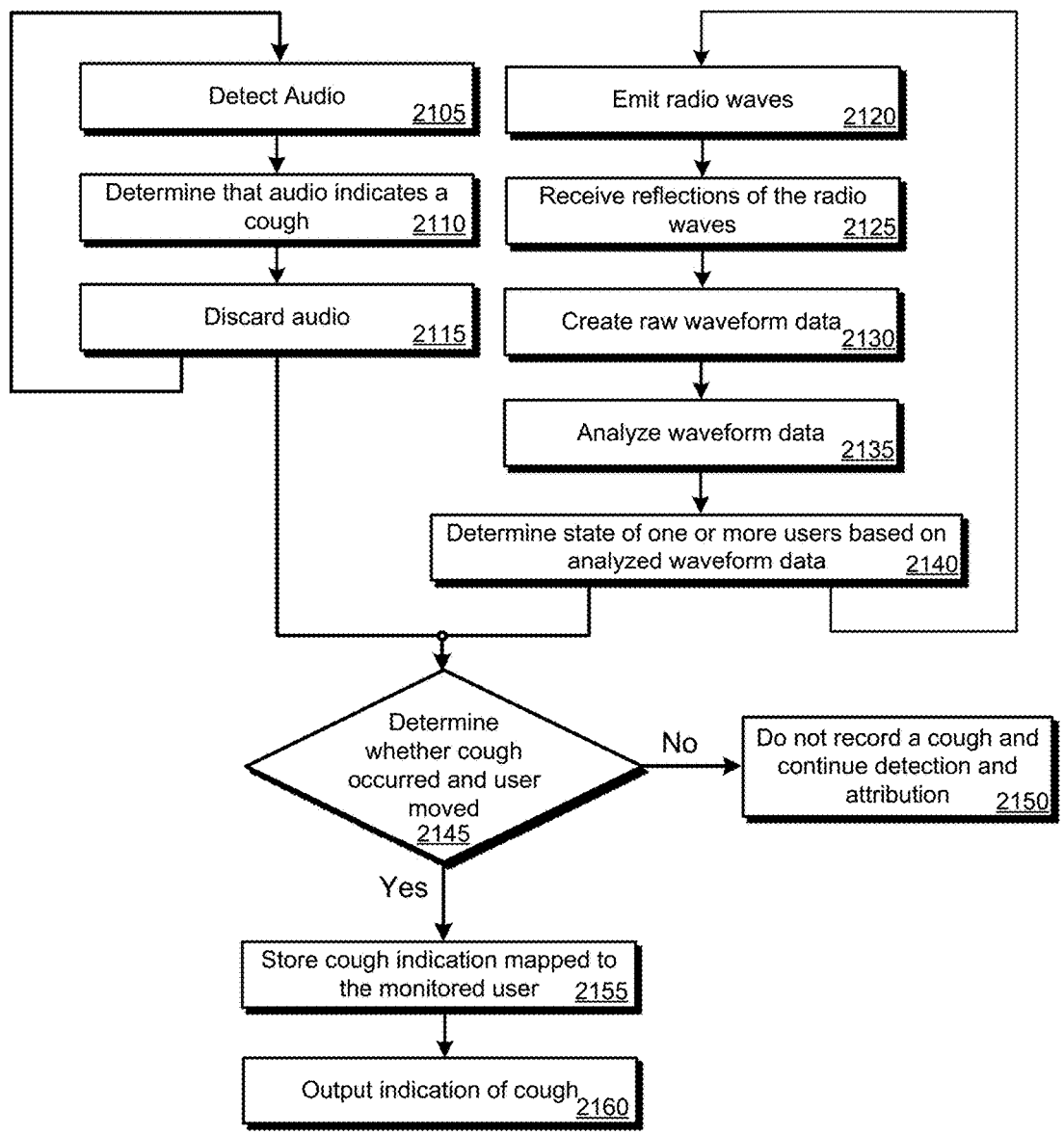
FIG. 21 illustrates an embodiment of a method for cough detection and attribution.

Various methods for cough detection and attribution may be performed using cough attribution system 1800. FIG. 21 illustrates an embodiment of a method 2100 for cough detection and attribution. Method 2100 may be performed using cough attribution system 1800 or some other similar system. Further, cough attribution system 1800 may be incorporated as part of device 300. For instance, cough attribution system 1800 may be used with radar processing module 210 when a single user is being monitored for coughs. System 1800 may be used with radar processing module 1010 if two users are being monitored for coughs. Cough attribution system 1800 can, additionally or alternatively, be used in conjunction with a beam-steering module, such as beam-steering module 230, beam-steering module 1410, or beam-steering module 1610 in order to perform beam-steering in the direction of where the user or users are in bed. Further, it should be understood that cough detection and attribution can be performed in conjunction with sleep tracking or separately from sleep tracking. For instance, cough detection and attribution can be performed along with various embodiments of method 800, method 1300, and/or method 1700. Alternatively, method 2100 can be performed as a stand-alone method separate from methods 800, 1300, and 1700. If method 2100 is performed as a stand-alone method by device 300, device 300 can be referred to as a contactless cough detection and attribution device. Notably, due to using radar and audio, method 2100 can perform cough detection and attribution without any device making physical contact with the monitored user or a bed of the monitored user.

In method 2100, two separate processes may be performed in parallel: an audio monitoring process may be performed in blocks 2105 through 2115 and a radar-based movement monitoring process may be performed in blocks 2120 through 2140. Both of these processes can be performed repeatedly and continuously as part of method 2100. At block 2105, audio is detected using one or more microphones. In some embodiments, such one or more microphones are located on-board the device performing method 2100 or a remote device that has one or more on-board microphones may be used and an audio stream may be transmitted to a cough detection and tracking device for analysis. For instance, the remote device may be a separate home assistant or smart speaker device. At block 2110, the audio stream output by the microphone is analyzed to determine if a cough has occurred. Detection of the cough may be performed using a pre-trained machine-learning module, which may be a trained neural network. In some embodiments, cough detection is performed exclusively based on audio. If a cough is detected, an output may be created that indicates a cough is present and a timestamp of the cough.

At block 2115, the audio stream created by the microphone might be deleted or otherwise discarded. In some embodiments, no portion of the audio stream is saved (other than an indication of whether or not a cough was present in the audio stream). If the device performing method 2100 can function as a home assistant, the audio stream can be temporarily stored if the user speaks a keyword or key phrase that is intended to trigger the user's speech to be interpreted as a command or question.

At block 2120, radio waves are emitted. The radio waves emitted can be continuous-wave radar, such as FMCW. The FMCW radar can transmit radio waves as detailed in relation to FIG. 2C. The radio waves may be emitted by RF emitter 206 of radar subsystem 205. At block 2125, reflections of the radio waves may be received, such as by multiple antennas of RF receiver 207 of radar subsystem 205. The reflections received at block 2125 may be reflected off of moving objects (e.g., a person sleeping in bed, a person moving in bed) and stationary objects. Blocks 2120 and 2125 can correspond to blocks performed as part of one or more of the other methods detailed herein, such as blocks 805 and 810 of method 800 and/or blocks 1705 and 1710.

At block 2130, raw waveform data, which can also be referred to as raw chirp waterfall data, is created based on the received reflected radio waves and is output by the radar subsystem. Over time, a window of raw waveform data may be created and stored in a buffer for analysis. Prior to waveform data being provided to a radar processing module for processing, waveform data may be processed using a beam-steering module to perform a beam-steering process, such as WDAS beam-steering. For instance, blocks of method 1700 may be performed at block 2130.

At block 2135, the raw waveform data, which may have been weighted based on beam-steering, is analyzed at block 2135. Analysis at block 2135 can be performed in accordance with the processing detailed in relation to movement filter 211, frequency emphasizer 212, range-vitals transform engine 213, range gating filter 214, spectral summation engine 215, and neural network 216. As detailed in relation to radar processing module 1010, if multiple users are being monitored, each user may be mapped to an instance of spectral summation engine and the neural network.

At block 2140, based on the output from neural network 216, a state may be determined for the user or each user. The state may be determined in accordance with state machine 500. Therefore, the output of block 2140 may be an indication of whether the user is: in bed, and is moving in bed or is motionless (except for vital signs). If multiple users are being monitored, the output of block 2140 may be a similar indication for each user. A timestamp may be mapped to each determined state that is output. Following block 2140, the radar process may continue to repeat and monitor for movement.

At block 2145, a determination may be made as to whether the cough occurred within a predefined time range of the user moving. Timestamps mapped to an indication of the cough and an indication of user movement can be used to determine if a cough and user movement occurred sufficiently close in time such that the cough can be attributed with the movement. In some embodiments, in order for block 2145 to be determined in the affirmative, a cough is detected based on the audio and, within the predefined time range, the user is determined to be moving within bed (e.g., state 503). If either no cough is detected or the monitored user is not moving in bed, block 2145 may be evaluated in the negative. If multiple users are being monitored, block 2145 may be evaluated in the affirmative for one user and in the negative for the other users. It is also possible that block 2145 is evaluated in the negative for all users.

At block 2150, in some embodiments, no cough is attributed or recorded indicating that a monitored user has coughed. In some embodiments, if the user was detected as having moved in bed (but not coughed) and sleep tracking is being performed, an indication of the user's movement in bed can be stored for sleep tracking purposes. Following block 2150, the audio monitoring process and the radar-based movement monitoring process may continue to be performed to detect and attribute future possible coughs and block 2145 may continue to be evaluated in the future.

At block 2155, if block 2145 was determined in the affirmative, an indication that a cough has occurred may be mapped to the monitored user that coughed and stored. If multiple users are being monitored, the indication may be mapped to the particular monitored user that was determined to have coughed. In some embodiments, additional information about the cough may also be stored, such as: the duration of the cough; the number of coughs in a group of rapid coughs (e.g., a coughing fit); and the intensity of the cough. If multiple monitored users are present, while the cough may be mapped to a particular user, the cough may serve as an audio event that has caused the other user to wake as part of method 800. At the end of a night, none, one, several, or many stored cough indications may be present for a particular monitored user. Blocks 2105 through 2155 may be repeatedly performed throughout a night while a user is present in bed.

At block 2160, an indication of the cough stored at block 2155 may be output. Block 2160 can include a report being output, such as a nightly report, which includes cough data for the previous night. Therefore, block 2160 may be performed following cough detection and attribution concluding for a night, such as in the morning when a user or users are no longer detected as present in bed. The indication of a cough may be included in a generated report that indicates: a number of times the particular user coughed during the night; when the user coughed; how intense the user's coughs were; whether the coughs woke the user; etc. Such a report may be output in response to the user providing input to the cough detection and attribution device. The user may provide input via a touchscreen or the user may speak a command (possibly along with a trigger word or phrase) that requests the nightly report be output. In other embodiments, the nightly report may automatically be output at a particular time or when the user is determined to be awake or out of bed after a time of day (e.g., after 7 AM). The nightly report may be output using synthesized speech and/or text and/or graphics on a display of the cough detection and attribution device. If multiple users are being monitored, a separate report, or separate data may be output for each user. A report that combines data for the multiple users is also possible.

Nightly report data may be transmitted to, stored by, and/or analyzed by a remote cloud-based server system. In some embodiments, each cough indication of block 2155 may be transmitted to the cloud-based server system for storage and analysis. Alternatively, in some embodiments, data from the generated report may be transmitted to and stored by the cloud-based server system. A user may have the option to prevent any cough-related data from being transmitted to the cloud-based server system. In some embodiments, the nightly report may be generated by the cloud-based server system and stored as mapped to a user account such that the report can be accessed via one or more other devices (e.g., a smartphone) of the user that have access to the user account.

The cloud-based server system or the cough detection and attribution device may also produce long-term trend data using the stored cough indication. Such long-term trend data may be indicative of cough trends for the monitored user over a time period such as: multiple nights, a week, several weeks, a month, several months, a year, several years, etc. The long-term data may indicate: whether the monitored user's frequency of coughing is increasing, decreasing, or staying approximately constant over the time period; whether the monitored user's intensity of coughing is increasing, decreasing, or staying approximately constant over the time period; whether the monitored user's duration of coughing is increasing, decreasing, or staying approximately constant over the time period. Long-term trend data may be maintained separately for each monitored user.

Similarly to the nightly report data, the user may provide input via a touchscreen or the user may speak a command (along with a trigger word or phrase) that requests the long-term trend data be output. In other embodiments, the long-term trend data may be output at a particular time or when the user is determined to be awake after a defined time (e.g., after 7 AM). In some embodiments, the long term trend data is output as part of the nightly report. In some embodiments, the long-term trend data is output in response to when a change in the long-term trend data is identified as present, such as a change in the frequency at which the user is coughing has increased over time. The long-term trend data may be output using synthesized speech and/or text and/or graphics on a display of the cough detection and attribution device. If multiple users are being monitored, separate long-term trend data may be output for each user or a combined long-term report can be generated.

The nightly report and/or long-term trend data for coughing may be output in conjunction with a sleep report for the one or more users. A single report may be output that indicates sleep data and coughing data for a user. For instance, in the morning, a user may view a single report that includes data on the user's sleep from the previous night and data about the user coughing. Long-term sleep and/or cough data may be incorporated as part of the report. Such reports may be stored using the cloud-based server system mapped to a user account to permit access by the user to the data from a separate device.

In some embodiments, one or more recommendations may be output if the user's frequency of coughs is relatively high or increasing. For instance, if the cough attribution device (or another smart device in the vicinity) measures humidity using a humidity sensor, a recommendation may be output that the humidity level be raised in the room where the user sleeps if the measured humidity is below a threshold value (or some other form of determination that uses a threshold criterion at least partially based on humidity) on nights that the user tends to cough. Another recommendation may be that the user seek medical attention, such as in response to a long-term increase in coughing.

Figure 22:
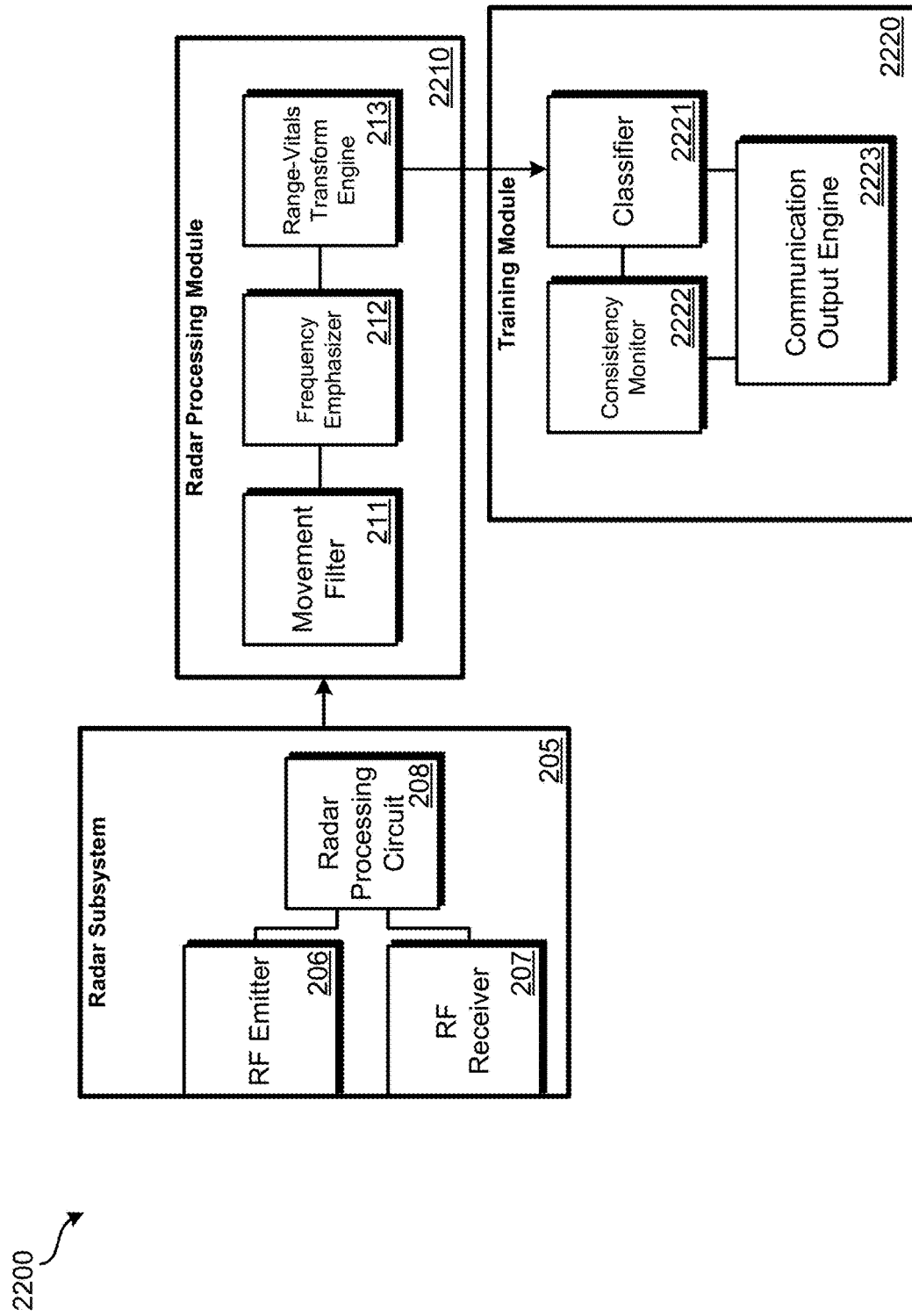
FIG. 22 illustrates an embodiment of a sleep tracking system that performs a sleep setup process.

To perform sleep tracking, cough detection and attribution, and/or other forms of health monitoring or tracking, a setup process may be performed to help ensure that a user has positioned the device appropriately and that the ambient environment is configured in such a way as to permit the device to operate properly. Without a setup process being performed, the sleep tracking device may be less likely to be aimed correctly in the direction of where the user sleeps, be located at an acceptable distance, and/or that moving objects in the vicinity of the user have been removed. FIG. 22 illustrates an embodiment of a sleep tracking system 2200 that performs a sleep setup process. It should be understood that a similar setup process may be performed for a cough attribution device or other form of health monitoring or health tracking device. Sleep tracking system 2200 can represent an embodiment of system 200A of FIG. 2A. Sleep tracking system 2200 can be incorporated as part of contactless sleep tracking device 300 or some other stand-alone, contactless health tracking or monitoring device. Sleep tracking system 2200 may also be used to perform a setup process ahead of cough detection and attribution being performed. Prior to sleep tracking or cough detection and attribution being setup, some components of radar processing module 210 may be active. Radar processing module 2210 represents a subset of the components of radar processing module 210 that can be used to perform the setup process. Movement filter 211, frequency emphasizer 212, and range-vitals transform engine 213 can function as detailed in relation to system 200A. Training module 2220 may use the output of range-vital transform engine 213 from radar processing module 2210.

Training module 2220, similar to radar processing module 2210, may be implemented as software executed using one or more general-purpose processors. In other embodiments, dedicated hardware can be used to execute functions of the components of training module 2220. In some embodiments, training module 2220 may be active prior to a sleep tracking setup process being successfully completed. In such embodiments, once completed, training module 2220 is deactivated and system 2200 can function as system 200A, system 200B, embodiment 1400, embodiment 1600, or system 1800. Alternatively, the system or user may reinitiate the setup process at some time after a successful setup process, such as if the sleep tracking device is having difficultly detecting a sleeping user, the device is repositioned, periodically, or at some other time in the future.

Training module 2220 can include classifier 2221, consistency monitor 2222, and communication output engine 2223. Classifier may receive the output of range-vital transform engine 213. Radar subsystem 205 and radar processing module 2210 may operate continuously regardless of whether the sleep tracking setup process has been performed. Upon a user providing input stating that a sleep tracking setup process is to be performed, training module 2220 may be activated. When training module 2220 is activated, classifier 2221 may begin outputting a classification based on the data received from radar processing module 2210, such as the output from range-vitals transform engine 213.

Range-vitals transform engine 213, as previously detailed, analyzes the received motion-filtered waveform data to identify and quantify the frequency, range, and magnitude of movement over time. Classifier 2221 receives as its input processed waveform data indicative of the magnitude of different observed frequencies at various distances.

Classifier 2221, prior to performing a classification, may discard waveform data indicative of movement at distances too close and/or too far from system 2200. In some embodiments, detected frequencies at a distance of less than 0.25 m or at a distance of greater than 1 m is discarded. In other embodiments, the minimum and maximum range distances may vary. For instance, the minimum distance can be between 0.1 and 0.5 m and/or the maximum distance may be between 0.7 and 1.5 m.

Classifier 2221 can analyze data in chunks of waveform data over time. That is, data from range-vitals transform engine 213, after discarding waveform data corresponding to movement too close or too far away, may be aggregated or summed over a time period, such as two seconds. In other embodiments, shorter or longer durations of time are used to create the data chunks, such as chunks that are 0.5 s to 5 s in duration. Classifier 2221 may analyze chunks in 1 s strides (a stride being the difference in time from when a first chunk beings until the next chunk begins), therefore, some amount of overlap can be present between chunks, such as 50%. In other embodiments, the stride may be greater or smaller, such as between 0.5 s and 5 s, which alters the amount of overlap.

Classifier 2221 may include a machine learning model, such as a trained neural network. The machine learning model receives each summed chunk of data (which includes frequency, magnitude, and range data) and outputs a classification selected from multiple possible classifications. In some embodiments, classifier 2221 outputs one of three possible classifications. The classification states may be indicative of: 1) no user present; 2) excessive movement; and 3) static user present. A classification of "no user present" corresponds to no user being detected. This classification may be indicative of the user being outside of the permissible range, the user not being present in the environment, or the device that includes system 2200 having its radar subsystem aimed away from the user. A classification of "excessive movement" can be indicative that the user is not lying still (e.g., the user is rolling in bed or otherwise moving) and/or that one or more other objects are present and moving in the monitored region. Such objects may be fans, clocks (e.g., that include a pendulum), moving water, moving fabric (e.g., curtains moving due to airflow), a plant (e.g., leaves rustling due to airflow), or some other type of moving object. A classification of "static user present" may be indicative of a user being detected that is not moving. By not moving, the user can be laying still, but still exhibiting vital signs, such as slight movements due to the user breathing and the user's heartbeat. Slight muscle movements (e.g., a twitch of a finger or arm, a deep sigh) may be tolerated by the machine learning model and classification of "static user present" may still be returned.

Classifier 2221 may include a pre-trained neural network model that analyzes two or three features received from range-vitals transform engine 213. The features may be selected from the group of frequency, magnitude, and range. It should be understood that in other embodiments, fewer or greater numbers of features may be used to perform a classification. In other embodiments, fewer or greater numbers of classification states may be determined by classifier 2221. Further, in other embodiments, different classification arrangements, both those that use other forms of machine-learning and non-machine-learning arrangements, are used. The machine learning model may be trained using a set of truth-tagged features (e.g., frequency, magnitude, and/or range) that have been accurately mapped to the desired state for those features. For example, in a controlled environment a subject may be monitored and have the features properly classified by a sleep expert based on whether the subject is motionless, moving, or not present.

In some embodiments, classifier 2221 can use processes other than machine-learning models. For instance, classifier 2221 may determine whether movement is present due to breathing being detected but little, if any, other movement being detected. Therefore, if based on the frequency and magnitude data received from range-vital transform engine 213, a determination is made that a frequency between ten and sixty hertz is present (or some other range for a specific age as indicated in Table 1) and no other significant amount of movement is observed (besides, possibly, movement due to a heartbeat), a classification of "static user present" may be determined and output. If magnitudes above a defined threshold (or some other form of determination that uses a threshold criterion at least partially based on magnitude) are observed at multiple frequencies, a determination of "excessive movement" may be output. If no magnitude over a defined threshold is detected, a determination of "no user present" may be output. In other embodiments, rather than using breathing, another vital sign is detected, such as the user's heartbeat and used to determine a classification. Breathing may be preferable since a user's chest moves a greater amount due to breathing than the user's heart beating.

Classifier 2221 may output a single classification at any given time while classifier 2221 is active. In some embodiments, if, after a defined time limit (or some other form of time-based criterion) after the sleep tracking setup process has begun, such as between five and 20 seconds, the classification of "static user present" has not yet been output by classifier 2221, the setup process does not complete successfully. In such a situation, communication output engine 2223 can provide feedback to a user that setup of sleep tracking has failed and, possibly, may provide recommendations on how to improve the chances for success in a future performed setup process. If the classification of "excessive movement" has been identified by classifier 2221, a recommendation may be made for the user to attempt to remove extraneous movement from the environment, such as moving objects or the user himself should refrain from moving. If the classification of "no user present" is output by classifier 2221 during the failed setup process, the user may be reminded of the distance that the user should be located from radar subsystem 205 and/or the user may be reminded of how radar subsystem 205 should be pointed in relation to where the user sleeps.

If classifier 2221 does output a classification of "static user present" prior to the time limit period expiring, this may serve as an indication that the user has properly laid in bed, is being detected, and the user's environment is sufficiently motionless for proper sleep, cough, or health monitoring and tracking. This initial classification of "static user present" can serve as a trigger to begin a consistency check performed by consistency monitor 2222. The purpose of consistency monitor 2222 may be to ensure that the user, while lying in bed, is properly detected as "static user present" for a sufficient portion of time such that future monitoring of the user while sleeping will likely yield usable vital statistic and/or health monitoring data. For example, while "static user present" may have been initially observed by classifier 2221, this classification may have been transient, such as due to movement of curtains that have temporarily and sufficiently stopped moving, over the defined time period. In such a situation, despite the temporary classification of "static user present," it is possible that excessive movement may be detected due to airflow resuming that negatively affects accurate monitoring of a user.

Over a period of time, such as five two second chunks, consistency monitor 2222 can determine if classifier 2221 has output "static user present" for a sufficient portion of the time period. For instance, if the time period is 10 seconds, in a 10 second window, classifier 2221 may be required to output "static user present" for seven seconds, some number of chunks, or some other threshold portion of the time period (or some other form of determination may be performed that uses a threshold criterion at least partially based on the amount of time for which classifier 2221 is outputting particular state classifications).

If consistency monitor 2222 determines that "static user present" was output by classifier 2221 for at least a threshold amount of the time period (or, again, uses some other form of threshold criterion based at least partially based on the amount of time in the given states), communication output engine 2223 may indicate that the sleep tracking setup has completed successfully and that sleep tracking is now properly setup and activated. A graphical (e.g., via display 140) and/or auditory output (e.g., via speaker 155) may be provided to the user indicating that setup has successfully been completed. Whenever the user is present in bed going forward, the user's sleep may be tracked. Such tracking may automatically begin based on the user being detected with the bed. With setup successfully completed, training module 2220 may be deactivated and system 2200 may transition to function as systems 200A, 200B, 1000, and/or 1800.

If consistency monitor 2222 determines that "static user present" was not output by classifier 2221 for at least a threshold portion of the time period (or some other form of threshold criterion-based analysis on the amount of time in the given state), communication output engine 2223 may indicate that the sleep tracking setup was not completed successfully and that sleep tracking has not be activated. Since the user was previously identified by classifier 2221 as in bed and still, a failure at this point will likely be due to "excessive movement" being output for a significant period of time by classifier 2221, such as due to the user rolling over, moving, or some other object nearby moving. A graphical (e.g., via display 140) and/or auditory output (e.g., via speaker 155) may be provided to the user by communication output engine 2223 indicating that setup failed. A recommendation may be output that the user retry sleep tracking setup, remain still in bed, and remove any moving objects from the environment.

In some embodiments, consistency monitor 2222 may additionally monitor for variances in the distance at which the user is detected (e.g., based on breathing being detected). If the variance in distance at which the user is observed changes more than a distance threshold (or some other form of determination that uses a threshold criterion at least partially based on distance), consistency monitor 2222 may continue to monitor the user to see if the variance decreases over time. If the variance does not decrease by a defined time limit (e.g., 30 seconds) being reached or by some other time-based criterion, the sleep tracking setup process can fail. If the variance in distance at which the user is observed is an acceptable amount, the setup process can be eligible to successfully complete.

Figure 23:
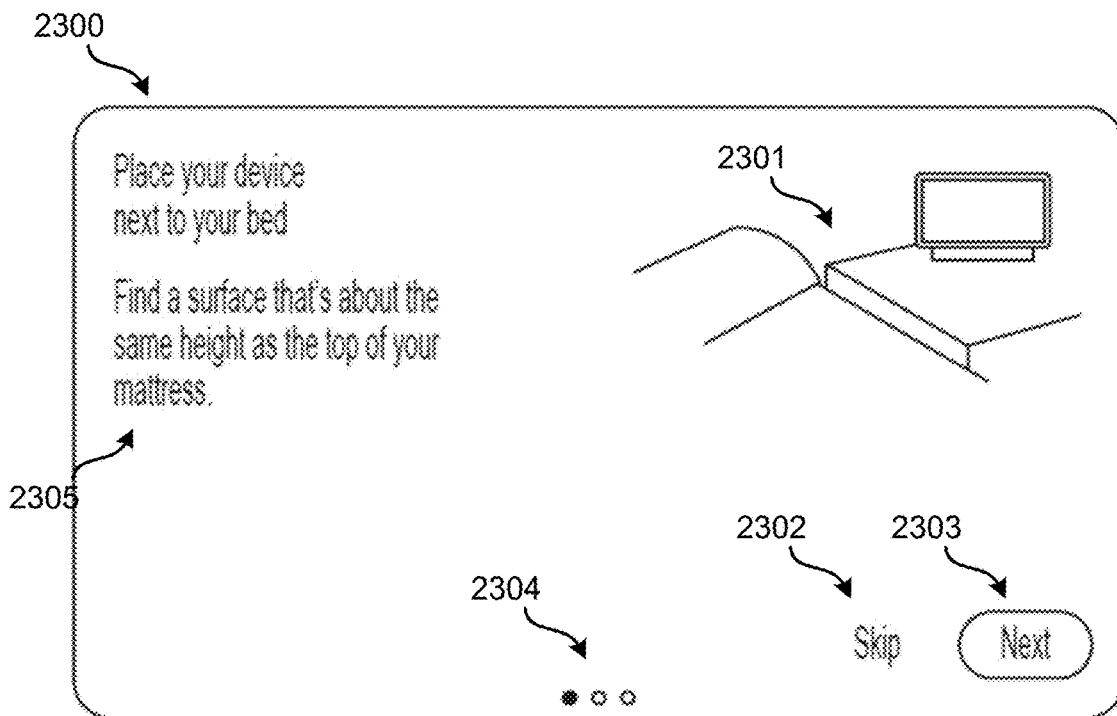
FIG. 23 illustrates an embodiment of a first instructional user interface presented during a sleep setup process.

FIG. 23 illustrates an embodiment of an instructional user interface 2300 presented during a sleep setup process. Instructional user interface 2300 can be presented using a display screen of device 300 (in which system 2200 may be incorporated). Instructional user interface 2300 can be presented in response to a user providing input (e.g., making a selection on the touchscreen, speaking a verbal command) indicating that the user desires to perform a sleep or health monitoring setup process. In some embodiments, "setup" can instead be referred to as "calibration" since the user is potentially moving the device, other objects, and/or their own sleeping position in order to successfully complete the setup process. Diagram 2301 may be presented as part of instructional user interface 2300 to indicate the general positioning and orientation in which device 300 and the user's bed should be arranged. The user may be permitted to skip additional instructions to proceed directly to setup via touch element 2302 or proceed to the next instruction user interface via touch element 2303. Page indicator 2304 may indicate the number of instruction interfaces and the current instruction user interface being presented (in this example, one of three) by virtue of a number of elements and which element is emphasized. Written instructions 2305 can indicate how the user should arrange the device in relation to the user's bed. Written instructions 2305 can also be output via synthesized speech while instructional user interface 2300 is presented.

Figure 24:
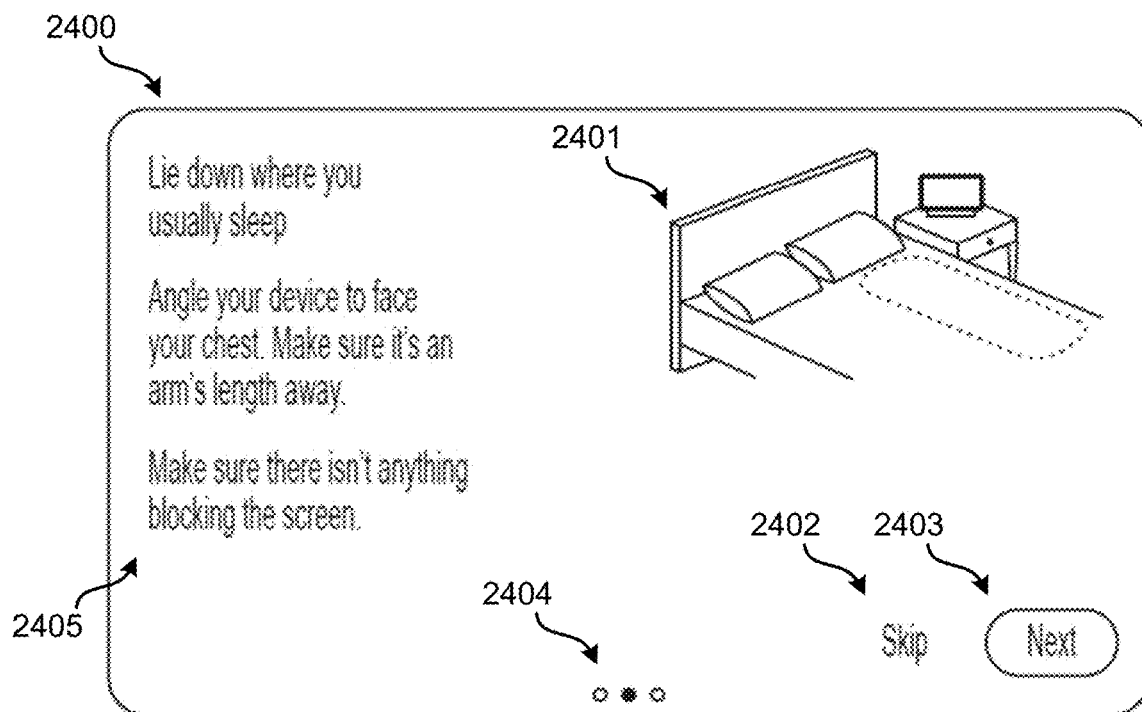
FIG. 24 illustrates an embodiment of a second instructional user interface presented during a sleep setup process.

FIG. 24 illustrates an embodiment of an instructional user interface 2400 presented during a sleep setup process. Instructional user interface 2400 can be presented using a display screen of device 300 (in which system 2200 may be incorporated). Instructional user interface 2400 may be presented following a user providing input (e.g., via touch element 2303, via a voice command) to proceed to the next instructional user interface from instructional user interface 2300. Diagram 2401 may be presented as part of instructional user interface 2400 to indicate, such as in greater detail than diagram 2301, a position and orientation in which device 300, the user's bed, and the user's sleeping position should be arranged in relation to each other. The user might be permitted to skip additional instructions to proceed directly to setup via touch element 2402 or the user can proceed to the next instruction user interface via touch element 2403. Page indicator 2404 can indicate the number of instruction interfaces and the current instruction user interface (in this case, two of three) being presented by virtue of a number of elements and which element is emphasized. Written instructions 2405 can indicate how the user should position himself relative to the device in bed and/or ensure no objects are blocking a path directly from the user's chest to the device. Written instructions 2405 may also be output via synthesized speech while instructional user interface 2400 is presented.

Figure 25:
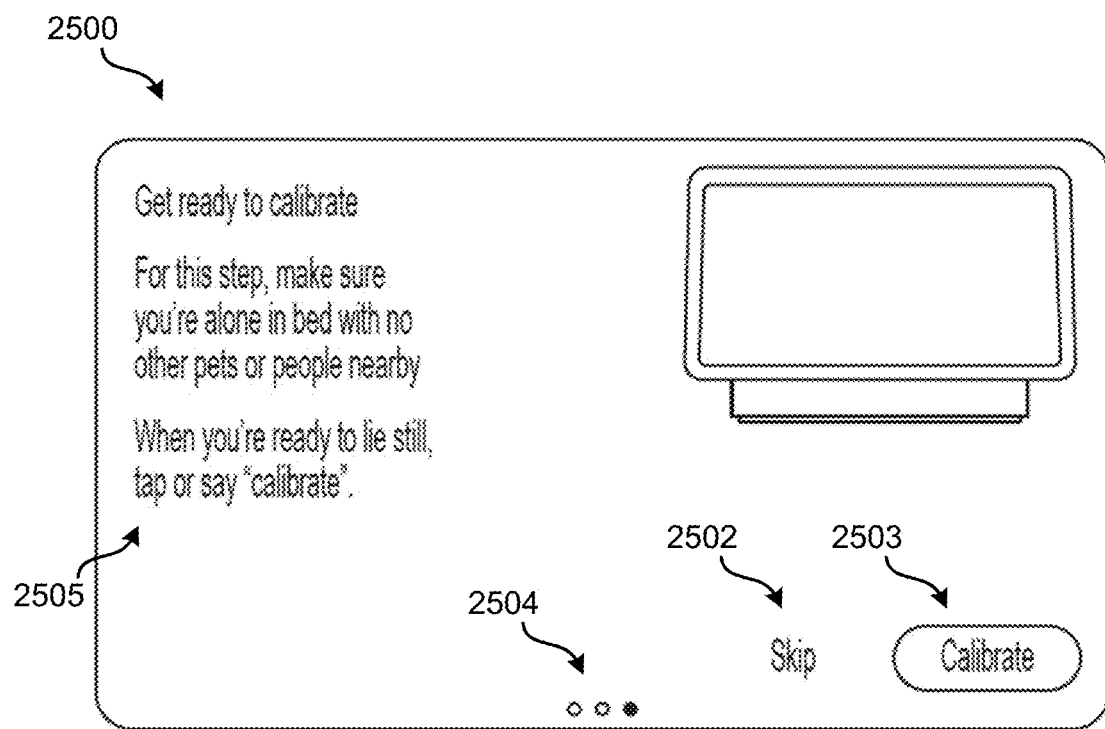
FIG. 25 illustrates an embodiment of a third instructional user interface presented during a sleep setup process.

FIG. 25 illustrates an embodiment of an instructional user interface 2500 presented during a sleep setup process. User interface 2500 can be presented using a display screen of device 300 (in which system 2200 may be incorporated). User interface 2500 may be presented following a user providing input (e.g., via touch element 2403, via a voice command) to proceed to the next instructional user interface from instructional user interface 2400. The user may be permitted to skip additional instructions (and/or the setup process entirely) via touch element 2502 or proceed to setup measurements being captured via touch element 2503. Notably, rather than touching touch element 2503, a user may be encouraged or required to use a verbal command to start setup. Using a verbal command, such as "setup," may help allow the user to remain still, apart from breathing, during setup. That is, when such a verbal command is provided, the user does not need to move their arm and hand to provide a touch input to trigger the start of the setup measurements. Page indicator 2504 may indicate the number of instruction interfaces and the current instruction user interface being presented by virtue of a number of elements and which element is emphasized (in this case, the third of three interfaces). Written instructions 2505 may indicate how the user should be in bed, alone, and ready to start setup. Written instructions 2505 may also be output via synthesized speech while user interface 2500 is presented.

Figure 26:
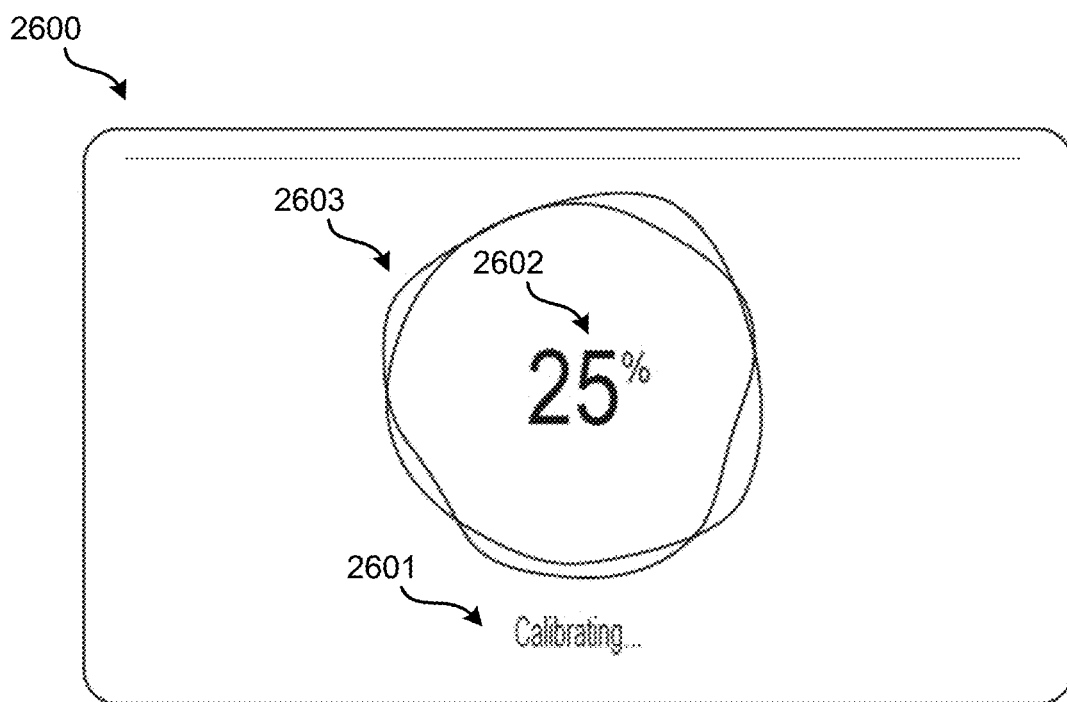
FIG. 26 illustrates an embodiment of a user interface presented during a sleep setup process.

FIG. 26 illustrates an embodiment of user interface 2600 presented during the sleep setup process being performed. User interface 2600 may be presented using a display screen of device 300 (in which system 2200 may be incorporated). User interface 2600 may be presented in response to a user triggering the setup process, such as using a voice or touch command via touch element 2503, from instructional user interface 2500.

A written indication 2601 may be presented that indicates contactless setup measurements are being performed. User interface 2600 can include indicator value 2602 that indicates of how much (e.g., what percent) of the setup process has been performed. In the example of user interface 2600, 25% is complete. Indicator value 2602 may indicate for each percent or at various rounded values, such as every 5%. Visually, animation 2603, or some other animation may be presented to indicate to the user that the device is functioning and provide a visually pleasing effect. Animation 2603 may change color over time. Animation 2603 may have multiple circular shapes that each have perimeters that fluctuate in a sinusoidal pattern over time. A gradient that decreases in intensity towards the center of animation 2603 from the perimeters of the multiple circular shapes may be present. Further, a second gradient may be present that decreasing in intensity away from the center of the circular shapes.

In some embodiments of user interface 2600, audio may be output while user interface 2600 is presented. The audio may serve to indicate to a user, to whom user interface 2600 may be difficult to see due to the user laying down in bed, that the setup process is being performed. The audio may include music, such as relaxing instrumental music. When the music ends and an additional sound can be output, such as a ding, from which the user may infer that setup is complete. Additionally or alternatively, synthesized speech may be output that indicates that setup is being performed. When setup is complete, synthesized speech may be output indicating that setup is complete. The next user interface presented may be dependent on whether the setup process successfully completed or not.

Figure 27:
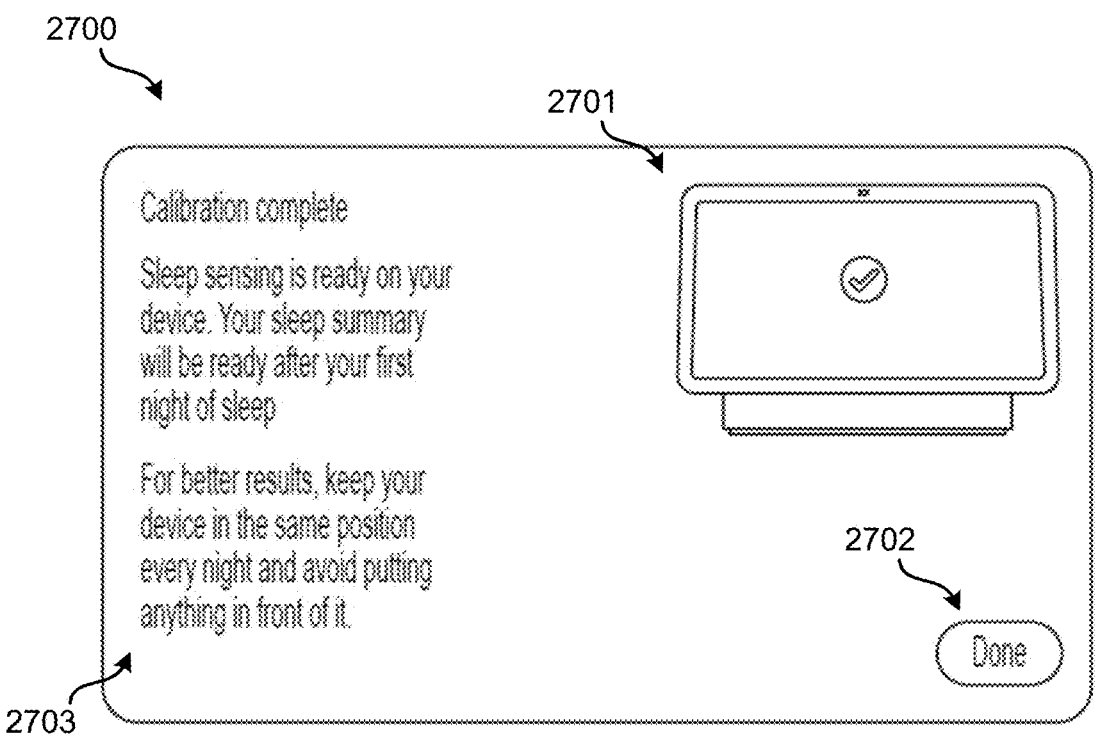
FIG. 27 illustrates an embodiment of a user interface presented following a successful sleep setup process.

FIG. 27 illustrates an embodiment of a user interface 2700 presented following a successful setup process. User interface 2700 may be presented using a display screen of device 300. User interface 2700 may be indicative that the sleep tracking process (or some other health monitoring process) has been successfully completed. User interface 2700 may be presented following user interface 2600 if setup was successfully completed. Specifically, user interface 2700 may be output by communication output engine 2223 when consistency monitor 2222 has successfully completed the consistency check. Diagram 2701 may be graphically indicative of the device being ready. Touch element 2702 may allow a user to proceed to a next item for setup or return to a home screen of the device. Notification 2703 may indicate that the device is now ready for sleep (and/or cough, and/or, more generally, for health) tracking and/or provide one or more tips for good results. Synthesized speech may be output that states the contents of notification 2704 while user interface 2700 is being presented.

Figure 28:
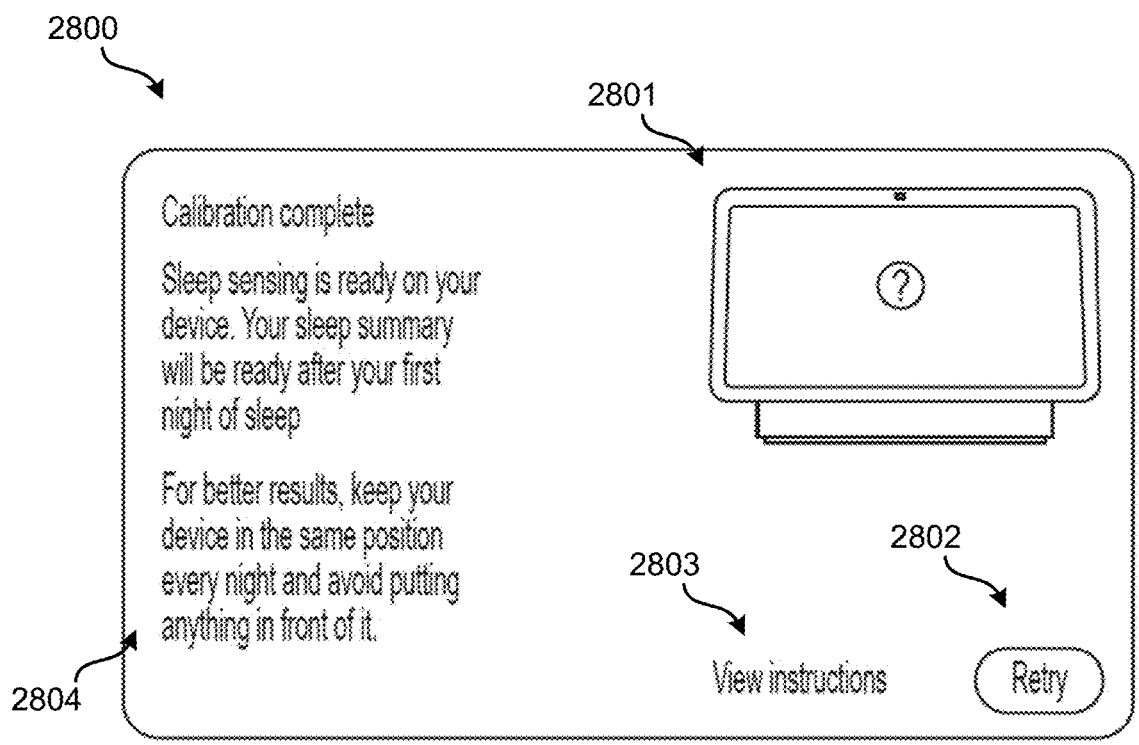
FIG. 28 illustrates an embodiment of a user interface presented following an unsuccessful sleep setup process.

FIG. 28 illustrates an embodiment of user interface 2800 presented following an unsuccessful sleep setup process. Therefore, user interface 2800 may be presented following user interface 2600. User interface 2800 may be presented using a display screen of device 300. User interface 2800 may be indicative that the sleep tracking setup (or other health tracking setup) process has not been successfully completed. User interface 2800 may be indicative of a "no user present" state has been detected by classifier 2221. Since the likely cause is that the user is too close or too far from device 300, the user may receive a distance recommendation in instructions 2804, such as that the user be less than an "arm's length" from the device. Synthesized speech may be output that states the contents of instructions 2804 while user interface 2800 is being presented. Graphical status indicator 2801 may be indicative of the device requiring additional input from the user. Touch element 2802 may permit a user to retry the setup process. Touch element 2803 may permit a user to review the instructions presented in instructional user interfaces 2300-2500.

Figure 29:
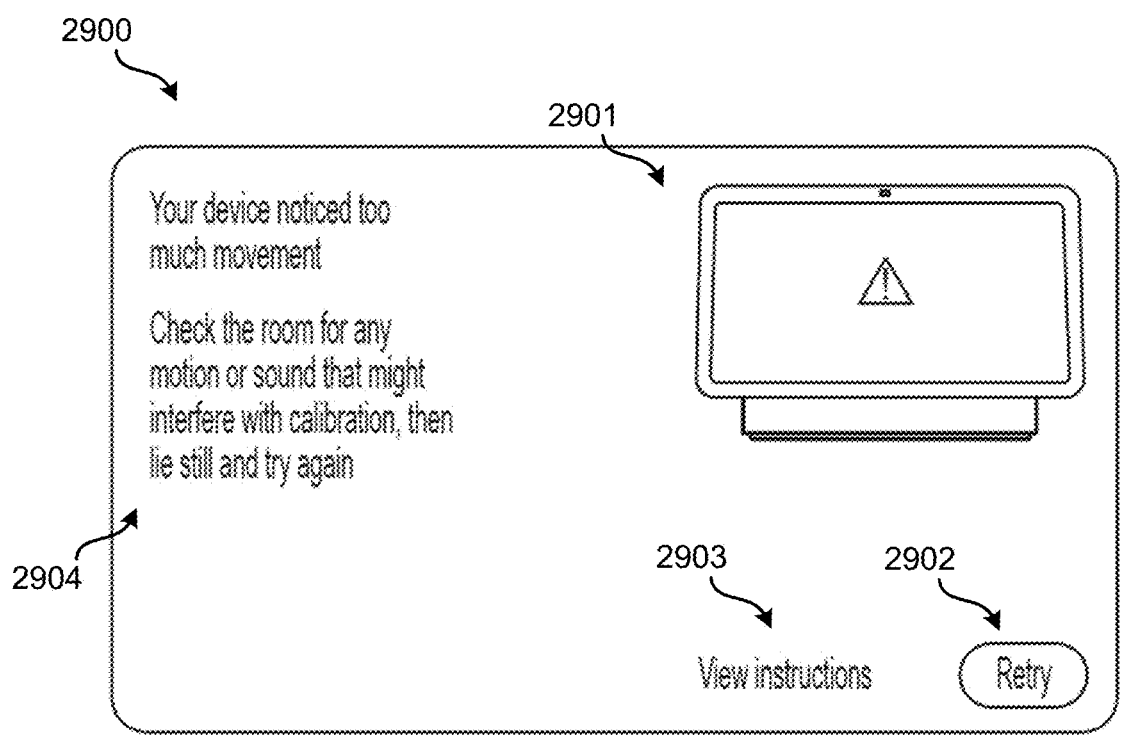
FIG. 29 illustrates another embodiment of a user interface presented following an unsuccessful sleep setup process.

FIG. 29 illustrates another embodiment of a user interface 2900 presented following an unsuccessful sleep setup process. Therefore, user interface 2900 may be presented following user interface 2600. User interface 2900 may be presented using a display screen of device 300. User interface 2900 may be indicative that the sleep tracking setup process has not been successfully completed. User interface 2900 may be presented when a "excessive movement" classification has been detected by classifier 2221 (and no "static user present" classification has been output) or that consistency monitor 2222 has detected an excess of the "excessive movement" classification over a time period. Since the likely cause is that the user is moving too much or another object nearby is moving, the user may receive recommendation on how to rectify the situation in instructions 2904, such as by laying still and removing moving objects from the general area. Synthesized speech may be output that states the contents of instructions 2904 while user interface 2900 is being presented. Graphical status indicator 2901 may be indicative of the device requiring additional input from the user. Touch element 2902 may permit a user to retry the setup process. Touch element 2903 may permit a user to review the instructions presented in instructional user interfaces 2300-2500.

For any of interfaces 2300-2900, synthesized speech may be output that corresponds to the text presented. Therefore, a user who is lying in bed may be made aware of the status of the sleep tracking setup process without the user physically needing to move their head to see the display screen. The synthesized speech output may match or may differ somewhat from the text presented on the display screen.

It should be understood that for any of interfaces 2300-2900, fewer or greater numbers of elements may be presented. Further, elements may be rearranged or contain varying instructions based on how the device should be setup.

Figure 30:
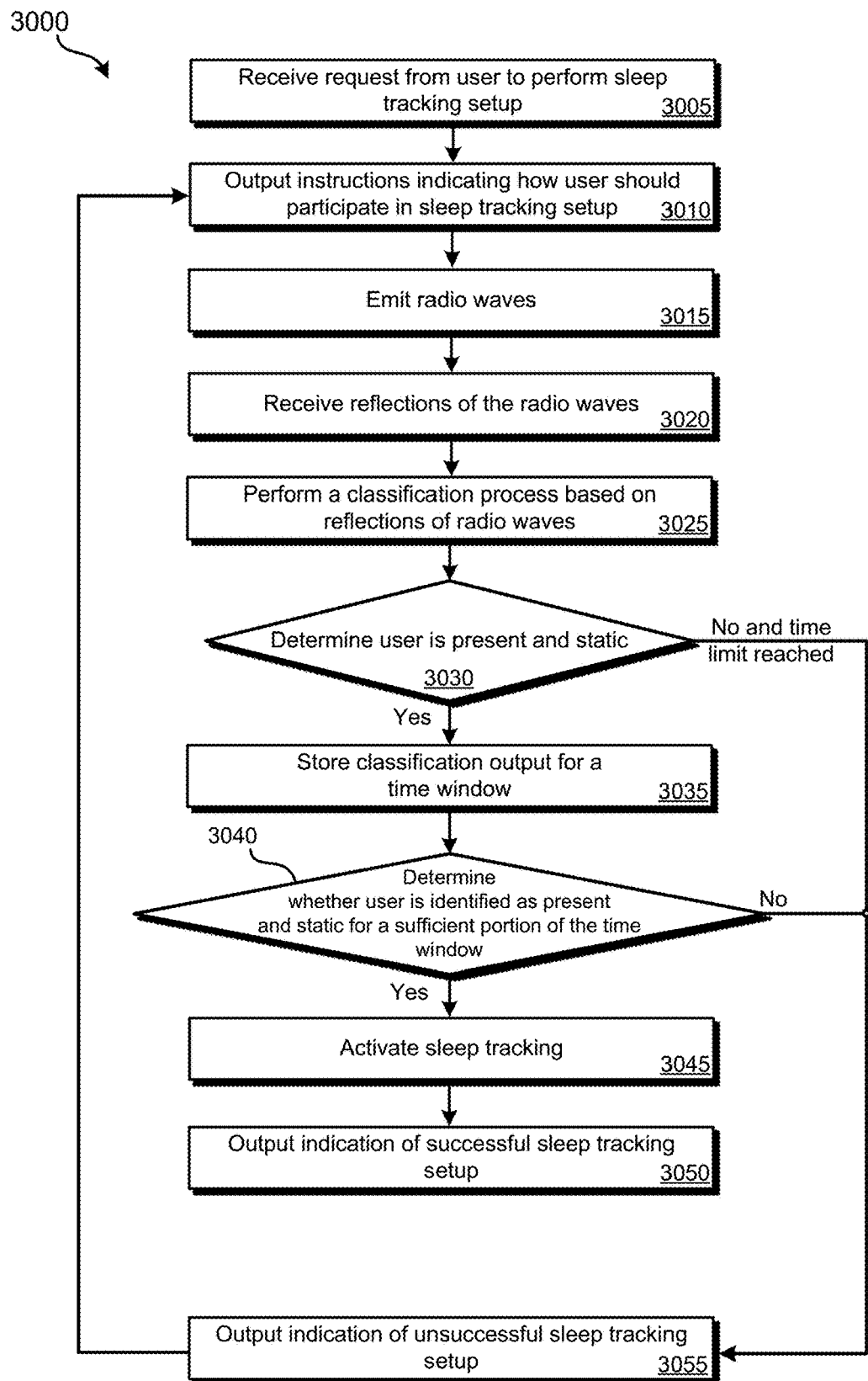
FIG. 30 illustrates an embodiment of a method for performing an initial setup process of a sleep tracking device.

Various methods may be performed using system 2200 and the graphical user interfaces of FIGS. 23-29. FIG. 30 illustrates an embodiment of method 3000 for performing an initial setup process of a sleep tracking device. However, method 3000 may also be used for performing a setup of some other form of health monitoring or tracking device, such as for cough detection and attribution. Method 3000 may be performed using system 2200, which may be implemented on system 100 and/or device 300. Method 3000 may be performed prior to blocks of other methods detailed herein in order to facilitate a setup process before a user performs sleep, cough, or some other form of health monitoring or tracking.

At block 3005, a user can provide a request, such as via voice or touch input, indicating that the user desired to perform a sleep tracking setup process. In some embodiments, the device may graphically present an interface that requests the user perform such a process and requests the user's consent to continue. The user can be required to provide input acknowledging that the user does indeed desire sleep tracking to be setup and the user is willing to participate in the setup process. The user may be given the option of skipping the setup process (but still enabling sleep, cough, and health tracking). Such an option can be desirable when an expert, such as a user who has used the device before or an installation professional, is using the device and does not need assistance in calibrating the relative positions of the user, device, and the user's sleeping position. The user may be given the option of disabling sleep, cough, and/or health tracking and forgo the setup process. If selected by the user, method 3000 concludes following block 3005 and such features would be disabled.

Following the user requesting sleep tracking setup be performed, block 3010 may be performed. At block 3010, instructions may be output, via the display screen and/or via synthesized speech, that indicates how the device should be positioned relative to where the user sleeps, how far away the user should be located from the device, and that the user should remove moving objects from the user's immediate environment.

At block 3015, radio waves are emitted by the radar subsystem of the system or device performing method 3000. Therefore, no physical contact with the user is made by any object to perform sleep tracking (or other form of health monitoring). In some embodiments, radio waves may begin being emitted at block 3015; in other embodiments, radio waves may have already begun being output by the device regardless of whether the sleep tracking setup process is initiated. The radio waves emitted may be continuous-wave radar, such as FMCW. The radio waves emitted at block 805 may be emitted in accordance with the FMCW radar scheme of FIG. 2C. The radio waves are emitted by RF emitter 206 of radar subsystem 205. At block 3015, reflections of the radio waves are received, such as by multiple antennas of RF receiver 207 of radar subsystem 205. The reflections received at block 3020 are reflected off of moving objects (e.g., a person having a heartbeat and breathing) and stationary objects. An output of the radar subsystem based on the received reflected radio waves can be processed as detailed in relation to movement filter 211, frequency emphasizer 212, and range-vitals transform engine 213. The output of range-vital transform engine 213 may indicate measured frequencies, frequency magnitudes, and the distances at which those frequency magnitudes were measured.

At block 3025, a classification may be performed using a trained classifier based upon the frequency, frequency magnitude, and distance waveform data. The classification may be performed as detailed in relation to classifier 2221, such as using a machine learning model or by determining whether breathing is detected to the exclusion of other significant amounts of movement. One of three (or some other number) possible classifications may be output by the classifier. The desired classification at this point to continue the setup process is that the user is present and is static, which would be indicative of the user properly lying in bed and being motionless, except for movement due to the user's vital statistics. The classification determined at block 3025 may be evaluated at block 3030.

At block 3030, if the user is determined to be present and static based upon the classification of block 3025, method 3000 may proceed to block 3035. If the user is not evaluated to be present and static at block 3030, the classification of block 3025 may continue to be performed for a time, such as up until a time limit nor some other limiting time-based criterion. If, at any point during that time period, the user is identified as present and static, method 3000 may proceed to block 3035. Block 3030 may be evaluated in the negative if at no point before the time limit is reached (or the time-based criterion is reached) is a classification at block 3025 of the user being present and static made. If block 3030 is evaluated in the negative, method 3000 may proceed to block 3055.

At block 3055, an indication can be output that sleep tracking setup has failed and, possibly, one or more recommendations that the user should follow when trying setup again. If the predominant classification output at block 3025 is that no user is detected ("user not present"), an indication may be output that the user should re-aim the device toward where the user is sleeping and stay within a distance range that is permissible for the device. If the predominant classification output at block 3025 is that excessive movement is detected, an indication may be output that the user should try moving less and/or remove objects that are moving in the vicinity of the user. As part of block 3055, the user may be invited to retry the sleep tracking setup process. If the user retries, method 3000 may return to block 3010.

If block 3030 is evaluated in the affirmative, method 3000 may proceed to block 3035. At block 3035, block 3025 may continue to be performed such that a current classification is determined and stored. Over a window of time, a determination may be made at block 3040 whether the classifications stored at block 3035 indicate that the user is present and static for at least a defined threshold amount of the window of time (or some other time-based threshold criterion is met that indicates the user was sufficiently present and static). If not, method 3000 proceeds to block 3055. If block 3040 is determined in the affirmative, sleep tracking can be activated at block 3045. Sleep tracking and other health monitoring may then be automatically performed when the user is identified as present in bed (assuming the user has properly consented to such monitoring). Sleep tracking may be more likely to capture useful data since the user has conducted the sleep tracking setup process and ensured that the user sleeps the correct distance from the device, the device is aimed correctly, and moving objects near where the user sleeps have been removed.

At block 3050, an indication may be output to the user indicating that the sleep tracking was successfully setup. This can include an auditory message (e.g., synthesized speech) being output indicating the success and/or a graphical user interface being presented that indicates that setup was successful.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A contactless sleep tracking device, comprising:
   a housing;
   a first environmental sensor housed by the housing;
   a contactless radar sensor, housed by the housing, that remotely monitors movement of a user using radar;
   a processing system, comprising one or more processors, housed by the housing, that receives data from the first environmental sensor and the contactless radar sensor, wherein the processing system is configured to:
   determine, based on data received from the contactless radar sensor, that the user has entered a sleep state;
   determine based on radar data received from the contactless radar sensor, a transition time at which the user transitions from the sleep state to an awake state;
   identify an environmental event, based on data received from the first environmental sensor, occurring within a defined time period before the transition time;
   attribute the user waking to the environmental event based on the environmental event occurring within the defined time period before the transition time; and
   output an indication of the attributed environmental event as a cause of the user waking.

2. The contactless sleep tracking device of claim 1, wherein the contactless radar sensor uses low-power continuous wave (CW) radar.

3. The contactless sleep tracking device of claim 2, wherein:
   the first environmental sensor is an ambient light sensor; and
   wherein the processing system attributes the user waking at least in part to ambient light levels based on processing detected ambient light levels from the ambient light sensor.

4. The contactless sleep tracking device of claim 3, wherein the processing comprises determining that an ambient light level has increased by at least a threshold amount.

5. The contactless sleep tracking device of claim 2, wherein:
   the first environmental sensor is a microphone, wherein the processing system attributes the user waking at least in part to sound captured by the microphone.

6. The contactless sleep tracking device of claim 2, further comprising:
   a second environmental sensor; and
   the processing system being configured to identify the environmental event comprises the processing system being configured to:
   compare data received from the first environmental sensor to a first threshold; and
   compare data received from the second environmental sensor to a second threshold, wherein the processing system identifying the environmental event is further based on: data received from the second environmental sensor, comparing data received from the first environmental sensor to the first threshold, and comparing data received from the second environmental sensor to the second threshold.

7. The contactless sleep tracking device of claim 2, wherein the first environmental sensor is a temperature sensor and the environmental event is a temperature change.

8. The contactless sleep tracking device of claim 2, wherein contactless sensor outputs low-power CW radar within 57-64 GHz and a peak EIRP of less than 20 dBm.

9. The contactless sleep tracking device of claim 2, further comprising:
- a wireless network interface housed by the housing;
- an electronic display screen housed by the housing;
- a microphone housed by the housing;
- a speaker housed by the housing; and
- a stand incorporated as part of the housing, wherein:
  - the processing system is in communication with the wireless network interface, the electronic display screen, the microphone, and the speaker.

10. The contactless sleep tracking device of claim 9, wherein the processing system is further configured to:
- receive a voice-based query via the microphone;
- output information based on the voice-based query via the wireless network interface;
- receive data from a cloud-based server system via the wireless network interface; and
- output a response to the voice-based query via the speaker, wherein the response indicates the attributed environmental event as the cause of the user waking.

11. The contactless sleep tracking device of claim 9, wherein the processing system is further configured to output the indication of the attributed environmental event via the electronic display screen, the speaker using synthesized speech, or both.

12. A method for performing contactless sleep monitoring, the method comprising:
- determining, based on radar data received from a contactless radar sensor, that a user has entered a sleep state;
- determining a transition time at which the user transitions from the sleep state to an awake state based on the radar data from the contactless radar sensor;
- identifying an environmental event, based on data received from a first environmental sensor, occurring within a defined time period before the transition time;
- attributing the user waking to the environmental event based on the environmental event occurring within the defined time period before the transition time; and
- outputting an indication of the attributed environmental event as a cause of the user waking.

13. The method for performing contactless sleep monitoring of claim 12, wherein the data received from the contactless radar sensor is based on low-power frequency-modulated continuous wave (FMCW) radar.

14. The method for performing contactless sleep monitoring of claim 12, wherein:
- the first environmental sensor is an ambient light sensor; and
- identifying the environmental event comprises determining that an ambient light level has increased.

15. The method for performing contactless sleep monitoring of claim 12, wherein:
- the first environmental sensor is a microphone; and
- identifying the environmental event comprises determining that a sufficiently loud sound to wake the user has been captured by the microphone.

16. The method for performing contactless sleep monitoring of claim 12, wherein:
- the first environmental sensor is a temperature sensor; and
- identifying the environmental event comprises determining that a temperature change has been detected.

17. The method for performing contactless sleep monitoring of claim 12, further comprising:
- receiving a voice-based query via a microphone; and
- outputting a response to the voice-based query via a speaker, wherein the response indicates the attributed environmental event as the cause of the user waking.

18. The method for performing contactless sleep monitoring of claim 17, the method further comprising:
- output information based on the voice-based query via a wireless network interface; and
- receive data from a cloud-based server system via the wireless network interface.

19. The method for performing contactless sleep monitoring of claim 12, wherein: determining the transition time, identifying the environmental event, attributing the user waking to the environmental event, and outputting the indication of the attributed environmental event as the cause of the user waking are performed by a processing system of a contactless sleep tracking device, wherein the first environmental sensor is part of the contactless sleep tracking device.

* * * * *